United States Patent
Nishida et al.

(10) Patent No.: US 11,220,693 B2
(45) Date of Patent: Jan. 11, 2022

(54) METHOD FOR CONVERTING MONOCOT PLANT GENOME SEQUENCE IN WHICH NUCLEIC ACID BASE IN TARGETED DNA SEQUENCE IS SPECIFICALLY CONVERTED, AND MOLECULAR COMPLEX USED THEREIN

(71) Applicant: NATIONAL UNIVERSITY CORPORATION KOBE UNIVERSITY, Kobe (JP)

(72) Inventors: Keiji Nishida, Kobe (JP); Zenpei Shimatani, Kobe (JP); Akihiko Kondo, Kobe (JP)

(73) Assignee: NATIONAL UNIVERSITY CORPORATION KOBE UNIVERSITY, Kobe (JP)

( * ) Notice: Subject to any disclaimer, the term of this patent is extended or adjusted under 35 U.S.C. 154(b) by 0 days.

(21) Appl. No.: 15/779,120

(22) PCT Filed: Nov. 25, 2016

(86) PCT No.: PCT/JP2016/085075
§ 371 (c)(1),
(2) Date: May 25, 2018

(87) PCT Pub. No.: WO2017/090761
PCT Pub. Date: Jun. 1, 2017

(65) Prior Publication Data
US 2019/0085342 A1  Mar. 21, 2019

(30) Foreign Application Priority Data

Nov. 27, 2015 (JP) ................................ 2015-232379
Jul. 6, 2016 (JP) ............................. JP2016-134613

(51) Int. Cl.
| | |
|---|---|
| C12N 15/82 | (2006.01) |
| C12N 9/10 | (2006.01) |
| C12N 9/78 | (2006.01) |
| C12N 15/09 | (2006.01) |
| C12N 9/16 | (2006.01) |
| C12N 9/22 | (2006.01) |

(52) U.S. Cl.
CPC ............... *C12N 15/82* (2013.01); *C12N 9/10* (2013.01); *C12N 9/16* (2013.01); *C12N 9/22* (2013.01); *C12N 9/78* (2013.01); *C12N 15/09* (2013.01); *C12N 2310/20* (2017.05); *C12Y 305/04005* (2013.01)

(58) Field of Classification Search
None
See application file for complete search history.

(56) References Cited

U.S. PATENT DOCUMENTS

| | | |
|---|---|---|
| 6,117,680 A | 9/2000 | Natesan et al. |
| 8,697,359 B1 | 4/2014 | Zhang |
| 8,772,008 B2 | 7/2014 | Doyon |
| 10,655,123 B2 | 5/2020 | Nishida et al. |
| 10,767,173 B2 | 9/2020 | Mukoyama et al. |
| 2005/0208489 A1 | 9/2005 | Carroll et al. |
| 2011/0002889 A1 | 1/2011 | Barrangou et al. |
| 2011/0104787 A1 | 5/2011 | Church et al. |
| 2011/0145940 A1 | 6/2011 | Voytas et al. |
| 2014/0294773 A1 | 10/2014 | Brouns et al. |
| 2014/0304853 A1 | 10/2014 | Ainley et al. |
| 2014/0335521 A1 | 11/2014 | Nakamura et al. |
| 2014/0356867 A1* | 12/2014 | Peter .................... C12Q 1/6806 435/6.11 |
| 2015/0031134 A1 | 1/2015 | Zhang et al. |
| 2015/0166980 A1 | 6/2015 | Liu et al. |
| 2015/0232882 A1 | 8/2015 | Zhang et al. |

(Continued)

FOREIGN PATENT DOCUMENTS

| | | |
|---|---|---|
| CA | 2933625 A1 | 6/2015 |
| CN | 102770539 A | 11/2012 |

(Continued)

OTHER PUBLICATIONS

Charetai (2015 Plant Biotechnology Journal 13:1002-1010 (Year: 2015).*
Kuscu et al., "CRISPR-Cas9-AID base editor is a powerful gain-of-function screening tool," *Nat. Methods*, 13(12): 983-984 (2016).
Ma et al., "Targeted AID-mediated mutagenesis (TAM) enables efficient genomic diversification in mammalian cells," *Nat. Methods*, 13(12): 1029-1035 and Online Methods (2016).
European Patent Office, Extended European Search Report in European Patent Application No. 17786061.6 (dated Sep. 4, 2019).

(Continued)

*Primary Examiner* — Brent T Page
(74) *Attorney, Agent, or Firm* — Leydig, Voit & Mayer, Ltd.

(57) ABSTRACT

The present invention provides a method of modifying a targeted site of a double stranded DNA of a monocot cell, comprising a step of contacting a complex wherein a nucleic acid sequence-recognizing module that specifically binds to a target nucleotide sequence in the given double stranded DNA and a nucleic acid base converting enzyme are bonded, with said double stranded DNA, to convert one or more nucleotides in the targeted site to other one or more nucleotides or delete one or more nucleotides, or insert one or more nucleotides into said targeted site, without cleaving at least one strand of said double stranded DNA in the targeted site, wherein the double stranded DNA is contacted with the complex by introducing a nucleic acid encoding the complex into the monocot cell. Furthermore, also provided is a complex used for the method, wherein a nucleic acid sequence-recognizing module that specifically binds to a target nucleotide sequence in a double stranded DNA of a monocot cell and a nucleic acid base converting enzyme are bonded.

14 Claims, 15 Drawing Sheets

Specification includes a Sequence Listing.

(56) References Cited

U.S. PATENT DOCUMENTS

| | | | |
|---|---|---|---|
| 2015/0315576 A1 | 11/2015 | Caliando et al. | |
| 2016/0200779 A1 | 7/2016 | Liu et al. | |
| 2017/0073670 A1 | 3/2017 | Nishida et al. | |
| 2017/0121693 A1* | 5/2017 | Liu | C12N 9/22 |
| 2017/0321210 A1 | 11/2017 | Nishida et al. | |
| 2019/0024098 A1 | 1/2019 | Nishida et al. | |
| 2019/0203198 A1 | 7/2019 | Mukoyama et al. | |
| 2020/0208138 A1 | 7/2020 | Nishida et al. | |
| 2020/0248174 A1 | 8/2020 | Nishida et al. | |
| 2020/0377910 A1 | 12/2020 | Nishida et al. | |

FOREIGN PATENT DOCUMENTS

| | | |
|---|---|---|
| CN | 104854241 A | 8/2015 |
| CN | 105934516 A | 9/2016 |
| JP | 2010-519929 A | 6/2010 |
| JP | 4968498 B2 | 7/2012 |
| JP | 2013-513389 A | 4/2013 |
| JP | 2013-128413 A | 7/2013 |
| JP | 2015-503535 A | 2/2015 |
| WO | WO 2010/132092 A2 | 11/2010 |
| WO | WO 2011/072246 A2 | 6/2011 |
| WO | WO 2013/058404 A1 | 4/2013 |
| WO | WO 2013/098244 A1 | 7/2013 |
| WO | WO 2013/140250 A1 | 9/2013 |
| WO | WO 2013/176772 A1 | 11/2013 |
| WO | WO 2014/071235 A1 | 5/2014 |
| WO | WO 2014/093595 A1 | 6/2014 |
| WO | WO 2014/093712 A1 | 6/2014 |
| WO | WO 2015/035136 A2 | 3/2015 |
| WO | WO 2015/089406 A1 | 6/2015 |
| WO | WO 2015/133554 A1 | 9/2015 |
| WO | 2016/069283 A1 | 5/2016 |
| WO | WO 2016/072399 A1 | 5/2016 |
| WO | WO 2017/070632 A2 | 4/2017 |
| WO | WO 2017/090761 A1 | 6/2017 |

OTHER PUBLICATIONS

Conticello et al., "Evolution of the AID/APOBEC Family of Polynucleotide (Deoxy)cytidine Deaminases," *Mol. Biol. Evol.*, 22(2): 367-377 (2005).

Finney-Manchester et al., "Harnessing mutagenic homologous recombination for targeted mutagenesis in vivo by TaGTEAM," *Nucleic Acids Res.*, 41(9): e99 (2013).

Kitamura et al., "Uracil DNA Glycosylase Counteracts APOBEC3G-Induced Hypermutation of Hepatitis B Viral Genomes: Excision Repair of Covalently Closed Circular DNA," *PLoS Pathog.*, 9(5): e1003361 (2013).

O'Connell et al., "Programmable RNA recognition and cleavage by CRISPR/Cas9," *Nature*, 516(7530): 263-266 (2014).

Rogozin et al., "Evolution and diversification of lamprey antigen receptors: evidence for involvement of an AID-APOBEC family cytosine deaminase," *Nat. Immunol.*, 8(6): 647-656 and Supplementary Table 1 (2007).

Szyf et al., "Maternal care, the epigenome and phenotypic differences in behavior," *Reprod. Toxicol.*, 24(1): 9-19 (2007).

Xu et al., "Efficient Genome Editing in *Clostridium cellulolyticum* via CRISPR-Cas9 Nickase," *Appl. Environ. Microbiol.*, 81(13): 4423-4431 and Supplementary Data (2015).

Zeng et al., "Highly efficient editing of the actinorhodin polyketide chain length factor gene in *Streptomyces coelicolor* M145 using CRISPR/Cas9-CodA(sm) combined system," *Appl. Microbiol. Biotechnol.*, 99(24): 10575-10585 (2015).

Japanese Patent Office, International Search Report in International Patent Application No. PCT/JP2016/076448 (dated Dec. 6, 2016).

Japanese Patent Office, International Search Report in International Patent Application No. PCT/JP2016/076711 (dated Nov. 29, 2016).

Japanese Patent Office, International Search Report in International Patent Application No. PCT/JP2017/016105 (dated Jul. 25, 2017).

Canadian Intellectual Property Offce, Examination Report in Canadian Patent Application No. 2,947,941 (dated Mar. 18, 2019).

European Patent Office, Communication Pursuant to Article 94(3) EPC in European Patent Application No. 15758734.6 (dated Apr. 4, 2019).

Bogdanove et al., "TAL Effectors: Customizable Proteins for DNA Targeting," *Science*, 333(6051): 1843-1846 (2011).

Cermak et al., "Efficient design and assembly of custom TALEN and other TAL effector-based constructs for DNA targeting," *Nucleic Acids Research*, 39(12): e82 (2011).

Cho et al., "Targeted genome engineering in human cells with the Cas9 RNA-guided endonuclease," *Nat. Biotechnol.*, 31(3): 230-232 (2013).

Cong et al., "Multiplex Genome Engineering Using CRISPR/Cas Systems," *Science*, 339(6121): 819-823 (2013).

Dicarlo et al., "Genome engineering in *Saccharomyces cerevisiae* using CRISPR-Cas systems," *Nucleic Acids Res.*, 41(7): 4336-4343 (2013).

Esvelt et al., "Genome-scale engineering for systems and synthetic biology," *Molecular Systems Biology*, 9: 641 (2013).

Gilbert et al., "CRISPR-Mediated Modular RNA-Guided Regulation of Transcription in Eukaryotes," *Cell*, 154(2): 442-451 (2013).

Jiang et al., "RNA-guided editing of bacterial genomes using CRISPR-Cas systems," *Nat. Biotechnol.*, 31(3): 233-239 and online methods [2 pages] (2013).

Jinek et al., "A Programmable Dual-RNA-Guided DNA Endonuclease in Adaptive Bacterial Immunity," *Science*, 337(6096): 816-821 (2012).

Jinek et al., "RNA-programmed genome editing in human cells," *eLIFE*, 2: e00471 (2013).

Kim et al., "Genome-wide target specificities of CRISPR RNA-guided programmable deaminases," *Nat. Biotechnol.*, 35(5): 475-480 (2017).

Komor et al., "Programmable editing of a target base in genomic DNA without double-stranded DNA cleavage," *Nature*, 533(7603): 420-424 (2016).

Krokan et al., "Base Excision Repair," *Cold Spring Harb. Perspect. Biol.*, 5(4): a012583 (2013).

Lada et al., "AID/APOBEC cytosine deaminase induces genome-wide kataegis," *Biol. Direct*, 7: 47 (2012).

Lada et al., "Genome-Wide Mutation Avalanches Induced in Diploid Yeast Cells by a Base Analog or an APOBEC Deaminase," *PLoS Genet.*, 9(9): e1003736 (2013).

Mali et al., "CAS9 transcriptional activators for target specificity screening and paired nickases for cooperative genome engineering," *Nat. Biotechnol.*, 31(9): 833-838 and Online Methods (2013).

Mali et al., "Cas9 as a versatile tool for engineering biology," *Nature Methods*, 10(10): 957-963 (2013).

Mali et al., "RNA-Guided Human Genome Engineering via Cas9," *Science*: 339(6121): 823-826 (2013).

Mussolino et al., "TALE nucleases: tailored genome engineering made easy," *Current Opinion in Biotechnology*, 23(5): 644-650 (2012).

Nishida et al., "Targeted nucleotide editing using hybrid prokaryotic and vertebrate adaptive immune systems," *Science*, 353(6305): aaf8729 (2016).

Osakabe et al., "Genome Editing with Engineered Nucleases in Plants," *Plant Cell Physiol.*, 56(3): 389-400 (2015).

Perez-Pinera et al., "RNA-guided gene activation by CRISPR-Cas9-based transcription factors," *Nat. Methods*, 10(10): 973-976 (2013).

Plosky, "CRISPR-Mediated Base Editing without DNA Double-Strand Breaks," *Mol. Cell.*, 62(4): 477-478 (2016).

Ran et al., "Genome engineering using the CRISPR-Cas9 system," *Nat. Protoc.*, 8(11): 2281-2308 (2013).

Shalem et al., "Genome-Scale CRISPR-Cas9 Knockout Screening in Human Cells," *Science*, 343(6166): 84-87 and Supplementary Materials [78 pages] (2013).

Shimatani et al., "Targeted base editing in rice and tomato using a CRISPR-Cas9 cytidine deaminase fusion," *Nat. Biotechnol.*, 35(5): 441-443, Online Methods, and Corrigendum (2017).

Zetsche et al., "Cpf1 Is a Single RNA-Guided Endonuclease of a Class 2 CRISPR-Cas System," *Cell*, 163(3): 759-771 (2015).

(56) References Cited

OTHER PUBLICATIONS

Canadian Intellectual Property Office, Official Action and Examination Search Report in Canadian Patent Application No. 2,947,941 (dated Dec. 15, 2017).
Canadian Intellectual Property Office, Examination Report in Canadian Patent Application No. 2,947,941 (dated Jun. 22, 2018).
European Patent Office, Communication Pursuant to Article 94(3) EPC in European Patent Application No. 15758734.6 (dated May 4, 2018).
Japanese Patent Office, International Preliminary Report on Patentability in International Patent Application No. PCT/JP2015/056436 (dated May 10, 2016).
Japanese Patent Office, International Search Report in International Patent Application No. PCT/JP2015/056436 (dated Jun. 9, 2015).
Japanese Patent Office, International Search Report in International Patent Application No. PCT/JP2016/085075 (dated Feb. 21, 2017).
Japanese Patent Office, Official Action in Japanese Patent Application No. 2017-164703 (dated May 16, 2018).
Bortesi et al., "The CRISPR/Cas9 system for plant genome editing and beyond," *Biotechnol. Adv.*, 33(1): 41-52 (2015).
Chinese Patent Office, Second Office Action in Chinese Patent Application No. 201580023875.6 (dated May 7, 2019).
Fang et al., "New Method of Genome Editing Derived From CRISPR/Cas9," *Prog. Biochem. Biophys.* 40(8): 691-702 (2013).
Horvath et al., "CRISPR/Cas, the Immune System of Bacteria and Archaea," *Science*, 327: 167-170 (2010).
Makarova et al., "Evolution and classification of the CRISPR-Cas systems," *Nat. Rev. Microbiol.*, 9(6): 467-477 (2011).
Pingoud et al., "Type II restrictions endonucleases—a historical perspective and more," *Nucleic Acids Res.*, 42(12): 7489-7527 (2014).
Ran et al., "Double Nicking by RNA-Guided CRISPR Cas9 for Enhanced Genome Editing Specificity," *Cell*, 154(6): 1380-1389 (2013).
Rittié et al., "Enzymes used in molecular biology: a useful guide," *J. Cell. Commun. Signal.*, 2(1-2): 25-45 (2008).
Shmakov et al., "Discovery and Functional Characterization of Diverse Class 2 CRISPR-Cas Systems," *Mol Cell*, 60(3): 385-397 (2015).
Chinese Patent Office, First Office Action in Chinese Patent Application No. 201580023875.6 (dated Sep. 3, 2018).
Arazoe et al., "Targeted Nucleotide Editing Technologies for Microbial Metabolic Engineering," *Biotechnol. J.*, 13(9): e1700596 (2018).
Mitsunobu et al., "Beyond Native Cas9: Manipulating Genomic Information and Function," *Trends Biotechnol.*, 35(10): 983-996 (2017).
Lada et al., "Mutator Effects and Mutation Signatures of Editing Deaminases Produced in Bacteria and Yeast," *Biochemistry* (Moscow), 76(1): 131-146 (2011).
Jinek et al., "Structures of Cas9 Endonucleases Reveal RNA-Mediated Conformational Activation," *Science*, 343(6176): 1247997 and Supplementary Materials (2014).
Sinkunas et al., "Cas3 is a single-stranded DNA nuclease and ATP-dependent helicase in the CRISPR/Cas immune system," *EMBO J.*, 30: 1335-1342 (2011).

European Patent Office, Communication Pursuant to Article 94(3) EPC in European Patent Application No. 19196085.5 (dated Jan. 12, 2021).
Wolf et al., "tadA, an essential tRNA-specific adenosine deaminase from *Escherichia coli*," *EMBO J.*, 21(14): 3841-3851 (2002).
Freitas et al., "Mechanisms and Signals for the Nuclear Import of Proteins," *Curr. Genomics*, 10(8): 550-557 (2009).
Harris et al., "RNA Editing Enzyme APOBEC1 and Some of Its Homologs Can Act as DNA Mutators," *Mol. Cell*, 10(5): 1247-1253 (2002).
European Patent Office, Communication Pursuant to Article 94(3) EPC in European Patent Application No. 16844517.9 (dated Apr. 14, 2021).
European Patent Office, Summons to Attend Oral Proceedings Pursuant to Rule 115(1) EPC in European Patent Application No. 16868704.4 (May 27, 2021).
China National Intellectual Property Administration, Office Action and Search Report in Chinese Patent Application No. 201680079887.5 (dated May 18, 2021).
U.S. Appl. No. 15/124,021, filed Nov. 9, 2016.
U.S. Appl. No. 15/757,243, filed Mar. 2, 2018.
U.S. Appl. No. 15/757,646, filed Mar. 5, 2018.
U.S. Appl. No. 16/094,587, filed Oct. 18, 2018.
U.S. Appl. No. 16/791,968, filed Feb. 14, 2020.
U.S. Appl. No. 16/838,960, filed Apr. 2, 2020.
China National Intellectual Property Administration, First Office Action and Search Report in Chinese Patent Application No. 201680065297.7 (dated Jan. 6, 2021).
Intellectual Property Office of Singapore, Written Opinion in Singaporean Patent Application No. 11201809242V (dated Feb. 25, 2021).
Intellectual Property Office of Singapore, Invitation to Respond to Written Opinion in Singaporean Patent Application No. 11201809242V (dated Feb. 26, 2021).
Japanese Patent Office, Official Action in Japanese Patent Application No. 2018-513234 (dated Feb. 24, 2021).
Al-Fageeh et al., "The Cold-Shock Response in Cultured Mammalian Cells: Harnessing the Response for the Improvement of Recombinanat Protein Production," *Biotechnol. Bioeng.*, 93(5): 829-835 (2006).
Kim et al., "Highly efficient RNA-guided genome editing in human cells via delivery of purified Cas9 ribonucleoproteins," *Genome Res.*, 24(6): 1012-1019 and Supplemental Information (2014).
Lada, "Mechanisms of regulation of AID/APOBEC deaminases activity and protection of the genome from promiscuous deamination," Dissertation to University of Nebraska Medical Center (Jun. 2014).
Makarova et al., "An updated evolutionary classification of CRISPR-Cas systems," *Nat. Rev. Microbiol.*, 13(11): 722-736 (2015).
Ramakrishna et al., "Gene disruption by cell-penetrating peptide-mediated delivery of Cas9 protein and guide RNA," *Genome Res.*, 24(6): 1020-1027 and Supplemental Information (2014).
Remy et al., "Efficient gene targeting by homology-directed repair in rat zygotes using TALE nucleases," *Genome Res.*, 24(8): 1371-1383 and Supplemental Information (2014).

* cited by examiner light field          fluorescence

Fig. 4
pRIT3-mEGFP+2409 No.6
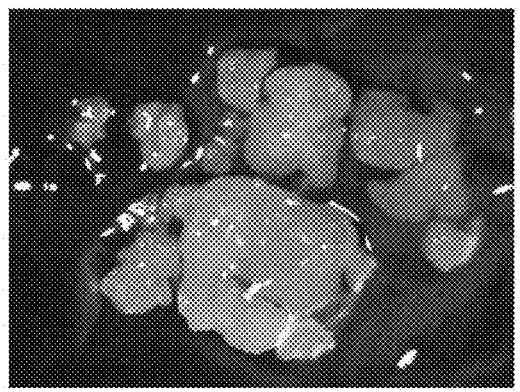 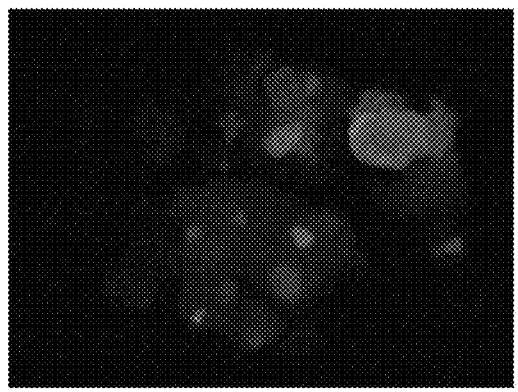
light field  fluorescence
Fig. 5
pRIT3-mEGFP+2409 No.3
fluorescence

Fig. 6

Fig. 7 pRIT3-mEGFP + 2409 Line No.39

Fig. 10 pRIT3-mEGFP + 2408 Line No.4

Fig. 11 pRIT3-mEGFP + 2408 Line No.1D

Cell in same line with No.1 and with no GFP signal.
Adjacent but no mutation of target sequence.

Consistent results with analysis results of GFP reporter.

12/12 (100%)

Fig. 12
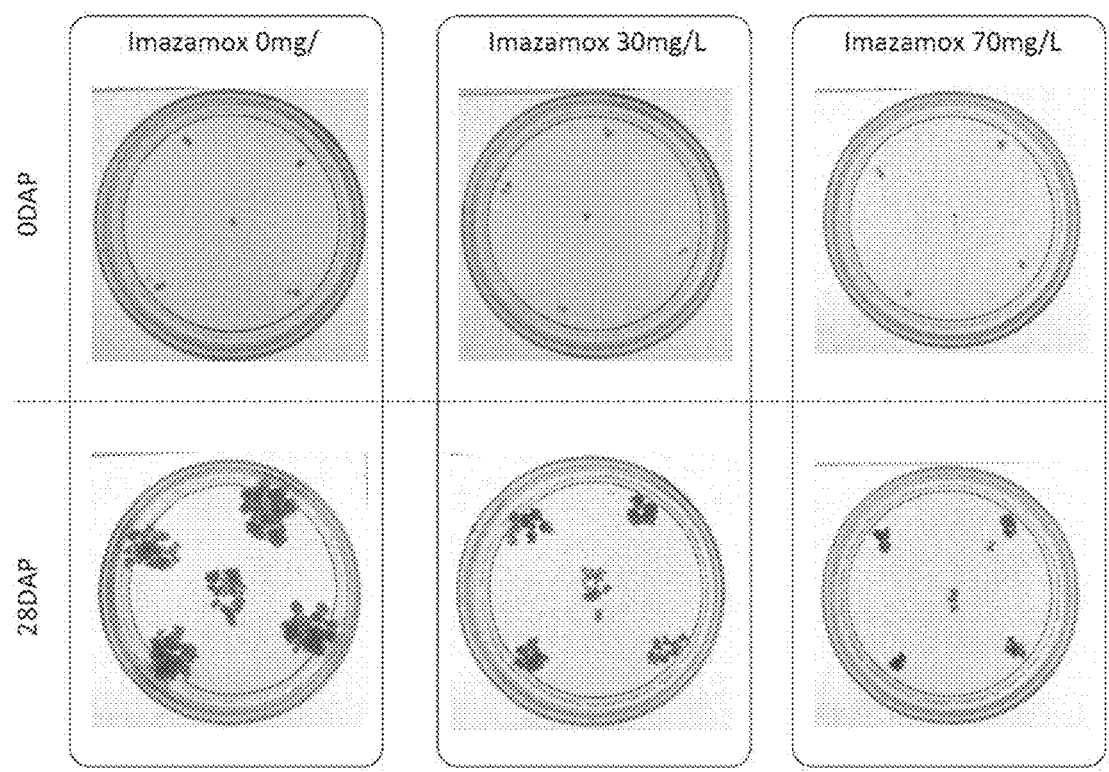
Fig. 13
pRIT4-ALS WT
pRIT4-ALS A96V

1477 Line No.114
T0 plant

1477
Line No.114
T0 plant No.2

SerAspValPheAlaTyrProGlyGly | Ala | SerMetGluIleHisGlnAlaLeuThrArg    SEQ ID NO:43
                              | Val |                                   SEQ ID NO:46
AGCGACGTGTTCGCCTACCCGGGCGGC | GCG | TCCATGGAGATCCACCAGGCGCTGACGCGC     SEQ ID NO:44
                              | GTG |                                   SEQ ID NO:47

B

1477
Line No.156
T0 plant No.2

SerAspValPheAlaTyrProGly | Gly | Ala | SerMetGluIleHisGlnAlaLeuThrArg    SEQ ID NO:43
                                | Val |                                   SEQ ID NO:46
AGCGACGTGTTCGCCTACCCGGGC | GGC | GCG | TCCATGGAGATCCACCAGGCGCTGACGCGC     SEQ ID NO:44
                          | GGT | GTG |                                   SEQ ID NO:49

SEQUENCE LISTING

```
<160> NUMBER OF SEQ ID NOS: 53

<210> SEQ ID NO 1
<211> LENGTH: 627
<212> TYPE: DNA
<213> ORGANISM: Artificial Sequence
<220> FEATURE:
<223> OTHER INFORMATION: Synthetic Sequence PmCDA codon-optimized for
      Arabidopsis thaliana
<220> FEATURE:
<221> NAME/KEY: CDS
```

<222> LOCATION: (1)..(627)

<400> SEQUENCE: 1

| atg | aca | gat | gct | gaa | tat | gtc | aga | atc | cac | gaa | aag | ttg | gac | att | tac | 48 |
| Met | Thr | Asp | Ala | Glu | Tyr | Val | Arg | Ile | His | Glu | Lys | Leu | Asp | Ile | Tyr | |
| 1 | | | | 5 | | | | | 10 | | | | | 15 | | |

| acg | ttt | aag | aag | cag | ttc | ttc | aac | aac | aag | aaa | tct | gtt | tcg | cat | agg | 96 |
| Thr | Phe | Lys | Lys | Gln | Phe | Phe | Asn | Asn | Lys | Lys | Ser | Val | Ser | His | Arg | |
| | | | 20 | | | | | 25 | | | | | 30 | | | |

| tgc | tat | gtg | ctt | ttc | gaa | cta | aaa | cgt | cgt | gga | gaa | aga | cgg | gct | tgc | 144 |
| Cys | Tyr | Val | Leu | Phe | Glu | Leu | Lys | Arg | Arg | Gly | Glu | Arg | Arg | Ala | Cys | |
| | | | 35 | | | | | 40 | | | | | 45 | | | |

| ttt | tgg | ggt | tac | gcg | gtt | aac | aaa | cca | caa | tca | ggt | act | gaa | cga | gga | 192 |
| Phe | Trp | Gly | Tyr | Ala | Val | Asn | Lys | Pro | Gln | Ser | Gly | Thr | Glu | Arg | Gly | |
| 50 | | | | | 55 | | | | | 60 | | | | | | |

| ata | cac | gct | gaa | atc | ttt | tct | atc | cga | aag | gtt | gag | gaa | tat | cta | cgt | 240 |
| Ile | His | Ala | Glu | Ile | Phe | Ser | Ile | Arg | Lys | Val | Glu | Glu | Tyr | Leu | Arg | |
| 65 | | | | | 70 | | | | | 75 | | | | | 80 | |

| gac | aat | cct | gga | cag | ttc | act | atc | aat | tgg | tat | tct | agc | tgg | tca | cca | 288 |
| Asp | Asn | Pro | Gly | Gln | Phe | Thr | Ile | Asn | Trp | Tyr | Ser | Ser | Trp | Ser | Pro | |
| | | | | 85 | | | | | 90 | | | | | 95 | | |

| tgt | gca | gat | tgt | gct | gag | aag | att | ctc | gaa | tgg | tac | aat | caa | gag | ctt | 336 |
| Cys | Ala | Asp | Cys | Ala | Glu | Lys | Ile | Leu | Glu | Trp | Tyr | Asn | Gln | Glu | Leu | |
| | | | 100 | | | | | 105 | | | | | 110 | | | |

| aga | ggc | aat | gga | cat | aca | ttg | aaa | ata | tgg | gca | tgc | aag | ctc | tac | tac | 384 |
| Arg | Gly | Asn | Gly | His | Thr | Leu | Lys | Ile | Trp | Ala | Cys | Lys | Leu | Tyr | Tyr | |
| | | | | 115 | | | | | 120 | | | | | 125 | | |

| gaa | aag | aat | gcc | aga | aac | caa | att | ggg | ctt | tgg | aac | ttg | agg | gat | aat | 432 |
| Glu | Lys | Asn | Ala | Arg | Asn | Gln | Ile | Gly | Leu | Trp | Asn | Leu | Arg | Asp | Asn | |
| | 130 | | | | | 135 | | | | | 140 | | | | | |

| gga | gtt | ggg | ctt | aat | gtc | atg | gtt | tct | gag | cac | tat | caa | tgt | tgt | cgg | 480 |
| Gly | Val | Gly | Leu | Asn | Val | Met | Val | Ser | Glu | His | Tyr | Gln | Cys | Cys | Arg | |
| 145 | | | | | 150 | | | | | 155 | | | | | 160 | |

| aag | atc | ttc | ata | caa | agt | tcc | cat | aac | cag | ttg | aat | gag | aac | aga | tgg | 528 |
| Lys | Ile | Phe | Ile | Gln | Ser | Ser | His | Asn | Gln | Leu | Asn | Glu | Asn | Arg | Trp | |
| | | | | 165 | | | | | 170 | | | | | 175 | | |

| tta | gag | aaa | acc | ctt | aaa | aga | gcc | gag | aag | aga | aga | tcc | gaa | ctg | agc | 576 |
| Leu | Glu | Lys | Thr | Leu | Lys | Arg | Ala | Glu | Lys | Arg | Arg | Ser | Glu | Leu | Ser | |
| | | | 180 | | | | | 185 | | | | | 190 | | | |

| att | atg | ata | cag | gtc | aaa | att | ctg | cat | acc | act | aag | agt | cca | gct | gta | 624 |
| Ile | Met | Ile | Gln | Val | Lys | Ile | Leu | His | Thr | Thr | Lys | Ser | Pro | Ala | Val | |
| | | | 195 | | | | | 200 | | | | | 205 | | | |

| ggt | | | | | | | | | | | | | | | | 627 |
| Gly | | | | | | | | | | | | | | | | |

<210> SEQ ID NO 2
<211> LENGTH: 209
<212> TYPE: PRT
<213> ORGANISM: Artificial Sequence
<220> FEATURE:
<223> OTHER INFORMATION: Synthetic Construct

<400> SEQUENCE: 2

| Met | Thr | Asp | Ala | Glu | Tyr | Val | Arg | Ile | His | Glu | Lys | Leu | Asp | Ile | Tyr |
| 1 | | | | 5 | | | | | 10 | | | | | 15 | |

| Thr | Phe | Lys | Lys | Gln | Phe | Phe | Asn | Asn | Lys | Lys | Ser | Val | Ser | His | Arg |
| | | | 20 | | | | | 25 | | | | | 30 | | |

| Cys | Tyr | Val | Leu | Phe | Glu | Leu | Lys | Arg | Arg | Gly | Glu | Arg | Arg | Ala | Cys |
| | | | 35 | | | | | 40 | | | | | 45 | | |

| Phe | Trp | Gly | Tyr | Ala | Val | Asn | Lys | Pro | Gln | Ser | Gly | Thr | Glu | Arg | Gly |

```
            50                  55                  60
Ile His Ala Glu Ile Phe Ser Ile Arg Lys Val Glu Glu Tyr Leu Arg
 65                  70                  75                  80

Asp Asn Pro Gly Gln Phe Thr Ile Asn Trp Tyr Ser Ser Trp Ser Pro
                 85                  90                  95

Cys Ala Asp Cys Ala Glu Lys Ile Leu Glu Trp Tyr Asn Gln Glu Leu
            100                 105                 110

Arg Gly Asn Gly His Thr Leu Lys Ile Trp Ala Cys Lys Leu Tyr Tyr
        115                 120                 125

Glu Lys Asn Ala Arg Asn Gln Ile Gly Leu Trp Asn Leu Arg Asp Asn
130                 135                 140

Gly Val Gly Leu Asn Val Met Val Ser Glu His Tyr Gln Cys Cys Arg
145                 150                 155                 160

Lys Ile Phe Ile Gln Ser Ser His Asn Gln Leu Asn Glu Asn Arg Trp
                165                 170                 175

Leu Glu Lys Thr Leu Lys Arg Ala Glu Lys Arg Ser Glu Leu Ser
            180                 185                 190

Ile Met Ile Gln Val Lys Ile Leu His Thr Thr Lys Ser Pro Ala Val
        195                 200                 205

Gly

<210> SEQ ID NO 3
<211> LENGTH: 4104
<212> TYPE: DNA
<213> ORGANISM: Artificial Sequence
<220> FEATURE:
<223> OTHER INFORMATION: Synthetic Sequence Cas9 codon-optimized for
      rice
<220> FEATURE:
<221> NAME/KEY: CDS
<222> LOCATION: (1)..(4101)

<400> SEQUENCE: 3 atg gac aag aag tac tcg atc ggg ctg gmc atc gga aca aat tct gta       48
Met Asp Lys Lys Tyr Ser Ile Gly Leu Xaa Ile Gly Thr Asn Ser Val
1               5                  10                  15 ggc tgg gct gta ata acc gat gag tac aag gtg ccc tct aaa aaa ttt       96
Gly Trp Ala Val Ile Thr Asp Glu Tyr Lys Val Pro Ser Lys Lys Phe
             20                  25                  30 aag gtc ctt ggc aat acg gat aga cat tcc ata aag aag aat ctt atc      144
Lys Val Leu Gly Asn Thr Asp Arg His Ser Ile Lys Lys Asn Leu Ile
         35                  40                  45 ggt gcg ctg ctc ttt gac agc ggc gag acc gcg gag gcg acc cgg ttg      192
Gly Ala Leu Leu Phe Asp Ser Gly Glu Thr Ala Glu Ala Thr Arg Leu
     50                  55                  60 aaa cgc acc gcg aga cgc cgt tac aca agg cgt aag aat aga atc tgt      240
Lys Arg Thr Ala Arg Arg Arg Tyr Thr Arg Arg Lys Asn Arg Ile Cys
 65                  70                  75                  80 tat ctc cag gag ata ttc tct aat gaa atg gcg aag gta gac gat tcc      288
Tyr Leu Gln Glu Ile Phe Ser Asn Glu Met Ala Lys Val Asp Asp Ser
                 85                  90                  95 ttc ttt cac cgt ctg gag gaa agt ttt ctc gtt gag gaa gat aag aaa      336
Phe Phe His Arg Leu Glu Glu Ser Phe Leu Val Glu Glu Asp Lys Lys
            100                 105                 110 cat gaa aga cac ccg atc ttc gga aac att gtc gac gag gtc gct tat      384
His Glu Arg His Pro Ile Phe Gly Asn Ile Val Asp Glu Val Ala Tyr
        115                 120                 125 cat gaa aag tac cct acc atc tac cat ctt aga aag aaa ctt gtt gac      432
His Glu Lys Tyr Pro Thr Ile Tyr His Leu Arg Lys Lys Leu Val Asp
```

-continued

|     |     |     |     |     | 130 |     |     |     |     | 135 |     |     |     |     | 140 |     |      |
|-----|-----|-----|-----|-----|-----|-----|-----|-----|-----|-----|-----|-----|-----|-----|-----|-----|------|

```
agc acg gat aag gct gat ctc agg ctg ata tac ctg gct ctg gca cat        480
Ser Thr Asp Lys Ala Asp Leu Arg Leu Ile Tyr Leu Ala Leu Ala His
145             150                 155                 160 atg att aag ttc aga ggg cat ttc ctt atc gaa ggc gac ctg aat cca        528
Met Ile Lys Phe Arg Gly His Phe Leu Ile Glu Gly Asp Leu Asn Pro
            165                 170                 175 gat aat tca gat gta gac aag ctc ttc att caa ctt gtg cag act tat        576
Asp Asn Ser Asp Val Asp Lys Leu Phe Ile Gln Leu Val Gln Thr Tyr
        180                 185                 190 aat cag ctc ttc gaa gaa aat cca ata aac gcg tcg ggt gta gac gca        624
Asn Gln Leu Phe Glu Glu Asn Pro Ile Asn Ala Ser Gly Val Asp Ala
    195                 200                 205 aag gcc ata ctg tcc gct agg ctt tct aag tca cgt aga ctt gag aat        672
Lys Ala Ile Leu Ser Ala Arg Leu Ser Lys Ser Arg Arg Leu Glu Asn
210                 215                 220 ctc att gcc caa ctc ccc ggc gag aag aag aac ggc ttg ttt gga aat        720
Leu Ile Ala Gln Leu Pro Gly Glu Lys Lys Asn Gly Leu Phe Gly Asn
225                 230                 235                 240 ctg ata gcg ctg tcc ctg ggt ctt aca cca aat ttc aag agt aat ttc        768
Leu Ile Ala Leu Ser Leu Gly Leu Thr Pro Asn Phe Lys Ser Asn Phe
                245                 250                 255 gat ttg gca gaa gat gct aag ttg cag ctc agt aaa gac acc tac gat        816
Asp Leu Ala Glu Asp Ala Lys Leu Gln Leu Ser Lys Asp Thr Tyr Asp
            260                 265                 270 gac gat ctt gat aat ttg ttg gct cag att ggc gat cag tat gca gat        864
Asp Asp Leu Asp Asn Leu Leu Ala Gln Ile Gly Asp Gln Tyr Ala Asp
        275                 280                 285 ctt ttc ttg gcc gct aag aat ttg tct gat gca att ctg ctt agc gac        912
Leu Phe Leu Ala Ala Lys Asn Leu Ser Asp Ala Ile Leu Leu Ser Asp
    290                 295                 300 att ttg agg gtt aat aca gaa atc acc aag gca ccc ttg tcg gcg tca        960
Ile Leu Arg Val Asn Thr Glu Ile Thr Lys Ala Pro Leu Ser Ala Ser
305                 310                 315                 320 atg ata aag agg tat gat gag cac cac caa gac ctg acg ctc ctc aag       1008
Met Ile Lys Arg Tyr Asp Glu His His Gln Asp Leu Thr Leu Leu Lys
                325                 330                 335 gct ctt gtt cgg cag caa ttg ccg gag aag tac aaa gag atc ttc ttc       1056
Ala Leu Val Arg Gln Gln Leu Pro Glu Lys Tyr Lys Glu Ile Phe Phe
            340                 345                 350 gac cag tct aag aac gga tat gcg ggc tac ata gac ggt gga gcg agt       1104
Asp Gln Ser Lys Asn Gly Tyr Ala Gly Tyr Ile Asp Gly Gly Ala Ser
        355                 360                 365 cag gag gaa ttc tac aag ttc ata aag ccc att ctc gag aag atg gat       1152
Gln Glu Glu Phe Tyr Lys Phe Ile Lys Pro Ile Leu Glu Lys Met Asp
    370                 375                 380 ggt acg gaa gaa ctg ctt gtg aaa ctt aac aga gaa gat ctt ttg cgg       1200
Gly Thr Glu Glu Leu Leu Val Lys Leu Asn Arg Glu Asp Leu Leu Arg
385                 390                 395                 400 aag cag aga act ttc gac aac gga agt ata cca cac cag ata cat ctc       1248
Lys Gln Arg Thr Phe Asp Asn Gly Ser Ile Pro His Gln Ile His Leu
                405                 410                 415 gga gag ctt cat gct att ctc aga aga caa gag gat ttc tac cct ttc       1296
Gly Glu Leu His Ala Ile Leu Arg Arg Gln Glu Asp Phe Tyr Pro Phe
            420                 425                 430 ttg aag gat aac aga gaa aag ata gag aag atc ctc acg ttt agg atc       1344
Leu Lys Asp Asn Arg Glu Lys Ile Glu Lys Ile Leu Thr Phe Arg Ile
        435                 440                 445 cct tac tac gta ggt cct ctt gct cgc ggc aat agt agg ttc gcc tgg       1392
```

-continued

```
Pro Tyr Tyr Val Gly Pro Leu Ala Arg Gly Asn Ser Arg Phe Ala Trp
        450                 455                 460 atg acc cgc aag tct gaa gaa act atc acc cct tgg aat ttc gaa gag   1440
Met Thr Arg Lys Ser Glu Glu Thr Ile Thr Pro Trp Asn Phe Glu Glu
465                 470                 475                 480 gtt gta gac aaa ggt gct tca gca cag agt ttc att gag agg atg acc   1488
Val Val Asp Lys Gly Ala Ser Ala Gln Ser Phe Ile Glu Arg Met Thr
                485                 490                 495 aac ttc gac aag aac ctc ccc aac gaa aag gtc ctg cct aag cac agc   1536
Asn Phe Asp Lys Asn Leu Pro Asn Glu Lys Val Leu Pro Lys His Ser
            500                 505                 510 ctc ctc tac gaa tac ttt act gtc tat aat gag ctt aca aaa gtt aag   1584
Leu Leu Tyr Glu Tyr Phe Thr Val Tyr Asn Glu Leu Thr Lys Val Lys
        515                 520                 525 tac gtg aca gag gga atg cgg aag ccc gca ttc ctt tcc gga gaa caa   1632
Tyr Val Thr Glu Gly Met Arg Lys Pro Ala Phe Leu Ser Gly Glu Gln
    530                 535                 540 aag aag gcg atc gtg gat ctt ctc ttc aag acg aac cgc aag gtg acg   1680
Lys Lys Ala Ile Val Asp Leu Leu Phe Lys Thr Asn Arg Lys Val Thr
545                 550                 555                 560 gtt aaa cag ttg aag gaa gat tac ttc aag aag ata gaa tgt ttt gat   1728
Val Lys Gln Leu Lys Glu Asp Tyr Phe Lys Lys Ile Glu Cys Phe Asp
                565                 570                 575 agc gtg gaa atc agc ggc gtc gaa gat agg ttc aac gct tcc ctg gga   1776
Ser Val Glu Ile Ser Gly Val Glu Asp Arg Phe Asn Ala Ser Leu Gly
            580                 585                 590 acg tac cac gat ctc ctc aag att atc aaa gat aag gac ttt ctt gat   1824
Thr Tyr His Asp Leu Leu Lys Ile Ile Lys Asp Lys Asp Phe Leu Asp
        595                 600                 605 aac gaa gag aat gag gac atc ttg gaa gac att gtt ctg acg ctc acc   1872
Asn Glu Glu Asn Glu Asp Ile Leu Glu Asp Ile Val Leu Thr Leu Thr
    610                 615                 620 ctg ttc gaa gat cgc gag atg att gag gaa cgc ttg aag acc tac gca   1920
Leu Phe Glu Asp Arg Glu Met Ile Glu Glu Arg Leu Lys Thr Tyr Ala
625                 630                 635                 640 cac ctg ttc gat gac aag gtt atg aag caa ctt aaa cgg cgc cgg tat   1968
His Leu Phe Asp Asp Lys Val Met Lys Gln Leu Lys Arg Arg Arg Tyr
                645                 650                 655 acg ggc tgg gga cgg ctt tcg cgg aag ctg ata aat gga atc cgt gac   2016
Thr Gly Trp Gly Arg Leu Ser Arg Lys Leu Ile Asn Gly Ile Arg Asp
            660                 665                 670 aag cag tct ggc aag aca ata ctc gac ttc ttg aag tcg gat ggt ttt   2064
Lys Gln Ser Gly Lys Thr Ile Leu Asp Phe Leu Lys Ser Asp Gly Phe
        675                 680                 685 gcc aat aga aat ttt atg caa ctc att cat gat gac tcg ctt act ttt   2112
Ala Asn Arg Asn Phe Met Gln Leu Ile His Asp Asp Ser Leu Thr Phe
    690                 695                 700 aag gag gac atc cag aag gcc cag gta tca gga cag ggt gac tct ttg   2160
Lys Glu Asp Ile Gln Lys Ala Gln Val Ser Gly Gln Gly Asp Ser Leu
705                 710                 715                 720 cac gaa cac atc gcg aac ctg gcg ggc tcc ccc gcg att aag aag gga   2208
His Glu His Ile Ala Asn Leu Ala Gly Ser Pro Ala Ile Lys Lys Gly
                725                 730                 735 att ttg cag act gtc aag gtg gtc gat gaa ctc gtg aag gtt atg gga   2256
Ile Leu Gln Thr Val Lys Val Val Asp Glu Leu Val Lys Val Met Gly
            740                 745                 750 cgt cat aag ccg gaa aat att gtg att gag atg gct cgc gag aat caa   2304
Arg His Lys Pro Glu Asn Ile Val Ile Glu Met Ala Arg Glu Asn Gln
        755                 760                 765
```

```
                                       -continued aca aca cag aag ggc caa aag aac agt aga gaa cgc atg aag cgc atc    2352
Thr Thr Gln Lys Gly Gln Lys Asn Ser Arg Glu Arg Met Lys Arg Ile
    770             775                 780 gaa gag ggc atc aaa gag ctg ggc agt cag atc ctt aaa gaa cat cca    2400
Glu Glu Gly Ile Lys Glu Leu Gly Ser Gln Ile Leu Lys Glu His Pro
785             790                 795                 800 gtc gag aat aca cag ctt cag aac gaa aag ctg tac ctt tat tac ctt    2448
Val Glu Asn Thr Gln Leu Gln Asn Glu Lys Leu Tyr Leu Tyr Tyr Leu
            805                 810                 815 caa aat ggg cgt gat atg tat gtg gat cag gaa ctc gat atc aat agg    2496
Gln Asn Gly Arg Asp Met Tyr Val Asp Gln Glu Leu Asp Ile Asn Arg
        820                 825                 830 ctg agt gac tat gat gtc gac smt atc gtc ccg caa agt ttc ctc aag    2544
Leu Ser Asp Tyr Asp Val Asp Xaa Ile Val Pro Gln Ser Phe Leu Lys
            835                 840                 845 gac gac agt ata gac aac aaa gtt ctc aca cgg tca gat aag aat cgc    2592
Asp Asp Ser Ile Asp Asn Lys Val Leu Thr Arg Ser Asp Lys Asn Arg
850                 855                 860 ggc aag agc gat aat gta ccg tcg gag gag gta gtc aag aag atg aag    2640
Gly Lys Ser Asp Asn Val Pro Ser Glu Glu Val Val Lys Lys Met Lys
865                 870                 875                 880 aat tac tgg cgc cag ttg ctc aac gcc aag ctc atc act cag agg aaa    2688
Asn Tyr Trp Arg Gln Leu Leu Asn Ala Lys Leu Ile Thr Gln Arg Lys
                885                 890                 895 ttt gac aac ctt acg aaa gcc gag cgg ggc gga ctc tct gaa ctg gac    2736
Phe Asp Asn Leu Thr Lys Ala Glu Arg Gly Gly Leu Ser Glu Leu Asp
            900                 905                 910 aag gcc ggt ttc ata aag cgc cag ctc gtt gag aca cgt caa att act    2784
Lys Ala Gly Phe Ile Lys Arg Gln Leu Val Glu Thr Arg Gln Ile Thr
        915                 920                 925 aag cac gtc gct caa ata ttg gat tcc cgc atg aat act aag tac gat    2832
Lys His Val Ala Gln Ile Leu Asp Ser Arg Met Asn Thr Lys Tyr Asp
    930                 935                 940 gag aat gat aag ctc ata cgt gaa gtt aag gtc att act ctc aag tcc    2880
Glu Asn Asp Lys Leu Ile Arg Glu Val Lys Val Ile Thr Leu Lys Ser
945                 950                 955                 960 aag ctt gta tcg gac ttc cgt aag gac ttc caa ttc tac aag gtc cgg    2928
Lys Leu Val Ser Asp Phe Arg Lys Asp Phe Gln Phe Tyr Lys Val Arg
                965                 970                 975 gaa atc aat aat tat cac cat gcc cat gac gct tat ctg aac gcg gtc    2976
Glu Ile Asn Asn Tyr His His Ala His Asp Ala Tyr Leu Asn Ala Val
            980                 985                 990 gtg ggc acg gca ctc att aag aaa tac cca aaa ctt gag tca gaa ttt    3024
Val Gly Thr Ala Leu Ile Lys Lys Tyr Pro Lys Leu Glu Ser Glu Phe
        995                 1000                1005 gtt tac ggg gac tat aaa gtt tat gac gtg cgg aag atg ata gcg        3069
Val Tyr Gly Asp Tyr Lys Val Tyr Asp Val Arg Lys Met Ile Ala
    1010                1015                1020 aag tcg gaa caa gag ata gga aag gcg act gca aag tac ttt ttt        3114
Lys Ser Glu Gln Glu Ile Gly Lys Ala Thr Ala Lys Tyr Phe Phe
1025                1030                1035 tac tcc aac ata atg aat ttc ttt aag acc gaa ata acc ctt gca        3159
Tyr Ser Asn Ile Met Asn Phe Phe Lys Thr Glu Ile Thr Leu Ala
    1040                1045                1050 aac ggt gaa atc aga aag cgg cct ctg att gaa aca aat ggc gag        3204
Asn Gly Glu Ile Arg Lys Arg Pro Leu Ile Glu Thr Asn Gly Glu
1055                1060                1065 acg ggc gag atc gtc tgg gac aag ggg agg gac ttc gca acg gtt        3249
Thr Gly Glu Ile Val Trp Asp Lys Gly Arg Asp Phe Ala Thr Val
    1070                1075                1080
```

-continued

| | | | | | | | | | | | | | | |
|---|---|---|---|---|---|---|---|---|---|---|---|---|---|---|
| cgc | aag | gtc | ctt | agc | atg | ccg | caa | gta | aat | ata | gtt | aag | aag | acg | 3294 |
| Arg | Lys | Val | Leu | Ser | Met | Pro | Gln | Val | Asn | Ile | Val | Lys | Lys | Thr | |
| | 1085 | | | | 1090 | | | | | 1095 | | | | | |
| gaa | gtt | cag | acc | ggc | ggc | ttt | agt | aaa | gaa | agc | ata | ctt | cct | aaa | 3339 |
| Glu | Val | Gln | Thr | Gly | Gly | Phe | Ser | Lys | Glu | Ser | Ile | Leu | Pro | Lys | |
| 1100 | | | | | 1105 | | | | | 1110 | | | | | |
| agg | aat | tcc | gac | aaa | ctg | ata | gcg | cgc | aag | aag | gac | tgg | gat | cca | 3384 |
| Arg | Asn | Ser | Asp | Lys | Leu | Ile | Ala | Arg | Lys | Lys | Asp | Trp | Asp | Pro | |
| | 1115 | | | | | 1120 | | | | | 1125 | | | | |
| aag | aag | tat | gga | gga | ttt | gac | tcc | cca | acc | gtt | gct | tat | agc | gtg | 3429 |
| Lys | Lys | Tyr | Gly | Gly | Phe | Asp | Ser | Pro | Thr | Val | Ala | Tyr | Ser | Val | |
| | | 1130 | | | | | 1135 | | | | | 1140 | | | |
| ttg | gta | gta | gcc | aag | gtg | gaa | aag | ggt | aag | tct | aag | aaa | ttg | aag | 3474 |
| Leu | Val | Val | Ala | Lys | Val | Glu | Lys | Gly | Lys | Ser | Lys | Lys | Leu | Lys | |
| 1145 | | | | | 1150 | | | | | 1155 | | | | | |
| tcg | gtg | aag | gag | ttg | ttg | ggg | ata | act | ata | atg | gag | cgg | agt | tcg | 3519 |
| Ser | Val | Lys | Glu | Leu | Leu | Gly | Ile | Thr | Ile | Met | Glu | Arg | Ser | Ser | |
| 1160 | | | | | 1165 | | | | | 1170 | | | | | |
| ttc | gag | aag | aac | cca | att | gac | ttt | ctc | gaa | gcc | aaa | ggc | tac | aag | 3564 |
| Phe | Glu | Lys | Asn | Pro | Ile | Asp | Phe | Leu | Glu | Ala | Lys | Gly | Tyr | Lys | |
| | 1175 | | | | | 1180 | | | | | 1185 | | | | |
| gag | gtc | aag | aag | gac | ctg | att | att | aag | ttg | cca | aag | tac | tcg | ctc | 3609 |
| Glu | Val | Lys | Lys | Asp | Leu | Ile | Ile | Lys | Leu | Pro | Lys | Tyr | Ser | Leu | |
| | | 1190 | | | | | 1195 | | | | | 1200 | | | |
| ttc | gaa | ctc | gag | aac | ggg | aga | aag | cgt | atg | ctg | gcg | tcg | gcg | ggc | 3654 |
| Phe | Glu | Leu | Glu | Asn | Gly | Arg | Lys | Arg | Met | Leu | Ala | Ser | Ala | Gly | |
| 1205 | | | | | 1210 | | | | | 1215 | | | | | |
| gag | ctg | cag | aaa | gga | aac | gag | ctg | gct | ttg | cca | tcg | aaa | tac | gta | 3699 |
| Glu | Leu | Gln | Lys | Gly | Asn | Glu | Leu | Ala | Leu | Pro | Ser | Lys | Tyr | Val | |
| | 1220 | | | | | 1225 | | | | | 1230 | | | | |
| aat | ttc | ctg | tac | ctc | gcc | tca | cat | tat | gag | aag | ctt | aaa | ggg | tct | 3744 |
| Asn | Phe | Leu | Tyr | Leu | Ala | Ser | His | Tyr | Glu | Lys | Leu | Lys | Gly | Ser | |
| | 1235 | | | | | 1240 | | | | | 1245 | | | | |
| cca | gaa | gac | aat | gaa | cag | aag | cag | ctg | ttt | gtt | gaa | cag | cac | aag | 3789 |
| Pro | Glu | Asp | Asn | Glu | Gln | Lys | Gln | Leu | Phe | Val | Glu | Gln | His | Lys | |
| 1250 | | | | | 1255 | | | | | 1260 | | | | | |
| cac | tac | ttg | gac | gag | att | ata | gaa | caa | atc | tcc | gag | ttc | tct | aaa | 3834 |
| His | Tyr | Leu | Asp | Glu | Ile | Ile | Glu | Gln | Ile | Ser | Glu | Phe | Ser | Lys | |
| | 1265 | | | | | 1270 | | | | | 1275 | | | | |
| cgg | gtt | atc | ctt | gca | gac | gcc | aat | ttg | gat | aag | gtc | ctc | tcg | gct | 3879 |
| Arg | Val | Ile | Leu | Ala | Asp | Ala | Asn | Leu | Asp | Lys | Val | Leu | Ser | Ala | |
| | | 1280 | | | | | 1285 | | | | | 1290 | | | |
| tat | aat | aag | cat | aga | gat | aag | cca | atc | cgg | gag | cag | gct | gaa | aat | 3924 |
| Tyr | Asn | Lys | His | Arg | Asp | Lys | Pro | Ile | Arg | Glu | Gln | Ala | Glu | Asn | |
| 1295 | | | | | 1300 | | | | | 1305 | | | | | |
| atc | ata | cac | ctc | ttt | acg | ttg | act | aat | ttg | ggt | gcg | cca | gcg | gca | 3969 |
| Ile | Ile | His | Leu | Phe | Thr | Leu | Thr | Asn | Leu | Gly | Ala | Pro | Ala | Ala | |
| | 1310 | | | | | 1315 | | | | | 1320 | | | | |
| ttc | aag | tac | ttc | gat | aca | aca | atc | gat | cgt | aag | cgc | tac | aca | agc | 4014 |
| Phe | Lys | Tyr | Phe | Asp | Thr | Thr | Ile | Asp | Arg | Lys | Arg | Tyr | Thr | Ser | |
| 1325 | | | | | 1330 | | | | | 1335 | | | | | |
| act | aag | gaa | gtc | ctg | gac | gcg | acg | ctg | ata | cac | cag | tcc | att | act | 4059 |
| Thr | Lys | Glu | Val | Leu | Asp | Ala | Thr | Leu | Ile | His | Gln | Ser | Ile | Thr | |
| | 1340 | | | | | 1345 | | | | | 1350 | | | | |
| gga | ctg | tat | gaa | acc | aga | ata | gat | ctt | agc | cag | ctc | ggc | ggt | gat | 4104 |
| Gly | Leu | Tyr | Glu | Thr | Arg | Ile | Asp | Leu | Ser | Gln | Leu | Gly | Gly | Asp | |
| | | 1355 | | | | | 1360 | | | | | 1365 | | | |

<210> SEQ ID NO 4

-continued

```
<211> LENGTH: 1367
<212> TYPE: PRT
<213> ORGANISM: Artificial Sequence
<220> FEATURE:
<221> NAME/KEY: misc_feature
<222> LOCATION: (10)..(10)
<223> OTHER INFORMATION: The 'Xaa' at location 10 stands for Asp, or
      Ala.
<220> FEATURE:
<221> NAME/KEY: misc_feature
<222> LOCATION: (840)..(840)
<223> OTHER INFORMATION: The 'Xaa' at location 840 stands for Asp, Ala,
      His, or Pro.
<220> FEATURE:
<223> OTHER INFORMATION: Synthetic Construct

<400> SEQUENCE: 4

Met Asp Lys Lys Tyr Ser Ile Gly Leu Xaa Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
```

-continued

```
                325                 330                 335
Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750
```

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Xaa Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

```
Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly
    1355                1360                1365

<210> SEQ ID NO 5
<211> LENGTH: 21
<212> TYPE: DNA
<213> ORGANISM: Artificial Sequence
<220> FEATURE:
<223> OTHER INFORMATION: Synthetic Sequence SV40-derived nuclear
      localization signal
<220> FEATURE:
<221> NAME/KEY: CDS
<222> LOCATION: (1)..(21)

<400> SEQUENCE: 5 cct aag aag aar mgk aar gtw                                         21
Pro Lys Lys Lys Xaa Lys Xaa
1               5

<210> SEQ ID NO 6
<211> LENGTH: 7
<212> TYPE: PRT
<213> ORGANISM: Artificial Sequence
<220> FEATURE:
<221> NAME/KEY: misc_feature
<222> LOCATION: (5)..(5)
<223> OTHER INFORMATION: The 'Xaa' at location 5 stands for Arg, or Ser.
<220> FEATURE:
<221> NAME/KEY: misc_feature
<222> LOCATION: (7)..(7)
<223> OTHER INFORMATION: The 'Xaa' at location 7 stands for Val.
<220> FEATURE:
<223> OTHER INFORMATION: Synthetic Construct

<400> SEQUENCE: 6

Pro Lys Lys Lys Xaa Lys Xaa
```

<210> SEQ ID NO 7
<211> LENGTH: 19
<212> TYPE: RNA
<213> ORGANISM: Francisella novicida
<220> FEATURE:
<221> NAME/KEY: misc_structure
<222> LOCATION: (1)..(19)
<223> OTHER INFORMATION: crRNA direct repeat sequence.

<400> SEQUENCE: 7
aauuucuacu guuguagau                                               19

<210> SEQ ID NO 8
<211> LENGTH: 83
<212> TYPE: DNA
<213> ORGANISM: Streptococcus pyogenes
<220> FEATURE:
<221> NAME/KEY: misc_structure
<222> LOCATION: (1)..(83)
<223> OTHER INFORMATION: tracrRNA

<400> SEQUENCE: 8
gttttagagc tagaaatagc aagttaaaat aaggctagtc cgttatcaac ttgaaaaagt    60
ggcaccgagt cggtggtgct ttt                                            83

<210> SEQ ID NO 9
<211> LENGTH: 14551
<212> TYPE: DNA
<213> ORGANISM: Artificial Sequence
<220> FEATURE:
<223> OTHER INFORMATION: Synthetic Sequence Complete nucleotide sequence
      of pRIT3-EGFP

<400> SEQUENCE: 9
agatggttgt tcaagacgat ctacgaacgc agtggcagcg ccggagagtt caagaagttc    60
tgtttcaccg tgcgcaagct gatcgggtca atgacctgc cggagtacga tttgaaggag   120 gaggcgggc aggctggccc gatcctagtc atgcgctacc gcaacctgat cgagggcgaa   180
gcatccgccg gttcctaatg tacggagcag atgctagggc aaattgccct agcagggaa   240 aaaggtcgaa aagtctcttt tcctgtggat agcacgtaca ttgggaaccc aaagccgtac   300
attgggaacc ggaacccgta cattgggaac ccaaagccgt acattgggaa ccggtcacac   360
atgtaagtga ctgatataaa agagaaaaaa ggcgattttt ccgcctaaaa ctctttaaaa   420
cttattaaaa ctcttaaaac ccgcctggcc tgtgcataac tgtctggcca gcgcacagcc   480
gaagagctgc aaaaagcgcc tacccttcgg tcgctgcgct ccctacgccc gccgcttcg   540 cgtcggccta tcgcggccgc tggccgctca aaaatggctg gcctacgcc aggcaatcta   600 ccagggcgcg acaagccgc gccgtcgcca ctcgaccgcc ggcgcccaca tcaaggcacc   660
ctgcctcgcg cgtttcggtg atgacggtga aaacctctga cacatgcagc tcccggagac   720
ggtcacagct tgtctgtaag cggatgccgg gagcagacaa gcccgtcagg gcgcgtcagc   780
gggtgttggc gggtgtcggg gcgcagccat gacccagtca cgtagcgata gcggagtgta   840
tactggctta actatgcggc atcagagcag attgtactga gagtgcacca tatgcggtgt   900
gaaataccgc acagatgcgt aaggagaaaa taccgcatca ggcgctcttc cgcttcctcg   960
ctcactgact cgctgcgctc ggtcgttcgg ctgcggcgag cggtatcagc tcactcaaag  1020
gcggtaatac ggttatccac agaatcaggg gataacgcag gaaagaacat gtgagcaaaa  1080

```
ggccagcaaa aggccaggaa ccgtaaaaag gccgcgttgc tggcgttttt ccataggctc    1140
cgccccctg  acgagcatca caaaaatcga cgctcaagtc agaggtggcg aaacccgaca    1200
ggactataaa gataccaggc gtttccccct ggaagctccc tcgtgcgctc tcctgttccg    1260
accctgccgc ttaccggata cctgtccgcc tttctccctt cgggaagcgt ggcgctttct    1320
catagctcac gctgtaggta tctcagttcg gtgtaggtcg ttcgctccaa gctgggctgt    1380
gtgcacgaac cccccgttca gcccgaccgc tgcgccttat ccggtaacta tcgtcttgag    1440
tccaacccgg taagacacga cttatcgcca ctggcagcag ccactggtaa caggattagc    1500
agagcgaggt atgtaggcgg tgctacagag ttcttgaagt ggtggcctaa ctacggctac    1560
actagaagga cagtatttgg tatctgcgct ctgctgaagc cagttacctt cggaaaaaga    1620
gttggtagct cttgatccgg caaacaaacc accgctggta gcggtggttt ttttgtttgc    1680
aagcagcaga ttacgcgcag aaaaaaagga tctcaagaag atcctttgat cttttctacg    1740
gggtctgacg ctcagtggaa cgaaaactca cgttaaggga ttttggtcat gagattatca    1800
aaaaggatct tcacctagat ccttttaaat taaaaatgaa gttttaaatc aatctaaagt    1860
atatatgagt aaacttggtc tgacagttac caatgcttaa tcagtgaggc acctatctca    1920
gcgatctgtc tatttcgttc atccatagtt gcctgactcc ccgtcgtgta gataactacg    1980
atacgggagg gcttaccatc tggccccagt gctgcaatga taccgcgaga cccacgctca    2040
ccggctccag atttatcagc aataaaccag ccagccggaa gggccgagcg cagaagtggt    2100
cctgcaactt tatccgcctc catccagtct attaattgtt gccgggaagc tagagtaagt    2160
agttcgccag ttaatagttt gcgcaacgtt gttgccattg ctacaggcat cgtggtgtca    2220
cgctcgtcgt ttggtatggc ttcattcagc tccggttccc aacgatcaag gcgagttaca    2280
tgatccccca tgttgtgcaa aaaagcggtt agctccttcg gtcctccgat cgttgtcaga    2340
agtaagttgg ccgcagtgtt atcactcatg gttatggcag cactgcataa ttctcttact    2400
gtcatgccat ccgtaagatg cttttctgtg actggtgagt actcaaccaa gtcattctga    2460
gaatagtgta tgcggcgacc gagttgctct tgcccggcgt caacacggga taataccgcg    2520
ccacatagca gaactttaaa agtgctcatc attggaaaac gttcttcggg gcgaaaactc    2580
tcaaggatct taccgctgtt gagatccagt tcgatgtaac ccactcgtgc acccaactga    2640
tcttcagcat cttttacttt caccagcgtt tctgggtgag caaaaacagg aaggcaaaat    2700
gccgcaaaaa agggaataag ggcgacacgg aaatgttgaa tactcatact cttccttttt    2760
caatattatt gaagcattta tcagggttat tgtctcatga gcggatacat atttgaatgt    2820
atttagaaaa ataaacaaat aggggttccg cgcacatttc cccgaaaagt gccacctgac    2880
gtctaagaaa ccattattat catgacatta acctataaaa ataggcgtat cacgaggccc    2940
tttcgtcttc gaataaatac ctgtgacgga agatcacttc gcagaataaa taaatcctgg    3000
tgtccctgtt gataccggga agccctgggc caacttttgg cgaaaatgag acgttgatcg    3060
gcacgtaaga ggttccaact ttcaccataa tgaaataaga tcactaccgg gcgtattttt    3120
tgagttatcg agattttcag gagctaagga agctaaaatg gagaaaaaaa tcactggata    3180
taccaccgtt gatatatccc aatggcatcg taaagaacat tttgaggcat ttcagtcagt    3240
tgctcaatgt acctataacc agaccgttcc tggatattac ggcctttta  aagaccgtaa    3300
agaaaaataa gcacaagttt tatccggcct ttattcacat tcttgcccgc ctgatgaatg    3360
ctcatccgga ataattcgaa gctcggtccc gtgggtgttc tgtcgtctcg ttgtacaacg    3420
aaatccattc ccattccgcg ctcaagatgg cttcccctcg gcagttcatc agggctaaat    3480
```

```
caatctagcc gacttgtccg gtgaaatggg ctgcactcca acagaaacaa tcaaacaaac   3540
atacacagcg acttattcac acgagctcaa attacaacgg tatatatcct gccagtcagc   3600
atcatcacac caaaagttag gcccgaatag tttgaaatta gaaagctcgc aattgaggtc   3660
tacaggccaa attcgctctt agccgtacaa tattactcac cggtgcgatg ccccccatcg   3720
taggtgaagg tggaaattaa tgatccatct tgagaccaca ggcccacaac agctaccagt   3780
ttcctcaagg gtccaccaaa aacgtaagcg cttacgtaca tggtcgataa gaaaaggcaa   3840
tttgtagatg ttaattccca tcttgaaaga aatatagttt aaatatttat tgataaaata   3900
acaagtcagg tattatagtc caagcaaaaa cataaattta ttgatgcaag tttaaattca   3960
gaaatatttc aataactgat tatatcagct ggtacattgc cgtagatgaa agactgagtg   4020
cgatattatg tgtaatacat aaattgatga tatagctagc ttagctcatc ggggatccg   4080 tcgacctgca gccaagctgg gatcccagct gggatcccag cttgtcgacg gtacccccctc   4140 tagagttcct tctagacccg atctagtaac atagatgaca ccgcgcgcga taatttatcc   4200
tagtttgcgc gctatatttt gttttctatc gcgtattaaa tgtataattg cgggactcta   4260
atcataaaaa cccatctcat aaataacgtc atgcattaca tgttaattat tacatgctta   4320
acgtaattca acagaaatta tatgataatc atcgcaagac cggcaacagg attcaatctt   4380
aagaaacttt attgccaaat gtttgaacga tcggggatca tccgggtctg tggcgggaac   4440
tccacgaaaa tatccgaacg cagcaagata tcgcggtgca tctcggtctt gcctgggcag   4500
tcgccgccga cgccgttgat gtggacgccg ggcccgatca tattgtcgct caggatcgtg   4560
gcgttgtgct tgtcggccgt tgctgtcgta atgatatcgg caccttcgac cgcctgttcc   4620
gcagagatcc cgtgggcgaa gaactccagc atgagatccc cgcgctggag gatcatccag   4680
ccggcgtccc ggaaaacgat tccgaagccc aacctttcat agaaggcggc ggtggaatcg   4740
aaatctcgtg atggcaggtt gggcgtcgct tggtcggtca tttcgaaccc cagagtcccg   4800
ctcagaagaa ctcgtcaaga aggcgataga aggcgatgcg ctgcgaatcg ggagcggcga   4860
taccgtaaag cacgaggaag cggtcagccc attcgccgcc aagctcttca gcaatatcac   4920
gggtagccaa cgctatgtcc tgatagcggt ccgccacacc cagccggcca cagtcgatga   4980
atccagaaaa gcggccattt tccaccatga tattcggcaa gcaggcatcg ccatgggtca   5040
cgacgagatc atcgccgtcg gcatgcgcg ccttgagcct ggcgaacagt tcggctggcg   5100 cgagccctg atgctcttcg tccagatcat cctgatcgac aagaccggct tccatccgag   5160
tacgtgctcg ctcgatgcga tgtttcgctt ggtggtcgaa tgggcaggta gccggatcaa   5220
gcgtatgcag ccgccgcatt gcatcagcca tgatggatac tttctcggca ggagcaaggt   5280
gagatgacag gagatcctgc cccggcactt cgcccaatag cagccagtcc cttcccgctt   5340
cagtgacaac gtcgagcaca gctgcgcaag gaacgcccgt cgtggccagc cacgatagcc   5400
gcgctgcctc gtcctgcagt tcattcaggg caccggacag gtcggtcttg acaaaaagaa   5460
ccgggcgccc ctgcgctgac agccggaaca cggcggcatc agagcagccg attgtctgtt   5520
gtgcccagtc atagccgaat agcctctcca cccaagcggc cggagaacct gcgtgcaatc   5580
catcttgttc aatcatatct cattgccccc cggtctacct acaaaaaagc tccgcacgag   5640
gctgcatttg tcacaaatca tgaaaagaaa aactaccgat gaacaatgct gagggattca   5700
aattctaccc acaaaaagaa gaaagaaaga tctagcacat ctaagcctga cgaagcagca   5760
gaaatatata aaaatataaa ccatagtgcc cttttcccct cttcctgatc ttgtttagca   5820
```

```
tggcggaaat tttaaacccc ccatcatctc ccccaacaac ggcggatcgc agatctacat    5880
ccgagagccc cattcccgc  gagatccggg ccggatccac gccggcgaga gccccagccg    5940
cgagatcccg cccctcccgc gcaccgatct gggcgcgcac gaagccgcct ctcgcccacc    6000
caaactacca aggccaaaga tcgagaccga gacggaaaaa aaaaacggag aaagaaagag    6060
gagaggggcg gggtggttac cggcgcggcg gcggcggagg gggaggggg aggagctcgt     6120 cgtccggcag cgagggggga ggaggtggag gtggtggtgg tggtggtggt agggttgggg    6180
ggatgggagg agagggggg gtatgtatat agtggcgatg ggggcgttt ctttggaagc      6240 ggagggaggg ccggcctcgt cgctggctcg cgatcctcct cgcgtttccg gcccccacga    6300
cccggaccca cctgctgttt tttctttttc ttttttttct ttcttttttt tttttggct     6360 gcgagacgtg cggtgcgtgc ggacaactca cggtgatagt ggggggtgt ggagactatt     6420 gtccagttgg ctggactggg gtgggttggg ttgggttggg ttgggctggg cttgctatgg    6480
atcgtggata gcactttggg ctttaggaac tttaggggtt gttttgtaa atgttttgag     6540 tctaagttta tcttttattt ttactagaaa aatacccat gcgctgcaac ggggaaagc      6600 tattttaatc ttattattgt tcattgtgag aattcgcctg aatatatatt tttctcaaaa    6660
attatgtcaa attagcatat gggtttttt  aaagatattt cttatacaaa tccctctgta    6720
tttacaaaag caaacgaact taaaacccga ctcaaataca gatatgcatt tccaaaagcg    6780
aataaactta aaaaccaatt catacaaaaa tgacgtatca aagtaccgac aaaaacatcc    6840
tcaattttta taatagtaga aaagagtaaa tttcactttg ggccaccttt tattaccgat    6900
attttacttt ataccacctt ttaactgatg ttttcacttt tgaccaggta atcttacctt    6960
tgttttattt tggactatcc cgactctctt ctcaagcata tgaatgaccg tatgctagtg    7020
cggccgcaag cttgactact agtctctctt aaggtagcat cacaagtttg tacaaaaaag    7080
caggctcctg caggtgagac ttttcaacaa agggtaatat cgggaaacct cctcggattc    7140
cattgcccag ctatctgtca cttcatcgaa aggacagtag aaaaggaagg tggctcctac    7200
aaatgccatc attgcgataa aggaaaggct atcgttcaag atgcctctac cgacagtggt    7260
cccaaagatg accccccacc cacgaggaac atcgtggaaa aagaagacgt tccaaccacg    7320
tcttcaaagc aagtggattg atgtgatatc tccactgacg taagggatga cgcacaatcc    7380
cactatcctt cgcaagaccc ttcctctata taaggaagtt catttcattt ggagaggaca    7440
ggcttcttga gatccttcaa caattaccaa caacaacaaa caacaaacaa cattacaatt    7500
actatttaca attacagtcg actctagagg atccatggtg agcaagggcg aggagctgtt    7560
caccggggtg gtgcccatcc tggtcgagct ggacggcgac gtaaacggcc acaagttcag    7620
cgtgtccggc gagggcgagg gcgatgccac ctacggcaag ctgaccctga agttcatctg    7680
caccaccggc aagctgcccg tgccctggcc caccctcgtg accaccttca cctacggcgt    7740
gcagtgcttc agccgctacc ccgaccacat gaagcagcac gacttcttca gtccgccat     7800 gcccgaaggc tacgtccagg agcgcaccat cttcttcaag gacgacggca actacaagac    7860
ccgcgccgag gtgaagttcg agggcgacac cctggtgaac cgcatcgagc tgaagggcat    7920
cgacttcaag gaggacggca acatcctggg gcacaagctg gagtacaact acaacagcca    7980
caacgtctat atcatggccg acaagcagaa gaacggcatc aaggtgaact tcaagatccg    8040
ccacaacatc gaggacggca gcgtgcagct cgccgaccac taccagcaga cacccccat     8100 cggcgacggc cccgtgctgc tgcccgacaa ccactacctg agcacccagt ccgccctgag    8160
caaagacccc aacgagaagc gcgatcacat ggtcctgctg gagttcgtga ccgccgccgg    8220
```

```
gatcactcac ggcatggacg agctgtacaa gtaaagcggc cgcccggctg cattcgagta   8280
ttatggcatt gggaaaactg tttttcttgt accatttgtt gtgcttgtaa tttactgtgt   8340
ttttattcg gttttcgcta tcgaactgtg aaatggaaat ggatggagaa gagttaatga    8400
atgatatggt cctttttgttc attctcaaat taatattatt tgtttttttct cttatttgtt  8460
gtgtgttgaa tttgaaatta taagagatat gcaaacattt tgttttgagt aaaaatgtgt   8520
caaatcgtgg cctctaatga ccgaagttaa tatgaggagt aaaacactag acccagcttt   8580
cttgtacaaa gtggtgatgt tgtggtcgac ccatcgatgg gcatgcaagc tgggatccca   8640
gcttggtacc agatcttata attaaatggc cttcgctgcc catattattg gtaactcaac   8700
agcatcaatc acgggatttt tctcgaatta attgcgtcga atctcagcat cgaaatattc   8760
gccttttcg tccattagac tatctattgt gatggtggat ttatcacaaa tgggacccgc    8820
cgccgacaga ggtgtgatgt taggccagga ctttgaaaat ttgcgcaact atcgtatagt   8880
ggccgacaaa ttgacgccga gttgacgac tgcctagcat ttgagtgaat tatgtaaggt    8940
aatgggctac actgaattgg tagctcaaac tgtcagtatt tatgtatatg agtgtatatt   9000
ttcgcataat ctcagaccaa tctgaagatg aaatgggtat ctgggaatgg cgaaatcaag   9060
gcatcgatcg tgaagtttct catctaagcc cccatttgga cgtgaatgta gacacgtcga   9120
aataaagatt tccgaattag aataaatttgt ttattgcttt cgcctataaa tacgacggat  9180
cgtaatttgt cgttttatca aaatgtactt tcatttata ataacgctgc ggacatctac    9240
atttttgaat tgaaaaaaaa ttggtaatta ctctttcttt ttctccatat tgaccatcat   9300
actcattgct gatccatgta gatttcccgg acatgaagcc atttacaatt gaatatatcc   9360
tgccgccgct gccgctttgc acccggtgga gcttgcatgt tggtttctac gcagaactga   9420
gccggttagg cagataattt ccattgagaa ctgagccatg tgcaccttcc ccccaacacg   9480
gtgagcgacg gggcaacgga gtgatccaca tgggacttt aaacatcatc cgtcggatgg    9540
cgttgcgaga gaagcagtcg atccgtgaga tcagccgacg caccgggcag gcgcgcaaca   9600
cgatcgcaaa gtatttgaac gcaggtacaa tcgagccgac gttcacggta ccggaacgac   9660
caagcaagct agcttagtaa agccctcgct agattttaat gcggatgttg cgattacttc   9720
gccaactatt gcgataacaa gaaaaagcca gcctttcatg atatatctcc caatttgtgt   9780
agggcttatt atgcacgctt aaaaataata aaagcagact tgacctgata gtttggctgt   9840
gagcaattat gtgcttagtg catctaacgc ttgagttaag ccgcgccgcg aagcggcgtc   9900
ggcttgaacg aattgttaga cattatttgc cgactacctt ggtgatctcg cctttcacgt   9960
agtggacaaa ttcttccaac tgatctgcgc gcgaggccaa gcgatcttct tcttgtccaa  10020
gataagcctg tctagcttca agtatgacgg gctgatactg ggccggcagg cgctccattg  10080
cccagtcggc agcgacatcc ttcggcgcga ttttgccggt tactgcgctg taccaaatgc  10140
gggacaacgt aagcactaca tttcgctcat cgccagccca gtcgggcggc gagttccata  10200
gcgttaaggt ttcatttagc gcctcaaata gatcctgttc aggaaccgga tcaaagagtt  10260
cctccgccgc tggacctacc aaggcaacgc tatgttctct tgcttttgtc agcaagatag  10320
ccagatcaat gtcgatcgtg gctggctcga agataccgct aagaatgtca ttgcgctgcc  10380
attctccaaa ttgcagttcg cgcttagctg gataacgcca cggaatgatg tcgtcgtgca  10440
caacaatggt gacttctaca gcgcggagaa tctcgctctc tccaggggaa gccgaagttt  10500
ccaaaaggtc gttgatcaaa gctcgccgcg ttgtttcatc aagccttacg gtcaccgtaa  10560
```

-continued

```
ccagcaaatc aatatcactg tgtggcttca ggccgccatc cactgcggag ccgtacaaat   10620
gtacggccag caacgtcggt tcagatggc gctcgatgac gccaactacc tctgatagtt    10680
gagtcgatac ttcggcgatc accgcttccc tcatgatgtt aactttgtt ttagggcgac    10740
tgccctgctg cgtaacatcg ttgctgctcc ataacatcaa acatcgaccc acggcgtaac   10800
gcgcttgctg cttggatgcc cgaggcatag actgtacccc aaaaaaacag tcataacaag   10860
ccatgaaaac cgccactgcg ccgttaccac cgctgcgttc ggtcaaggtt ctggaccagt    10920
tgcgtgagcg catacgctac ttgcattaca gcttacgaac cgaacaggct tatgtccact   10980
gggttcgtgc cttcatccgt ttccacggtg tgcgtcaccc gcaaccttg ggcagcagcg    11040
aagtcgaggc atttctgtcc tggctggcga acgagcgcaa ggtttcggtc tccacgcatc   11100
gtcaggcatt ggcggccttg ctgttcttct acggcaaggt gctgtgcacg gatctgccct   11160
ggcttcagga gatcggaaga cctcggccgt cgcggcgctt gccggtggtg ctgaccccgg   11220
atgaagtggt tcgcatcctc ggttttctgg aaggcgagca tcgtttgttc gcccagcttc   11280
tgtatggaac gggcatgcgg atcagtgagg gtttgcaact gcgggtcaag gatctggatt    11340
tcgatcacgg cacgatcatc gtgcgggagg gcaagggctc caaggatcgg gccttgatgt    11400
tacccgagag cttggcaccc agcctgcgcg agcaggatcg atccaacccc tccgctgcta   11460
tagtgcagtc ggcttctgac gttcagtgca gccgtcttct gaaaacgaca tgtcgcacaa   11520
gtcctaagtt acgcgacagg ctgccgccct gccctttcc tggcgttttc ttgtcgcgtg    11580
ttttagtcgc ataaagtaga atacttgcga ctagaaccgg agacattacg ccatgaacaa   11640
gagcgccgcc gctggcctgc tgggctatgc ccgcgtcagc accgacgacc aggacttgac    11700
caaccaacgg gccgaactgc acgcggccgg ctgcaccaag ctgttttccg agaagatcac    11760
cggcaccagg cgcgaccgcc cggagctggc caggatgctt gaccacctac gccctggcga   11820
cgttgtgaca gtgaccaggc tagaccgcct ggcccgcagc acccgcgacc tactggacat   11880
tgccgagcgc atccaggagg ccggcgcggg cctgcgtagc ctggcagagc cgtgggccga    11940
caccaccacg ccggccggcc gcatggtgtt gaccgtgttc gccggcattg ccgagttcga    12000
gcgttcccta atcatcgacc gcacccgag cgggcgcgag gccgccaagg cccgaggcgt     12060
gaagtttggc ccccgcccta ccctcacccc ggcacagatc gcgcacgccc gcgagctgat   12120
cgaccaggaa ggccgcaccg tgaaagaggc ggctgcactg cttggcgtgc atcgctcgac    12180
cctgtaccgc gcacttgagc gcagcgagga agtgacgccc accgaggcca ggcggcgcgg    12240
tgccttccgt gaggacgcat tgaccgaggc cgacgcccctg cgggccgccg agaatgaacg    12300
ccaagaggaa caagcatgaa accgcaccag gacggccagg acgaaccgtt tttcattacc    12360
gaagagatcg aggcggagat gatcgcggcc gggtacgtgt tcgagccgcc cgcgcacgtc   12420
tcaaccgtgc ggctgcatga atcctggcc ggtttgtctg atgccaagct ggcggcctgg     12480
ccggccagct tggccgctga agaaaccgag cgccgccgtc taaaaggtg atgtgtattt    12540
gagtaaaaca gcttgcgtca tgcggtcgct gcgtatatga tgcgatgagt aaataaacaa    12600
atacgcaagg ggaacgcatg aaggttatcg ctgtacttaa ccagaaaggc gggtcaggca   12660
agacgaccat cgcaacccat ctagcccgcg ccctgcaact cgccggggcc gatgttctgt   12720
tagtcgattc cgatccccag ggcagtgccc gcgattgggc ggccgtgcgg gaagatcaac    12780
cgctaaccgt tgtcggcatc gaccgcccga cgattgaccg cgacgtgaag gccatcggcc   12840
ggcgcgactt cgtagtgatc gacggagcgc cccaggcggc ggacttggct gtgtccgcga   12900
tcaaggcagc cgacttcgtg ctgattccgg tgcagccaag cccttacgac atatgggcca    12960
```

```
ccgccgacct ggtggagctg gttaagcagc gcattgaggt cacggatgga aggctacaag   13020
cggcctttgt cgtgtcgcgg gcgatcaaag gcacgcgcat cggcggtgag gttgccgagg   13080
cgctggccgg gtacgagctg cccattcttg agtcccgtat cacgcagcgc gtgagctacc   13140
caggcactgc cgccgccggc acaaccgttc ttgaatcaga acccgagggc gacgctgccc   13200
gcgaggtcca ggcgctggcc gctgaaatta aatcaaaact catttgagtt aatgaggtaa   13260
agagaaaatg agcaaaagca caaacacgct aagtgccggc cgtccgagcg cacgcagcag   13320
caaggctgca acgttggcca gcctggcaga cacgccagcc atgaagcggg tcaactttca   13380
gttgccggcg gaggatcaca ccaagctgaa gatgtacgcg gtacgccaag caagaccat    13440 taccgagctg ctatctgaat acatcgcgca gctaccagag taaatgagca atgaataaa    13500 tgagtagatg aattttagcg gctaaaggag gcggcatgga aaatcaagaa caaccaggca   13560
ccgacgccgt ggaatgcccc atgtgtggag gaacgggcgg ttggccaggc gtaagcggct   13620
gggttgtctg ccgccctgc aatggcactg gaaccccca gcccgaggaa tcggcgtgag     13680
cggtcgcaaa ccatccggcc cggtacaaat cggcgcggcg ctgggtgatg acctggtgga   13740
gaagttgaag gccgcgcagg ccgcccagcg gcaacgcatc gaggcagaag cacgccccgg   13800
tgaatcgtgg caagcggccg ctgatcgaat ccgcaaagaa tcccggcaac gccggcagc    13860 cggtgcgccg tcgattagga agccgcccaa gggcgacgag caaccagatt ttttcgttcc   13920
gatgctctat gacgtgggca cccgcgatag tcgcagcatc atggacgtgg ccgttttccg   13980
tctgtcgaag cgtgaccgac gagctggcga ggtgatccgc tacgagcttc cagacgggca   14040
cgtagaggtt tccgcagggc cggccggcat ggccagtgtg tgggattacg acctggtact   14100
gatggcggtt tccatctaa ccgaatccat gaaccgatac cgggaaggga agggagacaa    14160
gcccggccgc gtgttccgtc cacacgttgc ggacgtactc aagttctgcc ggcgagccga   14220
tggcggaaag cagaaagacg acctggtaga aacctgcatt cggttaaaca ccacgcacgt   14280
tgccatgcag cgtacgaaga aggccaagaa cggccgcctg gtgacggtat ccgagggtga   14340
agccttgatt agccgctaca agatcgtaaa gagcgaaacc gggcggccgg agtacatcga   14400
gatcgagcta gctgattgga tgtaccgcga gatcacagaa ggcaagaacc cggacgtgct   14460
gacggttcac cccgattact tttgatcga tcccggcatc ggccgttttc tctaccgcct    14520
ggcacgccgc gccgcaggca aggcagaagc c                                  14551
```

<210> SEQ ID NO 10
<211> LENGTH: 14569
<212> TYPE: DNA
<213> ORGANISM: Artificial Sequence
<220> FEATURE:
<223> OTHER INFORMATION: Synthetic Sequence Complete nucleotide sequence of pRIT3-mEGFP

<400> SEQUENCE: 10

```
agatggttgt tcaagacgat ctacgaacgc agtggcagcg ccggagagtt caagaagttc    60
tgtttcaccg tgcgcaagct gatcgggtca aatgacctgc cggagtacga tttgaaggag   120
gaggcggggc aggctggccc gatcctagtc atgcgctacc gcaacctgat cgagggcgaa   180
gcatccgccg gttcctaatg tacggagcag atgctagggc aaattgccct agcagggaa    240 aaaggtcgaa aagtctctt tcctgtggat agcacgtaca ttgggaaccc aaagccgtac    300
attgggaacc ggaacccgta cattgggaac ccaaagccgt acattgggaa ccggtcacac    360
atgtaagtga ctgatataaa agagaaaaaa ggcgattttt ccgcctaaaa ctctttaaaa    420
```

```
cttattaaaa ctcttaaaac ccgcctggcc tgtgcataac tgtctggcca gcgcacagcc      480
gaagagctgc aaaaagcgcc tacccttcgg tcgctgcgct ccctacgccc cgccgcttcg      540
cgtcggccta tcgcggccgc tggccgctca aaaatggctg gcctacggcc aggcaatcta      600
ccagggcgcg acaagccgc gccgtcgcca ctcgaccgcc ggcgcccaca tcaaggcacc       660
ctgcctcgcg cgtttcggtg atgacggtga aaacctctga cacatgcagc tcccggagac      720
ggtcacagct tgtctgtaag cggatgccgg gagcagacaa gcccgtcagg gcgcgtcagc      780
gggtgttggc gggtgtcggg gcgcagccat gacccagtca cgtagcgata gcggagtgta      840
tactggctta actatgcggc atcagagcag attgtactga gagtgcacca tatgcggtgt      900
gaaataccgc acagatgcgt aaggagaaaa taccgcatca ggcgctcttc cgcttcctcg      960
ctcactgact cgctgcgctc ggtcgttcgg ctgcggcgag cggtatcagc tcactcaaag     1020
gcggtaatac ggttatccac agaatcaggg gataacgcag gaaagaacat gtgagcaaaa     1080
ggccagcaaa aggccaggaa ccgtaaaaag gccgcgttgc tggcgttttt ccataggctc     1140
cgcccccctg acgagcatca caaaaatcga cgctcaagtc agaggtggcg aaacccgaca     1200
ggactataaa gataccaggc gtttccccct ggaagctccc tcgtgcgctc tcctgttccg     1260
accctgccgc ttaccggata cctgtccgcc tttctccctt cgggaagcgt ggcgctttct     1320
catagctcac gctgtaggta tctcagttcg gtgtaggtcg ttcgctccaa gctgggctgt     1380
gtgcacgaac cccccgttca gcccgaccgc tgcgccttat ccggtaacta tcgtcttgag     1440
tccaacccgg taagacacga cttatcgcca ctggcagcag ccactggtaa caggattagc     1500
agagcgaggt atgtaggcgg tgctacagag ttcttgaagt ggtggcctaa ctacggctac     1560
actagaagga cagtatttgg tatctgcgct ctgctgaagc cagttacctt cggaaaaaga     1620
gttggtagct cttgatccgg caaacaaacc accgctggta gcggtggttt ttttgtttgc     1680
aagcagcaga ttacgcgcag aaaaaaagga tctcaagaag atcctttgat cttttctacg     1740
gggtctgacg ctcagtggaa cgaaaactca cgttaaggga ttttggtcat gagattatca     1800
aaaaggatct tcacctagat ccttttaaat taaaaatgaa gttttaaatc aatctaaagt     1860
atatatgagt aaacttggtc tgacagttac caatgcttaa tcagtgaggc acctatctca     1920
gcgatctgtc tatttcgttc atccatagtt gcctgactcc ccgtcgtgta gataactacg     1980
atacgggagg gcttaccatc tggccccagt gctgcaatga taccgcgaga cccacgctca     2040
ccggctccag atttatcagc aataaaccag ccagccggaa gggccgagcg cagaagtggt     2100
cctgcaactt tatccgcctc catccagtct attaattgtt gccgggaagc tagagtaagt     2160
agttcgccag ttaatagttt gcgcaacgtt gttgccattg ctacaggcat cgtggtgtca     2220
cgctcgtcgt ttggtatggc ttcattcagc tccggttccc aacgatcaag gcgagttaca     2280
tgatccccca tgttgtgcaa aaaagcggtt agctccttcg gtcctccgat cgttgtcaga     2340
agtaagttgg ccgcagtgtt atcactcatg gttatggcag cactgcataa ttctcttact     2400
gtcatgccat ccgtaagatg cttttctgtg actggtgagt actcaaccaa gtcattctga     2460
gaatagtgta tgcggcgacc gagttgctct tgcccggcgt caacacggga taataccgcg     2520
ccacatagca gaactttaaa agtgctcatc attggaaaac gttcttcggg gcgaaaactc     2580
tcaaggatct taccgctgtt gagatccagt tcgatgtaac ccactcgtgc acccaactga     2640
tcttcagcat cttttacttt caccagcgtt tctgggtgag caaaaacagg aaggcaaaat     2700
gccgcaaaaa agggaataag ggcgacacgg aaatgttgaa tactcatact cttcctttt      2760
```

```
caatattatt gaagcattta tcagggttat tgtctcatga gcggatacat atttgaatgt    2820
atttagaaaa ataaacaaat aggggttccg cgcacatttc cccgaaaagt gccacctgac    2880
gtctaagaaa ccattattat catgacatta acctataaaa ataggcgtat cacgaggccc    2940
tttcgtcttc gaataaatac ctgtgacgga agatcacttc gcagaataaa taaatcctgg    3000
tgtccctgtt gataccggga agccctgggc caacttttgg cgaaaatgag acgttgatcg    3060
gcacgtaaga ggttccaact ttcaccataa tgaaataaga tcactaccgg gcgtattttt    3120
tgagttatcg agattttcag gagctaagga agctaaaatg gagaaaaaaa tcactggata    3180
taccaccgtt gatatatccc aatggcatcg taaagaacat tttgaggcat ttcagtcagt    3240
tgctcaatgt acctataacc agaccgttcc tggatattac ggccttttta aagaccgtaa    3300
agaaaaataa gcacaagttt tatccggcct ttattcacat tcttgcccgc ctgatgaatg    3360
ctcatccgga ataattcgaa gctcggtccc gtgggtgttc tgtcgtctcg ttgtacaacg    3420
aaatccattc ccattccgcg ctcaagatgg cttcccctcg gcagttcatc agggctaaat    3480
caatctagcc gacttgtccg gtgaaatggg ctgcactcca acagaaacaa tcaaacaaac    3540
atacacagcg acttattcac acgagctcaa attacaacgg tatatatcct gccagtcagc    3600
atcatcacac caaaagttag gcccgaatag tttgaaatta gaaagctcgc aattgaggtc    3660
tacaggccaa attcgctctt agccgtacaa tattactcac cggtgcgatg cccccccatcg   3720 taggtgaagg tggaaattaa tgatccatct tgagaccaca ggcccacaac agctaccagt    3780
ttcctcaagg gtccaccaaa aacgtaagcg cttacgtaca tggtcgataa gaaaaggcaa    3840
tttgtagatg ttaattccca tcttgaaaga aatatagttt aaatatttat tgataaaata    3900
acaagtcagg tattatagtc caagcaaaaa cataaattta ttgatgcaag tttaaattca    3960
gaaatatttc aataactgat tatatcagct ggtacattgc cgtagatgaa agactgagtg    4020
cgatattatg tgtaatacat aaattgatga tatagctagc ttagctcatc gggggatccg    4080
tcgacctgca gccaagctgg gatcccagct gggatcccag cttgtcgacg gtaccccctc    4140
tagagttcct tctagacccg atctagtaac atagatgaca ccgcgcgcga taatttatcc    4200
tagtttgcgc gctatatttt gttttctatc gcgtattaaa tgtataattg cgggactcta    4260
atcataaaaa cccatctcat aaataacgtc atgcattaca tgttaattat tacatgctta    4320
acgtaattca acagaaatta tatgataatc atcgcaagac cggcaacagg attcaatctt    4380
aagaaacttt attgccaaat gtttgaacga tcggggatca tccgggtctg tggcgggaac    4440
tccacgaaaa tatccgaacg cagcaagata tcgcggtgca tctcggtctt gcctgggcag    4500
tcgccgccga cgccgttgat gtggacgccg ggcccgatca tattgtcgct caggatcgtg    4560
gcgttgtgct tgtcggccgt tgctgtcgta atgatatcgg caccttcgac cgcctgttcc    4620
gcagagatcc cgtgggcgaa gaactccagc atgagatccc cgcgctggag gatcatccag    4680
ccggcgtccc ggaaaacgat tccgaagccc aacctttcat agaaggcggc ggtgaatcg     4740 aaatctcgtg atggcaggtt gggcgtcgct tggtcggtca tttcgaaccc cagagtcccg    4800
ctcagaagaa ctcgtcaaga aggcgataga aggcgatgcg ctgcgaatcg ggagcggcga    4860
taccgtaaag cacgaggaag cggtcagccc attcgccgcc aagctcttca gcaatatcac    4920
gggtagccaa cgctatgtcc tgatagcggt ccgccacacc cagccggcca cagtcgatga    4980
atccagaaaa gcggccattt tccaccatga tattcggcaa gcaggcatcg ccatgggtca    5040
cgacgagatc atcgccgtcg gcatgcgcg ccttgagcct ggcgaacagt tcggctggcg     5100
cgagcccctg atgctcttcg tccagatcat cctgatcgac aagaccggct tccatccgag    5160
```

```
tacgtgctcg ctcgatgcga tgtttcgctt ggtggtcgaa tgggcaggta gccggatcaa   5220
gcgtatgcag ccgccgcatt gcatcagcca tgatggatac tttctcggca ggagcaaggt   5280
gagatgacag gagatcctgc cccggcactt cgcccaatag cagccagtcc cttcccgctt   5340
cagtgacaac gtcgagcaca gctgcgcaag gaacgcccgt cgtggccagc cacgatagcc   5400
gcgctgcctc gtcctgcagt tcattcaggg caccggacag gtcggtcttg acaaaaagaa   5460
ccgggcgccc ctgcgctgac agccggaaca cggcggcatc agagcagccg attgtctgtt   5520
gtgcccagtc atagccgaat agcctctcca cccaagcggc cggagaacct gcgtgcaatc   5580
catcttgttc aatcatatct cattgccccc cggtctacct acaaaaagc tccgcacgag    5640 gctgcatttg tcacaaatca tgaaaagaaa aactaccgat gaacaatgct gagggattca   5700
aattctaccc acaaaaagaa gaaagaaaga tctagcacat ctaagcctga cgaagcagca   5760
gaaatatata aaaatataaa ccatagtgcc cttttcccct cttcctgatc ttgtttagca   5820
tggcggaaat tttaaacccc ccatcatctc ccccaacaac ggcggatcgc agatctacat   5880
ccgagagccc cattccccgc gagatccggg ccggatccac gccggcgaga gccccagccg   5940
cgagatcccg cccctcccgc gcaccgatct gggcgcgcac gaagccgcct ctcgcccacc   6000
caaactacca aggccaaaga tcgagaccga gacggaaaaa aaaaacggag aaagaaagag   6060
gagaggggcg gggtggttac cggcgcggcg gcggcggagg gggagggggg aggagctcgt   6120
cgtccggcag cgagggggga ggaggtggag gtggtggtgg tggtggtggt agggttgggg   6180
ggatgggagg agaggggggg gtatgtatat agtggcgatg gggggcgttt ctttggaagc   6240
ggagggaggg ccggcctcgt cgctggctcg cgatcctcct cgcgtttccg gccccacga    6300 cccggaccca cctgctgttt tttcttttc ttttttttct ttcttttttt tttttggct     6360 gcgagacgtg cggtgcgtgc ggacaactca cggtgatagt ggggggggtgt ggagactatt   6420 gtccagttgg ctggactggg gtgggttggg ttgggttggg ttgggctggg cttgctatgg   6480
atcgtggata gcactttggg ctttaggaac tttagggggtt gttttttgtaa atgttttgag  6540 tctaagttta tcttttatttt ttactagaaa aaatacccat gcgctgcaac ggggggaaagc  6600 tattttaatc ttattattgt tcattgtgag aattcgcctg aatatatatt tttctcaaaa   6660
attatgtcaa attagcatat gggttttttt aaagatattt cttatacaaa tccctctgta   6720
tttacaaaag caaacgaact taaaacccga ctcaaataca gatatgcatt tccaaaagcg   6780
aataaactta aaaaccaatt catacaaaaa tgacgtatca aagtaccgac aaaaacatcc   6840 tcaatttta taatagtaga aaagagtaaa tttcactttg ggccaccttt tattaccgat    6900
attttacttt ataccacctt ttaactgatg ttttcacttt tgaccaggta atcttacctt   6960
tgttttattt tggactatcc cgactctctt ctcaagcata tgaatgaccg tatgctagtg   7020
cggccgcaag cttgactact agtctctctt aaggtagcat cacaagtttg tacaaaaaag   7080
caggctcctg caggtgagac ttttcaacaa agggtaatat cggaaaacct cctcggattc   7140
cattgcccag ctatctgtca cttcatcgaa aggacagtag aaaaggaagg tggctcctac   7200
aaatgccatc attgcgataa aggaaaggct atcgttcaag atgcctctac cgacagtggt   7260
cccaaagatg gacccccacc cacgaggaac atcgtgaaa aagaagacgt tccaaccacg    7320
tcttcaaagc aagtggattg atgtgatatc tccactgacg taagggatga cgcacaatcc   7380
cactatcctt cgcaagaccc ttcctctata taaggaagtt catttcattt ggagaggaca   7440
ggcttcttga gatccttcaa caattaccaa caacaacaaa caacaaacaa cattacaatt   7500
```

```
actatttaca attacagtcg actctagagg atccggccca gttggaatgt aggtggtgag   7560
caagggcgag gagctgttca ccggggtggt gcccatcctg gtcgagctgg acggcgacgt   7620
aaacggccac aagttcagcg tgtccggcga gggcgagggc gatgccacct acggcaagct   7680
gaccctgaag ttcatctgca ccaccggcaa gctgccggtg ccctggccca ccctcgtgac   7740
caccttcacc tacggcgtgc agtgcttcag ccgctacccc gaccacatga agcagcacga   7800
cttcttcaag tccgccatgc ccgaaggcta cgtccaggag cgcaccatct tcttcaagga   7860
cgacggcaac tacaagaccc gcgccgaggt gaagttcgag ggcgacaccc tggtgaaccg   7920
catcgagctg aagggcatcg acttcaagga ggacggcaac atcctggggc acaagctgga   7980
gtacaactac aacagccaca acgtctatat catggccgac aagcagaaga acggcatcaa   8040
ggtgaacttc aagatccgcc acaacatcga ggacggcagc gtgcagctcg ccgaccacta   8100
ccagcagaac acccccatcg gcgacggccc cgtgctgctg cccgacaacc actacctgag   8160
cacccagtcc gccctgagca agacccccaa cgagaagcgc gatcacatgg tcctgctgga   8220
gttcgtgacc gccgccggga tcactcacgg catgacgagc tgtacaagt aaagcggccg   8280 cccggctgca ttcgagtatt atggcattgg gaaaactgtt ttccttgtac catttgttgt   8340
gcttgtaatt tactgtgttt tttattcggt ttcgctatc gaactgtgaa atggaaatgg   8400
atggagaaga gttaatgaat gatatggtcc ttttgttcat tctcaaatta atattatttg   8460 tttttctct tatttgttgt gtgttgaatt tgaaattata agagatatgc aaacattttg   8520
ttttgagtaa aaatgtgtca atcgtggcc tctaatgacc gaagttaata tgaggagtaa   8580
aacactagac ccagctttct tgtacaaagt ggtgatgttg tggtcgaccc atcgatgggc   8640
atgcaagctg ggatcccagc ttggtaccag atcttataat taaatggcct tcgctgccca   8700
tattattggt aactcaacag catcaatcac gggattttc tcgaattaat tgcgtcgaat   8760
ctcagcatcg aaatattcgc ctttttcgtc cattagacta tctattgtga tggtggattt   8820
atcacaaatg ggacccgccg ccgacagagg tgtgatgtta ggccaggact ttgaaaattt   8880
gcgcaactat cgtatagtgg ccgacaaatt gacgccgagt tgacagactg cctagcattt   8940
gagtgaatta tgtaaggtaa tgggctacac tgaattggta gctcaaactg tcagtattta   9000
tgtatatgag tgtatatttt cgcataatct cagaccaatc tgaagatgaa atgggtatct   9060
gggaatggcg aaatcaaggc atcgatcgtg aagtttctca tctaagcccc catttggacg   9120
tgaatgtaga cacgtcgaaa taaagatttc gaattagaa taatttgttt attgctttcg   9180
cctataaata cgacggatcg taatttgtcg ttttatcaaa atgtactttc atttttataat   9240 aacgctgcgg acatctacat ttttgaattg aaaaaaaatt ggtaattact ctttcttttt   9300
ctccatattg accatcatac tcattgctga tccatgtaga tttcccggac atgaagccat   9360
ttacaattga atatatcctg ccgccgctgc cgctttgcac ccgtggagc ttgcatgttg   9420 gtttctacgc agaactgagc cggttaggca gataatttcc attgagaact gagccatgtg   9480
caccttcccc ccaacacggt gagcgacggg gcaacggagt gatccacatg ggactttaa   9540 acatcatccg tcggatggcg ttgcgagaga agcagtcgat ccgtgagatc agccgacgca   9600
ccgggcaggc gcgcaacacg atcgcaaagt atttgaacgc aggtacaatc gagccgacgt   9660
tcacggtacc ggaacgacca agcaagctag cttagtaaag ccctcgctag attttaatgc   9720
ggatgttgcg attacttcgc caactattgc gataacaaga aaaagccagc ctttcatgat   9780
atatctccca atttgtgtag ggcttattat gcacgcttaa aaataataaa agcagacttg   9840
acctgatagt ttggctgtga gcaattatgt gcttagtgca tctaacgctt gagttaagcc   9900
```

```
gcgccgcgaa gcggcgtcgg cttgaacgaa ttgttagaca ttatttgccg actaccttgg    9960
tgatctcgcc tttcacgtag tggacaaatt cttccaactg atctgcgcgc gaggccaagc   10020
gatcttcttc ttgtccaaga taagcctgtc tagcttcaag tatgacgggc tgatactggg   10080
ccggcaggcg ctccattgcc cagtcggcag cgacatcctt cggcgcgatt ttgccggtta   10140
ctgcgctgta ccaaatgcgg gacaacgtaa gcactacatt tcgctcatcg ccagcccagt   10200
cgggcggcga gttccatagc gttaaggttt catttagcgc ctcaaataga tcctgttcag   10260
gaaccggatc aaagagttcc tccgccgctg gacctaccaa ggcaacgcta tgttctcttg   10320
cttttgtcag caagatagcc agatcaatgt cgatcgtggc tggctcgaag atacctgcaa   10380
gaatgtcatt gcgctgccat tctccaaatt gcagttcgcg cttagctgga taacgccacg   10440
gaatgatgtc gtcgtgcaca acaatggtga cttctacagc gcggagaatc tcgctctctc   10500
caggggaagc cgaagtttcc aaaaggtcgt tgatcaaagc tcgccgcgtt gtttcatcaa   10560
gccttacggt caccgtaacc agcaaatcaa tatcactgtg tggcttcagg ccgccatcca   10620
ctgcggagcc gtacaaatgt acggccagca acgtcggttc gagatggcgc tcgatgacgc   10680
caactacctc tgatagttga gtcgatactt cggcgatcac cgcttccctc atgatgttta   10740
actttgtttt agggcgactg ccctgctgcg taacatcgtt gctgctccat aacatcaaac   10800
atcgacccac ggcgtaacgc gcttgctgct tggatgcccg aggcatagac tgtaccccaa   10860
aaaaacagtc ataacaagcc atgaaaaccg ccactgcgcc gttaccaccg ctgcgttcgg   10920
tcaaggttct ggaccagttg cgtgagcgca tacgctactt gcattacagc ttacgaaccg   10980
aacaggctta tgtccactgg gttcgtgcct tcatccgttt ccacggtgtg cgtcacccgg   11040
caaccttggg cagcagcgaa gtcgaggcat ttctgtcctg gctggcgaac gagcgcaagg   11100
tttcggtctc cacgcatcgt caggcattgg cggccttgct gttcttctac ggcaaggtgc   11160
tgtgcacgga tctgccctgg cttcaggaga tcggaagacc tcggccgtcg cggcgcttgc   11220
cggtggtgct gaccccggat gaagtggttc gcatcctcgg ttttctggaa ggcgagcatc   11280
gtttgttcgc ccagcttctg tatgaacgg gcatgcggat cagtgagggt ttgcaactgc   11340
gggtcaagga tctggatttc gatcacggca cgatcatcgt gcgggagggc aagggctcca   11400
aggatcgggc cttgatgtta cccgagagct tggcacccag cctgcgcgag caggatcgat   11460
ccaacccctc cgctgctata gtgcagtcgg cttctgacgt tcagtgcagc cgtcttctga   11520
aaacgacatg tcgcacaagt cctaagttac gcgacaggct gccgccctgc ccttttcctg   11580
gcgttttctt gtcgcgtgtt ttagtcgcat aaagtagaat acttgcgact agaaccggag   11640
acattacgcc atgaacaaga gcgccgccgc tggcctgctg ggctatgccc gcgtcagcac   11700
cgacgaccag gacttgacca accaacgggc cgaactgcac gcggccggct gcaccaagct   11760
gttttccgag aagatcaccg gcaccaggcg cgaccgcccg gagctggcca ggatgcttga   11820
ccacctacgc cctggcgacg ttgtgacagt gaccaggcta gaccgcctgg cccgcagcac   11880
ccgcgaccta ctggacattg ccgagcgcat ccaggaggcc ggcgcgggcc tgcgtagcct   11940
ggcagagccg tgggccgaca ccaccacgcc ggccggccgc atggtgttga ccgtgttcgc   12000
cggcattgcc gagttcgagc gttccctaat catcgaccgc acccgagcg ggcgcgaggc   12060
cgccaaggcc cgaggcgtga agtttggccc ccgccctacc ctcaccccgg cacagatcgc   12120
gcacgcccgc gagctgatcg accaggaagg ccgcaccgtg aaagaggcgg ctgcactgct   12180
tggcgtgcat cgctcgaccc tgtaccgcgc acttgagcgc agcgaggaag tgacgcccac   12240
```

```
cgaggccagg cggcgcggtg ccttccgtga ggacgcattg accgaggccg acgccctggc   12300
ggccgccgag aatgaacgcc aagaggaaca agcatgaaac cgcaccagga cggccaggac   12360
gaaccgtttt tcattaccga agagatcgag gcggagatga tcgcggccgg gtacgtgttc   12420
gagccgcccg cgcacgtctc aaccgtgcgg ctgcatgaaa tcctggccgg tttgtctgat   12480
gccaagctgg cggcctggcc ggccagcttg gccgctgaag aaaccgagcg ccgccgtcta   12540
aaaaggtgat gtgtatttga gtaaaacagc ttgcgtcatg cggtcgctgc gtatatgatg   12600
cgatgagtaa ataaacaaat acgcaagggg aacgcatgaa ggttatcgct gtacttaacc   12660
agaaaggcgg gtcaggcaag acgaccatcg caacccatct agcccgcgcc ctgcaactcg   12720
ccggggccga tgttctgtta gtcgattccg atccccaggg cagtgcccgc gattgggcgg   12780
ccgtgcggga agatcaaccg ctaaccgttg tcggcatcga ccgcccgacg attgaccgcg   12840
acgtgaaggc catcggccgg cgcgacttcg tagtgatcga cggagcgccc caggcggcgg   12900
acttggctgt gtccgcgatc aaggcagccg acttcgtgct gattccggtg cagccaagcc   12960
cttacgacat atgggccacc gccgacctgg tggagctggt taagcagcgc attgaggtca   13020
cggatggaag gctacaagcg gcctttgtcg tgtcgcgggc gatcaaaggc acgcgcatcg   13080
gcggtgaggt tgccgaggcg ctggccgggt acgagctgcc cattcttgag tcccgtatca   13140
cgcagcgcgt gagctaccca ggcactgccg ccgccggcac aaccgttctt gaatcagaac   13200
ccgagggcga cgctgcccgc gaggtccagg cgctggccgc tgaaattaaa tcaaaactca   13260
tttgagttaa tgaggtaaag agaaaatgag caaaagcaca aacacgctaa gtgccggccg   13320
tccgagcgca cgcagcagca aggctgcaac gttggccagc ctggcagaca cgccagccat   13380
gaagcgggtc aactttcagt tgccggcgga ggatcacacc aagctgaaga tgtacgcggt   13440
acgccaaggc aagaccatta ccgagctgct atctgaatac atcgcgcagc taccagagta   13500
aatgagcaaa tgaataaatg agtagatgaa ttttagcggc taaaggaggc ggcatggaaa   13560
atcaagaaca accaggcacc gacgccgtgg aatgccccat gtgtggagga acgggcggtt   13620
ggccaggcgt aagcggctgg gttgtctgcc ggccctgcaa tggcactgga acccccaagc   13680
ccgaggaatc ggcgtgagcg gtcgcaaacc atccggcccg gtacaaatcg cgcggcgct   13740 gggtgatgac ctggtggaga agttgaaggc cgcgcaggcc gcccagcggc aacgcatcga   13800
ggcagaagca cgccccggtg aatcgtggca agcggccgct gatcgaatcc gcaaagaatc   13860
ccggcaaccg ccggcagccg gtgcgccgtc gattaggaag ccgcccaagg cgacgagca   13920 accagatttt ttcgttccga tgctctatga cgtgggcacc cgcgatagtc gcagcatcat   13980
ggacgtggcc gttttccgtc tgtcgaagcg tgaccgacga gctggcgagg tgatccgcta   14040
cgagcttcca gacgggcacg tagaggtttc gcagggccg gccggcatgg ccagtgtgtg   14100
ggattacgac ctggtactga tggcggtttc ccatctaacc gaatccatga accgataccg   14160
ggaagggaag ggagacaagc ccggccgcgt gttccgtcca cacgttgcgg acgtactcaa   14220
gttctgccgg cgagccgatg gcggaaagca gaaagacgac ctggtagaaa cctgcattcg   14280
gttaaacacc acgcacgttg ccatgcagcg tacgaagaag gccaagaacg gccgcctggt   14340
gacggtatcc gagggtgaag ccttgattag ccgctacaag atcgtaaaga gcgaaaccgg   14400
gcggccggag tacatcgaga tcgagctagc tgattggatg taccgcgaga tcacagaagg   14460
caagaacccg gacgtgctga cggttcaccc cgattacttt ttgatcgatc ccggcatcgg   14520
ccgttttctc taccgcctgg cacgccgcgc cgcaggcaag gcagaagcc                14569
```

<210> SEQ ID NO 11
<211> LENGTH: 18695
<212> TYPE: DNA
<213> ORGANISM: Artificial Sequence
<220> FEATURE:
<223> OTHER INFORMATION: Synthetic Sequence Complete nucleotide sequence of 2408

<400> SEQUENCE: 11

| | | | | | |
|---|---|---|---|---|---|
| taaacgctct | tttctcttag | gtttacccgc | caatatatcc | tgtcaaacac | tgatagttta | 60 |
| aactgaaggc | gggaaacgac | aatctgatcc | aagctcaagc | tccaatacgc | aaaccgcctc | 120 |
| tccccgcgcg | ttggccgatt | cattaatgca | gctggcacga | caggtttccc | gactggaaag | 180 |
| cgggcagtga | gcgcaacgca | attaatgtga | gttagctcac | tcattaggca | ccccaggctt | 240 |
| tacactttat | gcttccggct | cgtatgttgt | gtggaattgt | gagcggataa | caatttcaca | 300 |
| caggaaacag | ctatgaccat | gattacgaat | ttcaggtgac | tgatagtgac | ctgttcgttg | 360 |
| caacaaattg | atgagcaatg | ctttttata | atgccaactt | tgtacaaaaa | agcaggcggc | 420 |
| gcgtcctgca | ggatagggat | aacagggtaa | tggcgcgcca | agcttatcga | taccgtcgac | 480 |
| ctcgagcggc | cgccagtgtg | atggatatct | gcagaattgc | ccttcgaagg | acaaaaaaa | 540 |
| gcaccgactc | ggtgccactt | tttcaagttg | ataacgcact | agccttattt | taacttgcta | 600 |
| tttctagctc | taaaacgccc | agttggaatg | taggtgcaac | acaagcgaca | gcgcgcgggt | 660 |
| ttataagttg | gtcgcgttcg | agttagctgg | gcaatgtggt | actaaactgt | tcctcccgcc | 720 |
| tctcgcgctc | acactcgccc | tgtgggccgc | tcaccgtgca | cgtacttggg | cctcccgctc | 780 |
| ccccgcatgc | atccagccca | tcacagcgaa | gagaatcggg | cttttcttct | ccccatctcc | 840 |
| ctacacaacc | accaaataca | gccaggccgt | tggttcatga | tccaagggca | attccagcac | 900 |
| actggcggcc | gttactagtg | gatccgagct | cggtaccta | attaaattac | cctgttatcc | 960 |
| ctatcctgca | ggattaacac | ccaactttc | tatccaagct | tgccaacatg | gtggagcacg | 1020 |
| acactctcgt | ctactccaag | aatatcaaag | atacagtctc | agaagaccaa | agggctattg | 1080 |
| agactttca | acaagggta | atatcgggaa | acctcctcgg | attccattgc | ccagctatct | 1140 |
| gtcacttcat | caaaggaca | gtagaaaagg | aaggtggcac | ctacaaatgc | catcattgcg | 1200 |
| ataaaggaaa | ggctatcgtt | caagatgcct | ctgccgacag | tggtcccaaa | gatggacccc | 1260 |
| cacccacgag | gagcatcgtg | gaaaaagaag | acgttccaac | cacgtcttca | agcaagtgg | 1320 |
| attgatgtga | taacatggtg | gagcacgaca | ctctcgtcta | ctccaagaat | atcaaagata | 1380 |
| cagtctcaga | agaccaaagg | gctattgaga | cttttcaaca | aagggtaata | tcgggaaacc | 1440 |
| tcctcggatt | ccattgccca | gctatctgtc | acttcatcaa | aggacagta | gaaaaggaag | 1500 |
| gtggcaccta | caaatgccat | cattgcgata | aaggaaaggc | tatcgttcaa | gatgcctctg | 1560 |
| ccgacagtgg | tcccaaagat | ggacccccac | ccacgaggag | catcgtggaa | aaagaagacg | 1620 |
| ttccaaccac | gtcttcaaag | caagtggatt | gatgtgatat | ctccactgac | gtaagggatg | 1680 |
| acgcacaatc | ccactatcct | tcgcaagacc | cttcctctat | ataaggaagt | tcatttcatt | 1740 |
| tggagaggcc | ggtctagaga | attccaagca | acgaactgcg | agtgattcaa | gaaaaagaa | 1800 |
| aacctgagct | ttcgatctct | acggagtggt | ttcttgttct | ttgaaaaaga | ggggattac | 1860 |
| atatggctcc | taagaagaag | cggaaggttg | gtattcacgg | ggtgcctgcg | gctatggaca | 1920 |
| agaagtactc | gatcgggctg | gccatcggaa | caaattctgt | aggctgggct | gtaataaccg | 1980 |
| atgagtacaa | ggtgccctct | aaaaaattta | aggtccttgg | caatacgat | agacattcca | 2040 |
| taaagaagaa | tcttatcggt | gcgctgctct | ttgacagcgg | cgagaccgcg | gaggcgaccc | 2100 |

```
ggttgaaacg caccgcgaga cgccgttaca caaggcgtaa gaatagaatc tgttatctcc   2160
aggagatatt ctctaatgaa atggcgaagg tagacgattc cttctttcac cgtctggagg   2220
aaagttttct cgttgaggaa gataagaaac atgaaagaca cccgatcttc ggaaacattg   2280
tcgacgaggt cgcttatcat gaaaagtacc ctaccatcta ccatcttaga aagaaacttg   2340
ttgacagcac ggataaggct gatctcaggc tgatatacct ggctctggca catatgatta   2400
agttcagagg gcatttcctt atcgaaggcg acctgaatcc agataattca gatgtagaca   2460
agctcttcat tcaacttgtg cagacttata atcagctctt cgaagaaaat ccaataaacg   2520
cgtcgggtgt agacgcaaag gccatactgt ccgctaggct ttctaagtca cgtagacttg   2580
agaatctcat tgcccaactc cccggcgaga agaagaacgg cttgtttgga atctgatag   2640 cgctgtccct gggtcttaca ccaaatttca agagtaattt cgatttggca gaagatgcta   2700
agttgcagct cagtaaagac acctacgatg acgatcttga taatttgttg gctcagattg   2760
gcgatcagta tgcagatctt ttcttggccg ctaagaattt gtctgatgca attctgctta   2820
gcgacatttt gagggttaat acagaaatca ccaaggcacc cttgtcggcg tcaatgataa   2880
agaggtatga tgagcaccac caagacctga cgctcctcaa ggctcttgtt cggcagcaat   2940
tgccggagaa gtacaaagag atcttcttcg accagtctaa gaacggatat gcgggctaca   3000
tagacggtgg agcgagtcag gaggaattct acaagttcat aaagcccatt ctcgagaaga   3060
tggatggtac ggaagaactg cttgtgaaac ttaacagaga agatcttttg cggaagcaga   3120
gaactttcga caacggaagt ataccacacc agatacatct cggagagctt catgctattc   3180
tcagaagaca agaggatttc taccctttct tgaaggataa cagagaaaag atagagaaga   3240
tcctcacgtt taggatccct tactacgtag gtcctcttgc tcgcggcaat agtaggttcg   3300
cctggatgac ccgcaagtct gaagaaacta tcaccccttg gaatttcgaa gaggttgtag   3360
acaaaggtgc ttcagcacag agtttcattg agaggatgac caacttcgac aagaacctcc   3420
ccaacgaaaa ggtcctgcct aagcacagcc tcctctacga atactttact gtctataatg   3480
agcttacaaa agttaagtac gtgacagagg gaatgcggaa gcccgcattc ctttccggag   3540
aacaaaagaa ggcgatcgtg gatcttctct tcaagacgaa ccgcaaggtg acggttaaac   3600
agttgaagga agattacttc aagaagatag aatgttttga tagcgtggaa atcagcggcg   3660
tcgaagatag gttcaacgct tccctgggaa cgtaccacga tctcctcaag attatcaaag   3720
ataaggactt tcttgataac gaagagaatg aggacatctt ggaagacatt gttctgacgc   3780
tcaccctgtt cgaagatcgc gagatgattg aggaacgctt gaagacctac gcacacctgt   3840
tcgatgacaa ggttatgaag caacttaaac ggcgccggta tacgggctgg gacggctttt   3900
cgcggaagct gataaatgga atccgtgaca agcagtctgg caagacaata ctcgacttct   3960
tgaagtcgga tggttttgcc aatagaaatt ttatgcaact cattcatgat gactcgctta   4020
cttttaagga ggacatccag aaggcccagg tatcaggaca gggtgactct ttgcacgaac   4080
acatcgcgaa cctggcgggc tcccccgcga ttaagaaggg aatttttgcag actgtcaagg   4140 tggtcgatga actcgtgaag gttatgggac gtcataagcc ggaaaatatt gtgattgaga   4200
tggctcgcga gaatcaaaca acacagaagg gccaaaagaa cagtagagaa cgcatgaagc   4260
gcatcgaaga gggcatcaaa gagctgggca gtcagatcct taaagaacat ccagtcgaga   4320
atacacagct tcagaacgaa aagctgtacc tttattacct tcaaaatggg cgtgatatgt   4380
atgtggatca ggaactcgat atcaataggc tgagtgacta tgatgtcgac gctatcgtcc   4440
```

```
cgcaaagttt cctcaaggac gacagtatag acaacaaagt tctcacacgg tcagataaga    4500
atcgcggcaa gagcgataat gtaccgtcgg aggaggtagt caagaagatg aagaattact    4560
ggcgccagtt gctcaacgcc aagctcatca ctcagaggaa atttgacaac cttacgaaag    4620
ccgagcgggg cggactctct gaactggaca aggccggttt cataaagcgc cagctcgttg    4680
agacacgtca aattactaag cacgtcgctc aaatattgga ttcccgcatg aatactaagt    4740
acgatgagaa tgataagctc atacgtgaag ttaaggtcat tactctcaag tccaagcttg    4800
tatcggactt ccgtaaggac ttccaattct acaaggtccg ggaaatcaat aattatcacc    4860
atgcccatga cgcttatctg aacgcggtcg tgggcacggc actcattaag aaataccccaa   4920 aacttgagtc agaatttgtt tacggggact ataaagttta tgacgtgcgg aagatgatag    4980
cgaagtcgga acaagagata ggaaaggcga ctgcaaagta cttttttttac tccaacataa    5040 tgaatttctt taagaccgaa ataacccttg caaacggtga aatcagaaag cggcctctga    5100
ttgaaacaaa tggcgagacg ggcgagatcg tctgggacaa ggggagggac ttcgcaacgg    5160
ttcgcaaggt ccttagcatg ccgcaagtaa atatagttaa gaagacggaa gttcagaccg    5220
gcggctttag taaagaaagc atacttccta aaaggaattc cgacaaactg atagcgcgca    5280
agaaggactg ggatccaaag aagtatggag gatttgactc cccaaccgtt gcttatagcg    5340
tgttggtagt agccaaggtg gaaaagggta agtctaagaa attgaagtcg gtgaaggagt    5400
tgttggggat aactataatg gagcggagtt cgttcgagaa gaacccaatt gactttctcg    5460
aagccaaagg ctacaaggag gtcaagaagg acctgattat taagttgcca aagtactcgc    5520
tcttcgaact cgagaacggg agaaagcgta tgctggcgtc ggcgggcgag ctgcagaaag    5580
gaaacgagct ggctttgcca tcgaaatacg taaatttcct gtacctcgcc tcacattatg    5640
agaagcttaa agggtctcca gaagacaatg aacagaagca gctgtttgtt gaacagcaca    5700
agcactactt ggacgagatt atagaacaaa tctccgagtt ctctaaacgg ttatccttg    5760 cagacgccaa tttggataag gtcctctcgg cttataataa gcatagagat aagccaatcc    5820
gggagcaggc tgaaaatatc atacacctct ttacgttgac taatttgggt gcgccagcgg    5880
cattcaagta cttcgataca acaatcgatc gtaagcgcta cacaagcact aaggaagtcc    5940
tggacgcgac gctgatacac cagtccatta ctggactgta tgaaaccaga atagatctta    6000
gccagctcgg cggtgatgga ggagggccta gggctgatcc taagaagaag aggaaggttg    6060
gaggagggcc aggagcagag tatgttagag cgttgtttga ttttaacggt aacgatgaag    6120
aggatttacc ctttaagaaa ggcgacattc tcaggattag ggataaacct gaagagcaat    6180
ggtggaatgc tgaggatagt gaaggcaaac gaggaatgat tttagtgccg tatgtggaga    6240
aatattcggg tgactacaaa gatcatgatg gtgattacaa agaccatgac atcgactaca    6300
aggatgatga tgataagtca gggatgacag atgctgaata tgtcagaatc cacgaaaagt    6360
tggacattta cacgtttaag aagcagttct caacaacaa gaaatctgtt tcgcataggt    6420
gctatgtgct tttcgaacta aaacgtcgtg gagaaagacg gcttgctttt ggggttacg    6480 cggttaacaa accacaatca ggtactgaac gaggaataca cgctgaaatc ttttctatcc    6540
gaaaggttga ggaatatcta cgtgacaatc ctggacagtt cactatcaat ggtattcta    6600 gctggtcacc atgtgcagat tgtgctgaga agattctcga atggtacaat caagagctta    6660
gaggcaatgg acatacattg aaaatatggg catgcaagct ctactacgaa aagaatgcca    6720
gaaaccaaat tgggctttgg aacttgaggg ataatgagt tgggcttaat gtcatggttt    6780
ctgagcacta tcaatgttgt cggaagatct tcatacaaag ttcccataac cagttgaatg    6840
```

```
agaacagatg gttagagaaa acccttaaaa gagccgagaa gagaagatcc gaactgagca    6900
ttatgataca ggtcaaaatt ctgcatacca ctaagagtcc agctgtaggt cctaagaaga    6960
aacgtaaagt agggccctga tccaggcctc ccagctttcg tccgtatcat cggtttcgac    7020
aacgttcgtc aagttcaatg catcagtttc attgcccaca caccagaatc ctactaagtt    7080
tgagtattat ggcattggaa aagctgtttt cttctatcat ttgttctgct tgtaatttac    7140
tgtgttcttt cagttttgt tttcggacat caaaatgcaa atggatggat aagagttaat     7200
aaatgatatg gtccttttgt tcattctcaa attattatta tctgttgttt ttactttaat    7260
gggttgaatt taagtaagaa aggaactaac agtgtgtatat taaggtgcaa tgttagacat    7320
ataaaacagt ctttcacctc tctttggtta tgtcttgaat tggtttgttt cttcacttat    7380
ctgtgtaatc aagtttacta tgagtctatg atcaagtaat tatgcaatca agttaagtac    7440
agtataggct tgagctccct aggcccctag gtaattcttc ggacccaaga atgctaagcc    7500
aagaggagct gttatcgccg tcctcctgct tgtttctctc tttttgttgc tgtttcttca    7560
ttagcgtgga caaagttttc aaccggccta tctgttatca ttttcttcta ttcaaagact    7620
gtaataccta ttgctacctg tggttctcac ttgtgatttt ggacacatat gttcggttta    7680
ttcaaattta atcagatgcc tgatgagggt accagaaaaa atacgtgttc tggttgtttt    7740
tgagttgcga ttattctatg aaatgaataa catcgaagtt atcatcccag tattttcgca    7800
tgaatgttct tttcttctgt cttgtgcatc agtgatctag tgcatgggag tttgtattgt    7860
gatgttcgac atcacgtaac ttccactttg cctttgctgt tcgatatttt aatgacatgt    7920
cacacacact tctgatactt ttcttctg gctattgtgc cagcatgatg caagatgcat       7980
cacagcatca gatatattct catcgtcagg ctttagcagc acacgagcac gctttgccgc    8040
ttaaaagttg tacggcgcag cttagacatc ccctgtagaa gtgataatct tttcactttt    8100
ccttaaacaa attgagaggg gaaatggaac catgtggatc agagaagctt ttgtttcttt    8160
acacaagaat atttggtaca gtgggggtcc tatgttcgtg ggttcgtggc ttggctgcct    8220
gtcttcaacc aagtgttttc agttcaacat gttagcgtgt agaaagagca caattctgtt    8280
tatctccaag gtaaaatgtg gcattctgtt aaagaacatg atcctgccaa tttttaagt    8340
ttcaatggaa gaggaatgta agctttcta tggtttgtgt acacaacaca gtggaagagg     8400
agtgcaagct ttctatggtt tgtgtgcgcg ttgtgtgtca gcacttcaat tttgttagaa    8460
aatgaaagaa aaaaaggat gatcatgctt atagtaaatc actctttttc ctcgccttct     8520
gtacgttttg acttgacaag attttaaaat ctgtacatga cctttgtttt aaaattactt    8580
tatgtatttc catctttcaa gttatgcaga tgtcatcaca aattgttaca ccaatcacca    8640
ggctggctgt ttatatatta tcagaccagg ctatatagag tatactatac taactgttca    8700
tattatctgg aaatcttgct tgctacttga gcggtaaaag ggtatagata tgagggtccc    8760
cagattagcc ttttcaattt cagaaagaat gctaacccac agatggttag agaggcttac    8820
gcagcaggtc tcatcaagac gatctacccg agcaataatc tccaggaaat caaataccctt   8880
cccaagaagg ttaaagatgc agtcaaaaga ttcaggacta actgcatcaa gaacacagag    8940
aaagatatat ttctcaagat cagaagtact attccagtat ggacgattca aggcttgctt    9000
cacaaaccaa ggcaagtaat agagattgga gtctctaaaa aggtagttcc cactgaatca    9060
aaggccatgg agtcaaagat tcaaatagag gacctaacag aactcgccgt aaagactggc    9120
gaacagttca tacagagtct cttacgactc aatgacaaga agaaaatctt cgtcaacatg    9180
```

```
gtggagcacg acacacttgt ctactccaaa aatatcaaag atacagtctc agaagaccaa    9240
agggcaattg agacttttca acaaagggta atatccggaa acctcctcgg attccattgc    9300
ccagctatct gtcactttat tgtgaagata gtggaaaagg aaggtggctc ctacaaatgc    9360
catcattgcg ataaaggaaa ggccatcgtt gaagatgcct ctgccgacag tggtcccaaa    9420
gatggacccc cacccacgag gagcatcgtg aaaaagaag acgttccaac cacgtcttca     9480
aagcaagtgg attgatgtga tatctccact gacgtaaggg atgacgcaca atcccactat    9540
ccttcgcaag acccttcctc tatataagga agttcatttc atttggagag aacacggggg    9600
actctagaat gaaaaagcct gaactcaccg cgacgtctgt cgagaagttt ctgatcgaaa    9660
agttcgacag cgtctccgac ctgatgcagc tctcggaggg cgaagaatct cgtgctttca    9720
gcttcgatgt aggagggcgt ggatatgtcc tgcgggtaaa tagctgcgcc gatggttct     9780 acaaagatcg ttatgtttat cggcactttg catcggccgc gctcccgatt ccggaagtgc    9840
ttgacattgg ggagtttagc gagagcctga cctattgcat ctcccgccgt tcacagggtg    9900
tcacgttgca agacctgcct gaaaccgaac tgcccgctgt tctacaaccg gtcgcggagg    9960
ctatggatgc gatcgctgcg gccgatctta gccagacgag cgggttcggc ccattcggac    10020
cgcaaggaat cggtcaatac actacatggc gtgatttcat atgcgcgatt gctgatcccc    10080
atgtgtatca ctggcaaact gtgatggacg acaccgtcag tgcgtccgtc gcgcaggctc    10140
tcgatgagct gatgctttgg gccgaggact gccccgaagt ccggcacctc gtgcacgcgg    10200
atttcggctc caacaatgtc ctgacggaca atggccgcat aacagcggtc attgactgga    10260
gcgaggcgat gttcggggat cccaatacg aggtcgccaa catcttcttc tggaggccgt     10320
ggttggcttg tatggagcag cagacgcgct acttcgagcg gaggcatccg gagcttgcag    10380
gatcgccacg actccgggcg tatatgctcc gcattggtct tgaccaactc tatcagagct    10440
tggttgacgg caatttcgat gatgcagctt gggcgcaggg tcgatgcgac gcaatcgtcc    10500
gatccggagc cgggactgtc gggcgtacac aaatcgcccg cagaagcgcg gccgtctgga    10560
ccgatggctg tgtagaagta ctcgccgata gtggaaaccg acgccccagc actcgtccga    10620
gggcaaagaa ataggagctc tgggctaatc taaaacgatt tatctgtggc ttcaagtgta    10680
tcgatcactt atgtgaggtg taattactgg tgtttttggt gtgctctggt tcctttcaag    10740
tgtgttgttg ccgctcgaac tactccgcta tgtaaacgg taaaacctgt tgtctcatta     10800
tgaaagtgaa ctatattatg ttctactact actctactta gtcaatttc ttcaccttga     10860 ttagtgtaaa tatgaatctt atattcttat gtcttaagaa attagcacat gtgaagcctc    10920
caagtgcata ttttctcgat cgcgagacgc acaatgcgtg agaaattcag ctggttatac    10980
tcaaatatat taatatatct agcagcagct catggagatt caggaaactt ggcatcccta    11040
atccctacca tttccattct tccgagattg acagttcaat acaagtacag taatctcctg    11100
gtaagtttct tattaacttg acatgtagta gtaataattt gtacgtagca tagatacata    11160
gacacaaaaa tgtcctcccc attgagctag ccgattggag ccgaacaccg caggaatgaa    11220
tttacataat ctgcaaagaa taaatggaat gtgcctccac aggaaaacca gcggcagtgt    11280
ggcgttttca agagcagccg taagtcgaag cctattctga atcgtagaaa tcactggggc    11340
atggtgtaat tacatccgac tccaacatct gtaccaccct gtgcattgta ggccgctcct    11400
ctggcaaaga acttacacat tgtttagcaa gagaaagtag agcatccaag gtctcaatct    11460
gcactccctc acaatatgga tcgacaattt ccctctcccg attctcaccg accaggaaat    11520
tcaactgcca cagagcaagt agattatttc aagaatacat taaatcaatt gaaggcatac    11580
```

```
gtaattcata tcagaaaact gtggatatga aatggaagga cataaaggtc atacataccc    11640
atccaacaat gttcaatccc ttttcaataa atgatgcatc agtaggtcgt tttccgctta    11700
gtatttcaag tagcaaaact ccaaaactgt agacgtcagt cttttcggtg gctctgccac    11760
tttgcatata ctcctgcagg tcgaccatag tgactggata tgttgtgttt acagtatta    11820 tgtagtctgt tttttatgca aaatctaatt taatatattg atatttatat cattttacgt    11880
ttctcgttca gctttcttgt acaaagtggt gatatcccgc ggaaatacgt agaattcggg    11940
aagcttggca ctggccgtcg ttttacaacg tcgtgactgg gaaaaccctg gcgttaccca    12000
acttaatcgc cttgcagcac atcccccttt cgccagctgg cgtaatagcg aagaggcccg    12060
caccgatcgc ccttcccaac agttgcgcag cctgaatggc gaatgctaga gcaattcggc    12120
gttaattcag tacattaaaa acgtccgcaa tgtgttatta agttgtctaa gcgtcaattt    12180
gtttacacca caatatatcc tgccaccagc cagccaacag ctccccgacc ggcagctcgg    12240
cacaaaatca ccactcgata caggcagccc atcagtccgg gacggcgtca gcgggagagc    12300
cgttgtaagg cggcagactt tgctcatgtt accgatgcta ttcggaagaa cggcaactaa    12360
gctgccgggt ttgaaacacg gatgatctcg cggagggtag catgttgatt gtaacgatga    12420
cagagcgttg ctgcctgtga tcaattcggg cacgaaccca gtggacataa gcctcgttcg    12480
gttcgtaagc tgtaatgcaa gtagcgtaac tgccgtcacg caactggtcc agaaccttga    12540
ccgaacgcag cggtggtaac ggcgcagtgg cggttttcat ggcttcttgt tatgacatgt    12600
ttttttgggg tacagtctat gcctcgggca tccaagcagc aagcgcgtta cgccgtgggt    12660
cgatgtttga tgttatggag cagcaacgat gttacgcagc agggcagtcg ccctaaaaca    12720
aagttaaaca tcatggggga agcggtgatc gccgaagtat cgactcaact atcagaggta    12780
gttggcgtca tcgagcgcca tctcgaaccg acgttgctgg ccgtacattt gtacggctcc    12840
gcagtggatg gcggcctgaa gccacacagt gatattgatt tgctggttac ggtgaccgta    12900
aggcttgatg aaacaacgcg gcgagctttg atcaacgacc ttttggaaac ttcggcttcc    12960
cctggagaga gcgagattct ccgcgctgta gaagtcacca ttgttgtgca cgacgacatc    13020
attccgtggc gttatccagc taagcgcgaa ctgcaatttg gagaatggca gcgcaatgac    13080
attcttgcag gtatcttcga gccagccacg atcgacattg atctggctat cttgctgaca    13140
aaagcaagag aacatagcgt tgccttggta ggtccagcgg cggaggaact ctttgatccg    13200
gttcctgaac aggatctatt tgaggcgcta aatgaaacct taacgctatg gaactcgccg    13260
cccgactggg ctggcgatga gcgaaatgta gtgcttacgt tgtcccgcat ttggtacagc    13320
gcagtaaccg gcaaaatcgc gccgaaggat gtcgctgccg actgggcaat ggagcgcctg    13380
ccggcccagt atcagcccgt catacttgaa gctagacagg cttatcttgg acaagaagaa    13440
gatcgcttgg cctcgcgcgc agatcagttg gaagaatttg tccactacgt gaaaggcgag    13500
atcaccaagg tagtcggcaa ataatgtcta gctagaaatt cgttcaagcc gacgccgctt    13560
cgccggcgtt aaatcaagcg attagatgca ctaagcacat aattgctcac agccaaacta    13620
tcaggtcaag tctgctttta ttatttttaa gcgtgcataa taagccctac acaaattggg    13680
agatatatca tgcatgacca aaatccctta acgtgagttt tcgttccact gagcgtcaga    13740
ccccgtagaa aagatcaaag gatcttcttg agatcctttt tttctgcgcg taatctgctg    13800
cttgcaaaca aaaaaaccac cgctaccagc ggtggtttgt ttgccggatc aagagctacc    13860
aactcttttt ccgaaggtaa ctggcttcag cagagcgcag ataccaaata ctgtccttct    13920
```

```
agtgtagccg tagttaggcc accacttcaa gaactctgta gcaccgccta catacctcgc    13980
tctgctaatc ctgttaccag tggctgctgc cagtggcgat aagtcgtgtc ttaccgggtt    14040
ggactcaaga cgatagttac cggataaggc gcagcggtcg ggctgaacgg ggggttcgtg    14100
cacacagccc agcttggagc gaacgaccta caccgaactg agatacctac agcgtgagct    14160
atgagaaagc gccacgcttc ccgaagggag aaaggcggac aggtatccgg taagcggcag    14220
ggtcggaaca ggagagcgca cgagggagct tccaggggga aacgcctggt atctttatag    14280
tcctgtcggg tttcgccacc tctgacttga gcgtcgattt ttgtgatgct cgtcaggggg    14340
gcggagccta tggaaaaacg ccagcaacgc ggcctttta cggttcctgg cctttttgctg    14400 gccttttgct cacatgttct ttcctgcgtt atcccctgat tctgtggata accgtattac    14460
cgcctttgag tgagctgata ccgctcgccg cagccgaacg accgagcgca gcgagtcagt    14520
gagcgaggaa gcggaagagc gcctgatgcg gtattttctc cttacgcatc tgtgcggtat    14580
ttcacaccgc atatggtgca ctctcagtac aatctgctct gatgccgcat agttaagcca    14640
gtatacactc cgctatcgct acgtgactgg gtcatggctg cgccccgaca cccgccaaca    14700
cccgctgacg cgccctgacg ggcttgtctg ctcccggcat ccgcttacag acaagctgtg    14760
accgtctccg ggagctgcat gtgtcagagg ttttcaccgt catcaccgaa acgcgcgagg    14820
cagggtgcct tgatgtgggc gccggcggtc gagtggcgac ggcgcggctt gtccgcgccc    14880
tggtagattg cctggccgta ggccagccat ttttgagcgg ccagcggccg cgataggccg    14940
acgcgaagcg gcggggcgta gggagcgcag cgaccgaagg gtaggcgctt tttgcagctc    15000
ttcggctgtg cgctggccag acagttatgc acaggccagg cgggttttaa gagttttaat    15060 aagtttaaa gagttttagg cggaaaaatc gcctttttc tcttttatat cagtcactta    15120
catgtgtgac cggttcccaa tgtacggctt tgggttccca atgtacgggt tccgttccc    15180 aatgtacggc tttgggttcc caatgtacgt gctatccaca ggaaagagac cttttcgacc    15240
tttttcccct gctagggcaa tttgccctag catctgctcc gtacattagg aaccggcgga    15300
tgcttcgccc tcgatcaggt tgcggtagcg catgactagg atcgggccag cctgccccgc    15360
ctcctccttc aaatcgtact ccggcaggtc atttgacccg atcagcttgc gcacggtgaa    15420
acagaacttc ttgaactctc cggcgctgcc actgcgttcg tagatcgtct tgaacaacca    15480
tctggcttct gccttgcctg cggcgcgcg tgccaggcgg tagagaaaac ggccgatgcc    15540
gggatcgatc aaaaagtaat cggggtgaac cgtcagcacg tccgggttct tgccttctgt    15600
gatctcgcgg tacatccaat cagctagctc gatctcgatg tactccggcc gcccggtttc    15660
gctctttacg atcttgtagc ggctaatcaa ggcttcaccc tcggataccg tcaccaggcg    15720
gccgttcttg gccttcttcg tacgctgcat ggcaacgtgc gtggtgttta accgaatgca    15780
ggtttctacc aggtcgtctt tctgctttcc gccatcggct cgccggcaga acttgagtac    15840
gtccgcaacg tgtggacgga acacgcggcc gggcttgtct ccttccctt cccgtatcg    15900 gttcatggat tcggttagat gggaaaccgc catcagtacc aggtcgtaat cccacacact    15960
ggccatgccg gccggccctg cggaaacctc tacgtgcccg tctggaagct cgtagcggat    16020
cacctcgcca gctcgtcggt cacgcttcga cagacgaaa acggccacgt ccatgatgct    16080
gcgactatcg cgggtgccca cgtcatagag catcggaacg aaaaaatctg gttgctcgtc    16140
gcccttgggc ggcttcctaa tcgacggcgc accggctgcc ggcggttgcc gggattcttt    16200
gcggattcga tcagcggccg cttgccacga ttcaccgggg cgtgcttctg cctcgatgcg    16260
ttgccgctgg gcggcctgcg cggccttcaa cttctccacc aggtcatcac ccagcgccgc    16320
```

```
gccgatttgt accgggccgg atggtttgcg accgtcacgc cgattcctcg ggcttggggg   16380
ttccagtgcc attgcagggc cggcagacaa cccagccgct tacgcctggc caaccgcccg   16440
ttcctccaca catggggcat tccacggcgt cggtgcctgg ttgttcttga ttttccatgc   16500
cgcctccttt agccgctaaa attcatctac tcatttattc atttgctcat ttactctggt   16560
agctgcgcga tgtattcaga tagcagctcg gtaatggtct tgccttggcg taccgcgtac   16620
atcttcagct tggtgtgatc ctccgccggc aactgaaagt tgacccgctt catggctggc   16680
gtgtctgcca ggctggccaa cgttgcagcc ttgctgctgc gtgcgctcgg acggccggca   16740
cttagcgtgt ttgtgctttt gctcattttc tctttacctc attaactcaa atgagttttg   16800
atttaatttc agcggccagc gcctggacct cgcgggcagc gtcgccctcg ggttctgatt   16860
caagaacggt tgtgccggcg gcggcagtgc ctgggtagct cacgcgctgc gtgatacggg   16920
actcaagaat gggcagctcg taccggcca gcgcctcggc aacctcaccg ccgatgcgcg   16980
tgcctttgat cgcccgcgac acgacaaagg ccgcttgtag ccttccatcc gtgacctcaa   17040
tgcgctgctt aaccagctcc accaggtcgg cggtggccca tatgtcgtaa gggcttggct   17100
gcaccggaat cagcacgaag tcggctgcct tgatcgcgga cacagccaag tccgccgcct   17160
ggggcgctcc gtcgatcact acgaagtcgc gccggccgat ggccttcacg tcgcggtcaa   17220
tcgtcgggcg gtcgatgccg acaacggtta gcggttgatc ttcccgcacg gccgcccaat   17280
cgcgggcact gccctgggga tcggaatcga ctaacagaac atcggcccg gcgagttgca   17340 gggcgcgggc tagatgggtt gcgatggtcg tcttgcctga cccgcctttc tggttaagta   17400
cagcgataac cttcatgcgt tccccttgcg tatttgttta tttactcatc gcatcatata   17460
cgcagcgacc gcatgacgca agctgtttta ctcaaataca catcacctt ttagacggcg   17520 gcgctcggtt tcttcagcgg ccaagctggc cggccaggcc gccagcttgg catcagacaa   17580
accggccagg atttcatgca gccgcacggt tgagacgtgc gcgggcggct cgaacacgta   17640
cccggccgcg atcatctccg cctcgatctc ttcggtaatg aaaaacggtt cgtcctggcc   17700
gtcctggtgc ggtttcatgc ttgttcctct tggcgttcat tctcggcggc cgccagggcg   17760
tcggcctcgg tcaatgcgtc ctcacggaag gcaccgcgcc gcctggcctc ggtgggcgtc   17820
acttcctcgc tgcgctcaag tgcgcggtac agggtcgagc gatgcacgcc aagcagtgca   17880
gccgcctctt tcacggtgcg gccttcctgg tcgatcagct cgcgggcgtg cgcgatctgt   17940
gccggggtga gggtagggcg ggggccaaac ttcacgcctc gggccttggc ggcctcgcgc   18000
ccgctccggg tgcggtcgat gattagggaa cgctcgaact cggcaatgcc ggcgaacacg   18060
gtcaacacca tgcggccggc cggcgtggtg gtgtcggccc acggctctgc caggctacgc   18120
aggcccgcgc cggcctcctg gatgcgctcg gcaatgtcca gtaggtcgcg ggtgctgcgg   18180
gccaggcggt ctagcctggt cactgtcaca acgtcgccag ggcgtaggtg gtcaagcatc   18240
ctggccagct ccgggcggtc gcgcctggtg ccggtgatct tctcggaaaa cagcttggtg   18300
cagccggccg cgtgcagttc ggcccgttgg ttggtcaagt cctggtcgtc ggtgctgacg   18360
cgggcatagc ccagcaggcc agcggcggcg ctcttgttca tggcgtaatg tctccggttc   18420
tagtcgcaag tattctactt tatgcgacta aaacacgcga caagaaaacg ccaggaaaag   18480
ggcagggcgg cagcctgtcg cgtaacttag gacttgtgcg acatgtcgtt ttcagaagac   18540
ggctgcactg aacgtcagaa gccgactgca ctatagcagc ggaggggttg gatcaaagta   18600
ctttgatccc gagggggaacc ctgtggttgg catgcacata caaatggacg aacggataaa   18660
``` cctttcacg ccctttaaa tatccgttat tctaa          18695

<210> SEQ ID NO 12
<211> LENGTH: 18695
<212> TYPE: DNA
<213> ORGANISM: Artificial Sequence
<220> FEATURE:
<223> OTHER INFORMATION: Synthetic Sequence Complete nucleotide sequence
      of 2409

<400> SEQUENCE: 12

```
taaacgctct tttctcttag gtttacccgc caatatatcc tgtcaaacac tgatagttta    60
aactgaaggc gggaaacgac aatctgatcc aagctcaagc tccaatacgc aaaccgcctc   120
tccccgcgcg ttggccgatt cattaatgca gctggcacga caggtttccc gactggaaag   180
cgggcagtga gcgcaacgca attaatgtga gttagctcac tcattaggca ccccaggctt   240
tacactttat gcttccggct cgtatgttgt gtggaattgt gagcggataa caatttcaca   300
caggaaacag ctatgaccat gattacgaat tcaggtgac tgatagtgac ctgttcgttg    360
caacaaattg atgagcaatg cttttttata atgccaactt tgtacaaaaa agcaggcggc   420
gcgtcctgca ggatagggat aacagggtaa tggcgcgcca agcttatcga taccgtcgac   480
ctcgagcggc cgccagtgtg atggatatct gcagaattgc ccttcgaagg acaaaaaaa    540
gcaccgactc ggtgccactt tttcaagttg ataacggact agccttattt taacttgcta   600
tttctagctc taaaacgccc agttggaatg taggtgcaac acaagcgaca gcgcgcgggt   660
ttataagttg gtcgcgttcg agttagctgg gcaatgtggt actaaactgt tcctcccgcc   720
tctcgcgctc acactcgccc tgtgggccgc tcaccgtgca cgtacttggg cctcccgctc   780
ccccgcatgc atccagccca tcacagcgaa gagaatcggg cttttcttct ccccatctcc   840
ctacacaacc accaaataca gccaggccgt tggttcatga tccaagggca attccagcac   900
actggcggcc gttactagtg gatccgagct cggtacctta attaaattac ctgttatcc    960
ctatcctgca ggattaacac ccaacttttc tatccaagct tgccaacatg gtggagcacg  1020
acactctcgt ctactccaag aatatcaaag atacagtctc agaagaccaa agggctattg  1080
agactttca acaagggta atatcgggaa acctcctcgg attccattgc ccagctatct    1140
gtcacttcat caaaggaca gtagaaaagg aaggtggcac ctacaaatgc catcattgcg    1200
ataaaggaaa ggctatcgtt caagatgcct ctgccgacag tggtcccaaa gatggacccc   1260
cacccacgag gagcatcgtg gaaaagaag acgttccaac cacgtcttca aagcaagtgg   1320
attgatgtga taacatggtg gagcacgaca ctctcgtcta ctccaagaat atcaaagata   1380
cagtctcaga gaccaaaggg ctattgagac ttttcaaca agggtaata tcgggaaacc    1440
tcctcggatt ccattgccca gctatctgtc acttcatcaa aggacagta gaaaaggaag   1500
gtggcaccta caaatgccat cattgcgata aggaaaggc tatcgttcaa gatgcctctg   1560
ccgacagtgg tccaaagat ggacccccac cacgaggag catcgtggaa aagaagacg    1620
ttccaaccac gtcttcaaag caagtggatt gatgtgatat ctccactgac gtaagggatg   1680
acgcacaatc ccactatcct tcgcaagacc cttcctctat ataaggaagt tcatttcatt   1740
tggagaggcc ggtctagaga attccaagca acgaactgcg agtgattcaa gaaaaagaa    1800
aacctgagct ttcgatctct acggagtggt tcttgttct ttgaaaaaga ggggattac    1860
atatggctcc taagaagaag cggaaggttg gtattcacgg ggtgcctgcg gctatggaca  1920
agaagtactc gatcgggctg gccatcggaa caaattctgt aggctgggct gtaataaccg   1980
```

```
atgagtacaa ggtgccctct aaaaaattta aggtccttgg caatacggat agacattcca    2040
taaagaagaa tcttatcggt gcgctgctct ttgacagcgg cgagaccgcg gaggcgaccc    2100
ggttgaaacg caccgcgaga cgccgttaca caaggcgtaa gaatagaatc tgttatctcc    2160
aggagatatt ctctaatgaa atggcgaagg tagacgattc cttctttcac cgtctggagg    2220
aaagttttct cgttgaggaa gataagaaac atgaaagaca cccgatcttc ggaaacattg    2280
tcgacgaggc cgcttatcat gaaaagtacc ctaccatcta ccatcttaga aagaaacttg    2340
ttgacagcac ggataaggct gatctcaggc tgatatacct ggctctggca catatgatta    2400
agttcagagg gcatttcctt atcgaaggcg acctgaatcc agataattca gatgtagaca    2460
agctcttcat tcaacttgtg cagacttata atcagctctt cgaagaaaat ccaataaacg    2520
cgtcgggtgt agacgcaaag gccatactgt ccgctaggct ttctaagtca cgtagacttg    2580
agaatctcat tgcccaactc cccggcgaga agaagaacgg cttgtttgga aatctgatag    2640
cgctgtccct gggtcttaca ccaaatttca agagtaattt cgatttggca gaagatgcta    2700
agttgcagct cagtaaagac acctacgatg acgatcttga taatttgttg gctcagattg    2760
gcgatcagta tgcagatctt ttcttggccg ctaagaattt gtctgatgca attctgctta    2820
gcgacatttt gagggttaat acagaaatca ccaaggcacc cttgtcggcg tcaatgataa    2880
agaggtatga tgagcaccac caagacctga cgctcctcaa ggctcttgtt cggcagcaat    2940
tgccggagaa gtacaaagag atcttcttcg accagtctaa gaacggatat gcgggctaca    3000
tagacggtgg agcgagtcag gaggaattct acaagttcat aaagcccatt ctcgagaaga    3060
tggatggtac ggaagaactg cttgtgaaac ttaacagaga agatcttttg cggaagcaga    3120
gaactttcga caacggaagt ataccacacc agatacatct cggagagctt catgctattc    3180
tcagaagaca gagggatttc tacccttctt gaaggataa cagagaaaag atagagaaga    3240
tcctcacgtt taggatccct tactacgtag gtcctcttgc tcgcggcaat agtaggttcg    3300
cctggatgac ccgcaagtct gaagaaacta tcaccccttg gaatttcgaa gaggttgtag    3360
acaaaggtgc ttcagcacag agtttcattg agaggatgac caacttcgac aagaacctcc    3420
ccaacgaaaa ggtcctgcct aagcacagcc tcctctacga atactttact gtctataatg    3480
agcttacaaa agttaagtac gtgacagagg gaatgcggaa gcccgcattc ctttccggag    3540
aacaaaagaa ggcgatcgtg gatcttctct tcaagacgaa ccgcaaggtg acggttaaac    3600
agttgaagga agattacttc aagaagatag aatgttttga tagcgtggaa atcagcggcg    3660
tcgaagatag gttcaacgct tccctgggaa cgtaccacga tctcctcaag attatcaaag    3720
ataaggactt tcttgataac gaagagaatg aggacatctt ggaagacatt gttctgacgc    3780
tcaccctgtt cgaagatcgc gagatgattg aggaacgctt gaagacctac gcacacctgt    3840
tcgatgacaa ggttatgaag caacttaaac ggcgccggta tacgggctgg ggacggcttt    3900
cgcggaagct gataaatgga atccgtgaca agcagtctgg caagacaata ctcgacttct    3960
tgaagtcgga tggttttgcc aatagaaatt ttatgcaact cattcatgat gactcgctta    4020
cttttaagga ggacatccag aaggcccagg tatcaggaca gggtgactct ttgcacgaac    4080
acatcgcgaa cctggcgggc tccccgcgca ttaagaaggg aatttttgcag actgtcaagg    4140 tggtcgatga actcgtgaag gttatgggac gtcataagcc ggaaaatatt gtgattgaga    4200
tggctcgcga gaatcaaaca acacagaagg gccaaaagaa cagtagagaa cgcatgaagc    4260
gcatcgaaga gggcatcaaa gagctgggca gtcagatcct taaagaacat ccagtcgaga    4320
atacacagct tcagaacgaa aagctgtacc tttattacct tcaaaatggg cgtgatatgt    4380
```

```
atgtggatca ggaactcgat atcaataggc tgagtgacta tgatgtcgac catatcgtcc   4440
cgcaaagttt cctcaaggac gacagtatag acaacaaagt tctcacacgg tcagataaga   4500
atcgcggcaa gagcgataat gtaccgtcgg aggaggtagt caagaagatg aagaattact   4560
ggcgccagtt gctcaacgcc aagctcatca ctcagaggaa atttgacaac cttacgaaag   4620
ccgagcgggg cggactctct gaactggaca aggccggttt cataaagcgc cagctcgttg   4680
agacacgtca aattactaag cacgtcgctc aaatattgga ttcccgcatg aatactaagt   4740
acgatgagaa tgataagctc atacgtgaag ttaaggtcat tactctcaag tccaagcttg   4800
tatcggactt ccgtaaggac ttccaattct acaaggtccg ggaaatcaat aattatcacc   4860
atgcccatga cgcttatctg aacgcggtcg tgggcacggc actcattaag aaatacccaa   4920
aacttgagtc agaatttgtt tacggggact ataaagttta tgacgtgcgg aagatgatag   4980
cgaagtcgga acaagagata ggaaaggcga ctgcaaagta ctttttttac tccaacataa   5040
tgaatttctt taagaccgaa ataacccttg caaacggtga atcagaaagt cggcctctga   5100
ttgaaacaaa tggcgagacg ggcgagatcg tctgggacaa ggggagggac ttcgcaacgg   5160
ttcgcaaggt ccttagcatg ccgcaagtaa atatagttaa gaagacggaa gttcagaccg   5220
gcggctttag taaagaaagc atacttccta aaaggaattc cgacaaactg atagcgcgca   5280
agaaggactg ggatccaaag aagtatggag gatttgactc cccaaccgtt gcttatagcg   5340
tgttggtagt agccaaggtg gaaaagggta agtctaagaa attgaagtcg gtgaaggagt   5400
tgttggggat aactataatg gagcggagtt cgttcgagaa gaacccaatt gactttctcg   5460
aagccaaagg ctacaaggag gtcaagaagg acctgattat taagttgcca aagtactcgc   5520
tcttcgaact cgagaacggg agaaagcgta tgctggcgtc ggcgggcgag ctgcagaaag   5580
gaaacgagct ggctttgcca tcgaaatacg taaatttcct gtacctcgcc tcacattatg   5640
agaagcttaa agggtctcca gaagacaatg aacagaagca gctgtttgtt gaacagcaca   5700
agcactactt ggacgagatt atagaacaaa tctccgagtt ctctaaacgg ttatccttg   5760
cagacgccaa tttggataag gtcctctcgg cttataataa gcatagagat aagccaatcc   5820
gggagcaggc tgaaaatatc atacacctct ttacgttgac taatttgggt gcgccagcgg   5880
cattcaagta cttcgataca acaatcgatc gtaagcgcta cacaagcact aaggaagtcc   5940
tggacgcgac gctgatacac cagtccatta ctggactgta tgaaaccaga atagatctta   6000
gccagctcgg cggtgatgga ggagggccta gggctgatcc taagaagaag aggaaggttg   6060
gaggagggcc aggagcagag tatgttagag cgttgtttga ttttaacggt aacgatgaag   6120
aggatttacc ctttaagaaa ggcgacattc tcaggattag ggataaacct gaagagcaat   6180
ggtgaaatgc tgaggatagt gaaggcaaac gaggaatgat tttagtgccg tatgtggaga   6240
aatattcggg tgactacaaa gatcatgatg gtgattacaa agaccatgac atcgactaca   6300
aggatgatga tgataagtca gggatgacag atgctgaata tgtcagaatc cacgaaaagt   6360
tggacattta cacgtttaag aagcagttct tcaacaacaa gaaatctgtt tcgcataggt   6420
gctatgtgct tttcgaacta aaacgtcgtg gagaaagacg ggcttgcttt tggggttacg   6480
cggttaacaa accacaatca ggtactgaac gaggaataca cgctgaaatc ttttctatcc   6540
gaaaggttga ggaatatcta cgtgacaatc ctggacagtt cactatcaat tggtattcta   6600
gctggtcacc atgtgcagat tgtgctgaga agattctcga atggtacaat caagagctta   6660
gaggcaatgg acatacattg aaaatatggg catgcaagct ctactacgaa aagaatgcca   6720
```

```
gaaaccaaat tgggctttgg aacttgaggg ataatggagt tgggcttaat gtcatggttt    6780
ctgagcacta tcaatgttgt cggaagatct tcatacaaag ttcccataac cagttgaatg    6840
agaacagatg gttagagaaa acccttaaaa gagccgagaa gagaagatcc gaactgagca    6900
ttatgataca ggtcaaaatt ctgcatacca ctaagagtcc agctgtaggt cctaagaaga    6960
aacgtaaagt agggccctga tccaggcctc ccagctttcg tccgtatcat cggtttcgac    7020
aacgttcgtc aagttcaatg catcagtttc attgcccaca caccagaatc ctactaagtt    7080
tgagtattat ggcattggaa aagctgttttt cttctatcat ttgttctgct tgtaatttac    7140
tgtgttcttt cagttttgt tttcggacat caaaatgcaa atggatggat aagagttaat    7200
aaatgatatg gtccttttgt tcattctcaa attattatta tctgttgttt ttactttaat    7260
gggttgaatt taagtaagaa aggaactaac agtgtgatat taaggtgcaa tgttagacat    7320
ataaaacagt ctttcacctc tctttggtta tgtcttgaat tggtttgttt cttcacttat    7380
ctgtgtaatc aagtttacta tgagtctatg atcaagtaat tatgcaatca agttaagtac    7440
agtataggct tgagctccct aggcccctag gtaattcttc ggacccaaga atgctaagcc    7500
aagaggagct gttatcgccg tcctcctgct tgtttctctc tttttgttgc tgtttcttca    7560
ttagcgtgga caaagttttc aaccggccta tctgttatca ttttcttcta ttcaaagact    7620
gtaataccta ttgctacctg tggttctcac ttgtgatttt ggacacatat gttcggttta    7680
ttcaaattta atcagatgcc tgatgagggt accagaaaaa atacgtgttc tggttgtttt    7740
tgagttgcga ttattctatg aaatgaataa catcgaagtt atcatcccag tatttcgca     7800
tgaatgttct tttcttctgt cttgtgcatc agtgatctag tgcatgggag tttgtattgt    7860
gatgttcgac atcacgtaac ttccactttg cctttgctgt tcgatatttt aatgacatgt    7920
cacacacact tctgatactt ttctttcttg gctattgtgc cagcatgatg caagatgcat    7980
cacagcatca gatatattct catcgtcagg ctttagcagc acacgagcac gctttgccgc    8040
ttaaaagttg tacggcgcag cttagacatc ccctgtagaa gtgataatct tttcactttt    8100
ccttaaacaa attgagaggg gaaatggaac catgtggatc agagaagctt ttgtttcttt    8160
acacaagaat atttggtaca gtgggggtcc tatgttcgtg ggttcgtggc ttggctgcct    8220
gtcttcaacc aagtgttttc agttcaacat gttagcgtgt agaaagagca caattctgtt    8280
tatctccaag gtaaaatgtg gcattctgtt aaagaacatg atcctgccaa ttttttaagt    8340
ttcaatggaa gaggaatgta aagctttcta tggtttgtgt acacaacaca gtggaagagg    8400
agtgcaagct ttctatggtt tgtgtgcgcg ttgtgtgtca gcacttcaat tttgttagaa    8460
aatgaaagaa aaaaaaggat gatcatgctt atagtaaatc actcttttcc ctcgccttct    8520
gtacgttttg acttgacaag atttttaaaat ctgtacatga cctttgtttt aaaattactt    8580
tatgtatttc catctttcaa gttatgcaga tgtcatcaca aattgttaca ccaatcacca    8640
ggctggctgt ttatatatta tcagaccagg ctatatagag tatactatac taactgttca    8700
tattatctgg aaatcttgct tgctacttga gcggtaaaag ggtatagata tgagggtccc    8760
cagattagcc ttttcaattt cagaaagaat gctaacccac agatggttag agaggcttac    8820
gcagcaggtc tcatcaagac gatctacccg agcaataatc tccaggaaat caaataccttt   8880
cccaagaagg ttaaagatgc agtcaaaaga ttcaggacta actgcatcaa gaacacagag    8940
aaagatatat ttctcaagat cagaagtact attccagtat ggacgattca aggcttgctt    9000
cacaaaccaa ggcaagtaat agagattgga gtctctaaaa aggtagttcc cactgaatca    9060
aaggccatgg agtcaaagat tcaaatagag gacctaacag aactcgccgt aaagactggc    9120
```

```
gaacagttca tacagagtct cttacgactc aatgacaaga agaaaatctt cgtcaacatg    9180
gtggagcacg acacacttgt ctactccaaa aatatcaaag atacagtctc agaagaccaa    9240
agggcaattg agacttttca acaaagggta atatccggaa acctcctcgg attccattgc    9300
ccagctatct gtcactttat tgtgaagata gtggaaaagg aaggtggctc ctacaaatgc    9360
catcattgcg ataaaggaaa ggccatcgtt gaagatgcct ctgccgacag tggtcccaaa    9420
gatggacccc cacccacgag gagcatcgtg aaaaagaag acgttccaac cacgtcttca     9480
aagcaagtgg attgatgtga tatctccact gacgtaaggg atgacgcaca atcccactat    9540
ccttcgcaag acccttcctc tatataagga agttcatttc atttggagag aacacggggg    9600
actctagaat gaaaaagcct gaactcaccg cgacgtctgt cgagaagttt ctgatcgaaa    9660
agttcgacag cgtctccgac ctgatgcagc tctcggaggg cgaagaatct cgtgctttca    9720
gcttcgatgt aggagggcgt ggatatgtcc tgcgggtaaa tagctgcgcc gatggtttct    9780
acaaagatcg ttatgtttat cggcactttg catcggccgc gctcccgatt ccggaagtgc    9840
ttgacattgg ggagtttagc gagagcctga cctattgcat ctcccgccgt tcacagggtg    9900
tcacgttgca agacctgcct gaaaccgaac tgcccgctgt tctacaaccg gtcgcggagg    9960
ctatggatgc gatcgctgcg gccgatctta gccagacgag cgggttcggc ccattcggac   10020
cgcaaggaat cggtcaatac actacatggc gtgatttcat atgcgcgatt gctgatcccc   10080
atgtgtatca ctggcaaact gtgatggacg acaccgtcag tgcgtccgtc gcgcaggctc   10140
tcgatgagct gatgctttgg gccgaggact gccccgaagt ccggcacctc gtgcacgcgg   10200
atttcggctc caacaatgtc ctgacggaca atggccgcat aacagcggtc attgactgga   10260
gcgaggcgat gttcggggat tcccaatacg aggtcgccaa catcttcttc tggaggccgt   10320
ggttggcttg tatggagcag cagacgcgct acttcgagcg gaggcatccg gagcttgcag   10380
gatcgccacg actccgggcg tatatgctcc gcattggtct tgaccaactc tatcagagct   10440
tggttgacgg caatttcgat gatgcagctt gggcgcaggg tcgatgcgac gcaatcgtcc   10500
gatccggagc cgggactgtc gggcgtacac aaatcgcccg cagaagcgcg gccgtctgga   10560
ccgatggctg tgtagaagta ctcgccgata gtggaaaccg acgccccagc actcgtccga   10620
gggcaaagaa ataggagctc tgggctaatc taaaacgatt tatctgtggc ttcaagtgta   10680
tcgatcactt atgtgaggtg taattactgg tgttttggt gtgctctggt tcctttcaag   10740
tgtgttgttg ccgctcgaac tactccgcta tgtaaaacgg taaaacctgt tgtctcatta   10800
tgaaagtgaa ctatattatg ttctactact actctactta gtcaatttc ttcaccttga    10860 ttagtgtaaa tatgaatctt atattcttat gtcttaagaa attagcacat gtgaagcctc   10920
caagtgcata ttttctcgat cgcgagacgc acaatgcgtg agaaattcag ctggttatac   10980
tcaaatatat aatatatctc agcagcagct catggagatt caggaaactt ggcatcccta   11040
atccctacca tttccattct tccgagattg acagttcaat acaagtacag taatctcctg   11100
gtaagtttct tattaacttg acatgtagta gtaataattt gtacgtagca tagatacata   11160
gacacaaaaa tgtcctcccc attgagctag ccgattggag ccgaacaccg caggaatgaa   11220
tttacataat ctgcaaagaa taaatggaat gtgcctccac aggaaaacca gcggcagtgt   11280
ggcgttttca agagcagccg taagtcgaag cctattctga atcgtagaaa tcactgggc    11340 atggtgtaat tacatccgac tccaacatct gtaccaccct gtgcattgta ggccgctcct   11400
ctggcaaaga acttacacat tgtttagcaa gagaaagtag agcatccaag gtctcaatct   11460
```

-continued

```
gcactccctc acaatatgga tcgacaattt ccctctcccg attctcaccg accaggaaat   11520
tcaactgcca cagagcaagt agattatttc aagaatacat taaatcaatt gaaggcatac   11580
gtaattcata tcagaaaact gtggatatga aatggaagga cataaaggtc atacataccc   11640
atccaacaat gttcaatccc ttttcaataa atgatgcatc agtaggtcgt tttccgctta   11700
gtatttcaag tagcaaaact ccaaaactgt agacgtcagt cttttcggtg gctctgccac   11760
tttgcatata ctcctgcagg tcgaccatag tgactggata tgttgtgttt tacagtatta   11820
tgtagtctgt tttttatgca aaatctaatt taatatattg atatttatat cattttacgt   11880
ttctcgttca gctttcttgt acaaagtggt gatatcccgc ggaaatacgt agaattcggg   11940
aagcttggca ctggccgtcg ttttacaacg tcgtgactgg gaaaaccctg gcgttaccca   12000
acttaatcgc cttgcagcac atccccgttt cgccagctgg cgtaatagcg aagaggcccg   12060
caccgatcgc ccttcccaac agttgcgcag cctgaatggc gaatgctaga gcaattcggc   12120
gttaattcag tacattaaaa acgtccgcaa tgtgttatta agttgtctaa gcgtcaattt   12180
gtttacacca caatatatcc tgccaccagc cagccaacag ctccccgacc ggcagctcgg   12240
cacaaaatca ccactcgata caggcagccc atcagtccgg gacggcgtca gcgggagagc   12300
cgttgtaagg cggcagactt tgctcatgtt accgatgcta ttcggaagaa cggcaactaa   12360
gctgccgggt ttgaaacacg gatgatctcg cggagggtag catgttgatt gtaacgatga   12420
cagagcgttg ctgcctgtga tcaattcggg cacgaaccca gtggacataa gcctcgttcg   12480
gttcgtaagc tgtaatgcaa gtagcgtaac tgccgtcacg caactggtcc agaaccttga   12540
ccgaacgcag cggtggtaac ggcgcagtgg cggttttcat ggcttcttgt tatgacatgt   12600
ttttttgggg tacagtctat gcctcgggca tccaagcagc aagcgcgtta cgccgtgggt   12660
cgatgtttga tgttatggag cagcaacgat gttacgcagc agggcagtcg ccctaaaaca   12720
aagttaaaca tcatggggga agcggtgatc gccgaagtat cgactcaact atcagaggta   12780
gttggcgtca tcgagcgcca tctcgaaccg acgttgctgg ccgtacattt gtacggctcc   12840
gcagtggatg gcggcctgaa gccacacagt gatattgatt tgctggttac ggtgaccgta   12900
aggcttgatg aaacaacgcg gcgagctttg atcaacgacc ttttggaaac ttcggcttcc   12960
cctggagaga gcgagattct ccgcgctgta gaagtcacca ttgttgtgca cgacgacatc   13020
attccgtggc gttatccagc taagcgcgaa ctgcaatttg gagaatggca gcgcaatgac   13080
attcttgcag gtatcttcga gccagccacg atcgacattg atctggctat cttgctgaca   13140
aaagcaagag aacatagcgt tgccttggta ggtccagcgg cggaggaact ctttgatccg   13200
gttcctgaac aggatctatt tgaggcgcta aatgaaacct taacgctatg gaactcgccg   13260
cccgactggg ctggcgatga gcgaaatgta gtgcttacgt tgtcccgcat ttggtacagc   13320
gcagtaaccg gcaaaatcgc gccgaaggat gtcgctgccg actgggcaat ggagcgcctg   13380
ccggcccagt atcagcccgt catacttgaa gctagacagg cttatcttgg acaagaagaa   13440
gatcgcttgg cctcgcgcgc agatcagttg gaagaatttg tccactacgt gaaaggcgag   13500
atcaccaagg tagtcggcaa ataatgtcta gctagaaatt cgttcaagcc gacgccgctt   13560
cgccggcgtt aaatcaagcg attagatgca ctaagcacat aattgctcac agccaaacta   13620
tcaggtcaag tctgctttta ttattttaa gcgtgcataa taagccctac acaaatttggg   13680
agatatatca tgcatgacca aaatccctta acgtgagttt tcgttccact gagcgtcaga   13740
ccccgtagaa aagatcaaag gatcttcttg agatcctttt tttctgcgcg taatctgctg   13800
cttgcaaaca aaaaaaccac cgctaccagc ggtggtttgt ttgccggatc aagagctacc   13860
```

```
aactctttttt ccgaaggtaa ctggcttcag cagagcgcag ataccaaata ctgtccttct   13920
agtgtagccg tagttaggcc accacttcaa gaactctgta gcaccgccta catacctcgc   13980
tctgctaatc ctgttaccag tggctgctgc cagtggcgat aagtcgtgtc ttaccgggtt   14040
ggactcaaga cgatagttac cggataaggc gcagcggtcg ggctgaacgg ggggttcgtg   14100
cacacagccc agcttggagc gaacgaccta caccgaactg agatacctac agcgtgagct   14160
atgagaaagc gccacgcttc ccgaagggag aaaggcggac aggtatccgg taagcggcag   14220
ggtcggaaca ggagagcgca cgagggagct ccaggggga aacgcctggt atctttatag   14280
tcctgtcggg tttcgccacc tctgacttga gcgtcgattt ttgtgatgct cgtcagggg   14340
gcggagccta tggaaaaacg ccagcaacgc ggccttttta cggttcctgg ccttttgctg   14400
gccttttgct cacatgttct ttcctgcgtt atcccctgat tctgtggata accgtattac   14460
cgcctttgag tgagctgata ccgctcgccg cagccgaacg accgagcgca gcgagtcagt   14520
gagcgaggaa gcggaagagc gcctgatgcg gtattttctc cttacgcatc tgtgcggtat   14580
ttcacaccgc atatggtgca ctctcagtac aatctgctct gatgccgcat agttaagcca   14640
gtatacactc cgctatcgct acgtgactgg gtcatggctg cgccccgaca cccgccaaca   14700
cccgctgacg cgccctgacg ggcttgtctg ctcccggcat ccgcttacag acaagctgtg   14760
accgtctccg ggagctgcat gtgtcagagg ttttcaccgt catcaccgaa acgcgcgagg   14820
cagggtgcct tgatgtgggc gccggcggtc gagtggcgac ggcgcggctt gtccgcgccc   14880
tggtagattg cctggccgta ggccagccat ttttgagcgg ccagcggccg cgataggccg   14940
acgcgaagcg gcgggcgta gggagcgcag cgaccgaagg gtaggcgctt tttgcagctc   15000
ttcggctgtg cgctgccag acagttatgc acaggccagg cgggttttaa gagttttaat   15060
aagttttaaa gagttttagg cggaaaaatc gcctttttc tctttatat cagtcactta   15120
catgtgtgac cggttcccaa tgtacggctt tgggttccca atgtacgggt tccggttccc   15180
aatgtacggc tttgggttcc caatgtacgt gctatccaca ggaaagagac cttttcgacc   15240
tttttcccct gctagggcaa tttgccctag catctgctcc gtacattagg aaccggcgga   15300
tgcttcgccc tcgatcaggt tgcggtagcg catgactagg atcgggccag cctgccccgc   15360
ctcctccttc aaatcgtact ccggcaggtc atttgacccg atcagcttgc gcacggtgaa   15420
acagaacttc ttgaactctc cggcgctgcc actgcgttcg tagatcgtct tgaacaacca   15480
tctggcttct gccttgcctg cggcgcggcg tgccaggcgg tagagaaaac ggccgatgcc   15540
gggatcgatc aaaagtaat cggggtgaac cgtcagcacg tccgggttct tgccttctgt   15600
gatctcgcgg tacatccaat cagctagctc gatctcgatg tactccggcc gcccggtttc   15660
gctctttacg atcttgtagc ggctaatcaa ggcttcaccc tcggataccg tcaccaggcg   15720
gccgttcttg gccttcttcg tacgctgcat ggcaacgtgc gtggtgttta accgaatgca   15780
ggtttctacc aggtcgtctt tctgctttcc gccatcggct cgccggcaga acttgagtac   15840
gtccgcaacg tgtggacgga acacgcggcc gggcttgtct cccttcccttt ccggtatcg   15900
gttcatggat tcggttagat gggaaaccgc catcagtacc aggtcgtaat cccacacact   15960
ggccatgccg ccggccctg cggaaacctc tacgtgcccg tctggaagct cgtagcggat   16020
cacctcgcca gctcgtcggt cacgcttcga cagacggaaa acggccacgt ccatgatgct   16080
gcgactatcg cgggtgccca cgtcatagag catcggaacg aaaaaatctg ttgctcgtc   16140
gcccttgggc ggcttcctaa tcgacggcgc accggctgcc ggcggttgcc gggattctttt   16200
```

```
gcggattcga tcagcggccg cttgccacga ttcaccgggg cgtgcttctg cctcgatgcg   16260
ttgccgctgg gcggcctgcg cggccttcaa cttctccacc aggtcatcac ccagcgccgc   16320
gccgatttgt accgggccgg atggtttgcg accgtcacgc cgattcctcg ggcttggggg   16380
ttccagtgcc attgcagggc cggcagacaa cccagccgct tacgcctggc caaccgcccg   16440
ttcctccaca catggggcat tccacggcgt cggtgcctgg ttgttcttga ttttccatgc   16500
cgcctccttt agccgctaaa attcatctac tcatttattc atttgctcat ttactctggt   16560
agctgcgcga tgtattcaga tagcagctcg gtaatggtct tgccttggcg taccgcgtac   16620
atcttcagct tggtgtgatc ctccgccggc aactgaaagt tgacccgctt catggctggc   16680
gtgtctgcca ggctggccaa cgttgcagcc ttgctgctgc gtgcgctcgg acggccggca   16740
cttagcgtgt ttgtgctttt gctcattttc tctttacctc attaactcaa atgagttttg   16800
atttaatttc agcggccagc gcctggacct cgcgggcagc gtcgccctcg ggttctgatt   16860
caagaacggt tgtgccggcg gcggcagtgc ctgggtagct cacgcgctgc gtgatacggg   16920
actcaagaat gggcagctcg tacccggcca gcgcctcggc aacctcaccg ccgatgcgcg   16980
tgcctttgat cgcccgcgac acgacaaagg ccgcttgtag ccttccatcc gtgacctcaa   17040
tgcgctgctt aaccagctcc accaggtcgg cggtggccca tatgtcgtaa gggcttggct   17100
gcaccggaat cagcacgaag tcggctgcct tgatcgcgga cacagccaag tccgccgcct   17160
ggggcgctcc gtcgatcact acgaagtcgc gccggccgat ggccttcacg tcgcggtcaa   17220
tcgtcgggcg gtcgatgccg acaacggtta gcggttgatc ttcccgcacg gccgcccaat   17280
cgcgggcact gccctgggga tcggaatcga ctaacagaac atcggccccg gcgagttgca   17340
gggcgcgggc tagatgggtt gcgatggtcg tcttgcctga cccgcctttc tggttaagta   17400
cagcgataac cttcatgcgt tccccttgcg tatttgttta tttactcatc gcatcatata   17460
cgcagcgacc gcatgacgca agctgtttta ctcaaataca catcacctt ttagacggcg   17520 gcgctcggtt tcttcagcgg ccaagctggc cggccaggcc gccagcttgg catcagacaa   17580
accggccagg atttcatgca gccgcacggt tgagacgtgc gcgggcggct cgaacacgta   17640
cccgccgcgc atcatctccg cctcgatctc ttcggtaatg aaaaacggtt cgtcctggcc   17700
gtcctggtgc ggtttcatgc ttgttcctct tggcgttcat tctcggcggc cgccagggcg   17760
tcggcctcgg tcaatgcgtc ctcacggaag gcaccgcgcc gcctggcctc ggtgggcgtc   17820
acttcctcgc tgcgctcaag tgcgcggtac agggtcgagc gatgcacgcc aagcagtgca   17880
gccgcctctt tcacggtgcg gccttcctgg tcgatcagct cgcgggcgtg cgcgatctgt   17940
gccggggtga gggtagggcg ggggccaaac ttcacgcctc gggccttggc ggcctcgcgc   18000
ccgctccggg tgcggtcgat gattaggaa cgctcgaact cggcaatgcc ggcgaacacg   18060
gtcaacacca tgcggccggc cggcgtggtg gtgtcggccc acggctctgc caggctacgc   18120
aggcccgcgc cggcctcctg gatgcgctcg gcaatgtcca gtaggtcgcg ggtgctgcgg   18180
gccaggcggt ctagcctggt cactgtcaca acgtcgccag ggcgtaggtg gtcaagcatc   18240
ctggccagct ccgggcggtc gcgcctggtg ccggtgatct tctcggaaaa cagcttggtg   18300
cagccggccg cgtgcagttc ggcccgttgg ttggtcaagt cctggtcgtc ggtgctgacg   18360
cgggcatagc ccagcaggcc agcggcggcg ctcttgttca tggcgtaatg tctccggttc   18420
tagtcgcaag tattctactt tatgcgacta aacacgcga caagaaaacg ccaggaaaag   18480
ggcagggcgg cagcctgtcg cgtaacttag gacttgtgcg acatgtcgtt ttcagaagac   18540
ggctgcactg aacgtcagaa gccgactgca ctatagcagc ggagggggttg gatcaaagta   18600
```

-continued

```
ctttgatccc gaggggaacc ctgtggttgg catgcacata caaatggacg aacggataaa    18660 cctttcacg ccctttaaa tatccgttat tctaa                                 18695
```

<210> SEQ ID NO 13
<211> LENGTH: 35
<212> TYPE: DNA
<213> ORGANISM: Artificial Sequence
<220> FEATURE:
<223> OTHER INFORMATION: Primer
<400> SEQUENCE: 13

```
atgcatcctg caggctctag aggatccccc ctcag                               35
```

<210> SEQ ID NO 14
<211> LENGTH: 35
<212> TYPE: DNA
<213> ORGANISM: Artificial Sequence
<220> FEATURE:
<223> OTHER INFORMATION: Primer
<400> SEQUENCE: 14

```
agccgggcgg ccgctttact tgtacagctc gtcca                               35
```

<210> SEQ ID NO 15
<211> LENGTH: 30
<212> TYPE: DNA
<213> ORGANISM: Artificial Sequence
<220> FEATURE:
<223> OTHER INFORMATION: Primer
<400> SEQUENCE: 15

```
atgaaaaagc ctgaactcac cgcgacgtct                                     30
```

<210> SEQ ID NO 16
<211> LENGTH: 30
<212> TYPE: DNA
<213> ORGANISM: Artificial Sequence
<220> FEATURE:
<223> OTHER INFORMATION: Primer
<400> SEQUENCE: 16

```
cctcgctcca gtcaatgacc gctgttatgc                                     30
```

<210> SEQ ID NO 17
<211> LENGTH: 45
<212> TYPE: DNA
<213> ORGANISM: Artificial Sequence
<220> FEATURE:
<223> OTHER INFORMATION: Primer
<400> SEQUENCE: 17

```
agtccctgca ggttaattaa cttgcgctgc gtttgtgcgg gtgcg                    45
```

<210> SEQ ID NO 18
<211> LENGTH: 47
<212> TYPE: DNA
<213> ORGANISM: Artificial Sequence
<220> FEATURE:
<223> OTHER INFORMATION: Primer
<400> SEQUENCE: 18

```
tgacggtacc actagttagt agtacccaat aagatcgacc gaagaga                  47
```

<210> SEQ ID NO 19

<211> LENGTH: 30
<212> TYPE: DNA
<213> ORGANISM: Artificial Sequence
<220> FEATURE:
<223> OTHER INFORMATION: Primer

<400> SEQUENCE: 19
ccgtaagaac caccagcgac accacgtcct                                      30

<210> SEQ ID NO 20
<211> LENGTH: 98
<212> TYPE: DNA
<213> ORGANISM: Artificial Sequence
<220> FEATURE:
<223> OTHER INFORMATION: Synthetic pRIT3-EGFP vector

<400> SEQUENCE: 20
ttacaattac tatttacaat tacagtcgac tctagaggat ccggcccagt tggaatgtag     60
gtggtgagca agggcgagga gctgttcacc ggggtggt                             98

<210> SEQ ID NO 21
<211> LENGTH: 98
<212> TYPE: DNA
<213> ORGANISM: Artificial Sequence
<220> FEATURE:
<223> OTHER INFORMATION: Synthetic pRIT3-EGFP vector

<400> SEQUENCE: 21
accaccccgg tgaacagctc ctcgcccttg ctcaccacct acattccaac tgggccggat     60
cctctagagt cgactgtaat tgtaaatagt aattgtaa                             98

<210> SEQ ID NO 22
<211> LENGTH: 12
<212> TYPE: PRT
<213> ORGANISM: Artificial Sequence
<220> FEATURE:
<223> OTHER INFORMATION: Synthetic pRIT3-EGFP vector

<400> SEQUENCE: 22

Val Ser Lys Gly Glu Glu Leu Phe Thr Gly Val Val
1               5                   10

<210> SEQ ID NO 23
<211> LENGTH: 98
<212> TYPE: DNA
<213> ORGANISM: Artificial Sequence
<220> FEATURE:
<223> OTHER INFORMATION: Synthetic pRIT3-EGFP vector

<400> SEQUENCE: 23
ttacaattac tatttacaat tacagtcgac tctagaggat ccggcccagt tggaatgtac     60
aaggtgagca agggcgagga gctgttcacc ggggtggt                             98

<210> SEQ ID NO 24
<211> LENGTH: 58
<212> TYPE: DNA
<213> ORGANISM: Artificial Sequence
<220> FEATURE:
<223> OTHER INFORMATION: Synthetic pRIT3-EGFP vector

<400> SEQUENCE: 24
ttacaattac tatttacaat tacagtcgac tctagaggat ccggcccagt tggaatgt      58

<210> SEQ ID NO 25

<211> LENGTH: 41
<212> TYPE: DNA
<213> ORGANISM: Artificial Sequence
<220> FEATURE:
<223> OTHER INFORMATION: Synthetic pRIT3-EGFP vector

<400> SEQUENCE: 25
aggtggtgag caagggcgag gagctgttca ccggggtggt g         41

<210> SEQ ID NO 26
<211> LENGTH: 58
<212> TYPE: DNA
<213> ORGANISM: Artificial Sequence
<220> FEATURE:
<223> OTHER INFORMATION: Synthetic pRIT3-EGFP vector

<400> SEQUENCE: 26
acattccaac tgggccggat cctctagagt cgactgtaat tgtaaatagt aattgtaa    58

<210> SEQ ID NO 27
<211> LENGTH: 41
<212> TYPE: DNA
<213> ORGANISM: Artificial Sequence
<220> FEATURE:
<223> OTHER INFORMATION: Synthetic pRIT3-EGFP vector

<400> SEQUENCE: 27
caccaccccg gtgaacagct cctcgccctt gctcaccacc t         41

<210> SEQ ID NO 28
<211> LENGTH: 96
<212> TYPE: DNA
<213> ORGANISM: Artificial Sequence
<220> FEATURE:
<223> OTHER INFORMATION: Synthetic pRIT3-EGFP vector

<400> SEQUENCE: 28
ttacaattac tatttacaat tacagtcgac tctagaggat ccggcccagt tggaatgtta    60
gtgagcaagg gcgaggagct gttcaccggg gtggtg                              96

<210> SEQ ID NO 29
<211> LENGTH: 106
<212> TYPE: DNA
<213> ORGANISM: Artificial Sequence
<220> FEATURE:
<223> OTHER INFORMATION: Synthetic pRIT3-EGFP vector

<400> SEQUENCE: 29
ttactattta caattactat ttacaattac agtcgactct agaggatccg gcccagttgg    60
aatgtaggtg gtgagcaagg gcgaggagct gttcaccggg gtggtg                  106

<210> SEQ ID NO 30
<211> LENGTH: 106
<212> TYPE: DNA
<213> ORGANISM: Artificial Sequence
<220> FEATURE:
<223> OTHER INFORMATION: Synthetic pRIT3-EGFP vector

<400> SEQUENCE: 30
caccaccccg gtgaacagct cctcgccctt gctcaccacc tacattccaa ctgggccgga    60
tcctctagag tcgactgtaa ttgtaaatag taattgtaaa tagtaa                  106

<210> SEQ ID NO 31
<211> LENGTH: 106

<212> TYPE: DNA
<213> ORGANISM: Artificial Sequence
<220> FEATURE:
<223> OTHER INFORMATION: Synthetic pRIT3-EGFP vector

<400> SEQUENCE: 31
ttactattta caattactat ttacaattac agtcgactct agaggatccg gcccagttgg    60
aatgtaaatg gtgagcaagg gcgaggagct gttcaccggg gtggtg                  106

<210> SEQ ID NO 32
<211> LENGTH: 105
<212> TYPE: DNA
<213> ORGANISM: Artificial Sequence
<220> FEATURE:
<223> OTHER INFORMATION: Synthetic pRIT3-EGFP vector

<400> SEQUENCE: 32
ttacaattac aattactatt tacaattaca gtcgactcta gaggatccgg cccagttgga    60
atgtaggtgg tgagcaaggg cgaggagctg ttcaccgggg tggtg                   105

<210> SEQ ID NO 33
<211> LENGTH: 105
<212> TYPE: DNA
<213> ORGANISM: Artificial Sequence
<220> FEATURE:
<223> OTHER INFORMATION: Synthetic pRIT3-EGFP vector

<400> SEQUENCE: 33
caccaccccg gtgaacagct cctcgccctt gctcaccacc tacattccaa ctgggccgga    60
tcctctagag tcgactgtaa ttgtaaatag taattgtaat tgtaa                   105

<210> SEQ ID NO 34
<211> LENGTH: 105
<212> TYPE: DNA
<213> ORGANISM: Artificial Sequence
<220> FEATURE:
<223> OTHER INFORMATION: Synthetic pRIT3-EGFP vector

<400> SEQUENCE: 34
ttacaattac aattactatt tacaattaca gtcgactcta gaggatccgg cccagttgga    60
atgtacgtag tgagcaaggg cgaggagctg ttcaccgggg tggtg                   105

<210> SEQ ID NO 35
<211> LENGTH: 105
<212> TYPE: DNA
<213> ORGANISM: Artificial Sequence
<220> FEATURE:
<223> OTHER INFORMATION: Synthetic pRIT3-EGFP vector

<400> SEQUENCE: 35
ttacaattac aattactatt tacaattaca gtcgactcta gaggatccgg cccagttgga    60
atgtacatag tgagcaaggg cgaggagctg ttcaccgggg tggtg                   105

<210> SEQ ID NO 36
<211> LENGTH: 105
<212> TYPE: DNA
<213> ORGANISM: Artificial Sequence
<220> FEATURE:
<223> OTHER INFORMATION: Synthetic pRIT3-EGFP vector

<400> SEQUENCE: 36
ttacaattac aattactatt tacaattaca gtcgactcta gaggatccgg cccagttgga    60

```
atgtacgtgg tgagcaaggg cgaggagctg ttcaccgggg tggtg                      105
```

<210> SEQ ID NO 37
<211> LENGTH: 48
<212> TYPE: DNA
<213> ORGANISM: Artificial Sequence
<220> FEATURE:
<223> OTHER INFORMATION: Synthetic pRIT3-EGFP vector

<400> SEQUENCE: 37

```
ttacaattac aattactatt tacaattaca gtcgactcta gaggatcc                   48
```

<210> SEQ ID NO 38
<211> LENGTH: 57
<212> TYPE: DNA
<213> ORGANISM: Artificial Sequence
<220> FEATURE:
<223> OTHER INFORMATION: Synthetic pRIT3-EGFP vector

<400> SEQUENCE: 38

```
ggcccagttg gaatgtaggt ggtgagcaag ggcgaggagc tgttcaccgg ggtggtg         57
```

<210> SEQ ID NO 39
<211> LENGTH: 48
<212> TYPE: DNA
<213> ORGANISM: Artificial Sequence
<220> FEATURE:
<223> OTHER INFORMATION: Synthetic pRIT3-EGFP vector

<400> SEQUENCE: 39

```
ggatcctcta gagtcgactg taattgtaaa tagtaattgt aattgtaa                   48
```

<210> SEQ ID NO 40
<211> LENGTH: 57
<212> TYPE: DNA
<213> ORGANISM: Artificial Sequence
<220> FEATURE:
<223> OTHER INFORMATION: Synthetic pRIT3-EGFP vector

<400> SEQUENCE: 40

```
caccaccccg gtgaacagct cctcgccctt gctcaccacc tacattccaa ctgggcc         57
```

<210> SEQ ID NO 41
<211> LENGTH: 86
<212> TYPE: DNA
<213> ORGANISM: Artificial Sequence
<220> FEATURE:
<223> OTHER INFORMATION: Synthetic pRIT3-EGFP vector

<400> SEQUENCE: 41

```
ttacaattac aattactatt tacaattaca gtcgactcta gaggatccta gtgagcaagg      60
gcgaggagct gttcaccggg gtggtg                                          86
```

<210> SEQ ID NO 42
<211> LENGTH: 105
<212> TYPE: DNA
<213> ORGANISM: Artificial Sequence
<220> FEATURE:
<223> OTHER INFORMATION: Synthetic pRIT3-EGFP vector

<400> SEQUENCE: 42

```
ttacaattac aattactatt tacaattaca gtcgactcta gaggatccgg cccagttgga      60
atgtagatga tgagcaaggg cgaggagctg ttcaccgggg tggtg                     105
```

```
<210> SEQ ID NO 43
<211> LENGTH: 20
<212> TYPE: PRT
<213> ORGANISM: Oryza sativa

<400> SEQUENCE: 43

Ser Asp Val Phe Ala Tyr Pro Gly Gly Ala Ser Met Glu Ile His Gln
1               5                   10                  15

Ala Leu Thr Arg
            20

<210> SEQ ID NO 44
<211> LENGTH: 60
<212> TYPE: DNA
<213> ORGANISM: Oryza sativa

<400> SEQUENCE: 44
agcgacgtgt tcgcctaccc gggcggcgcg tccatggaga tccaccaggc gctgacgcgc     60

<210> SEQ ID NO 45
<211> LENGTH: 60
<212> TYPE: DNA
<213> ORGANISM: Oryza sativa

<400> SEQUENCE: 45
gcgcgtcagc gcctggtgga tctccatgga cgcgccgccc gggtaggcga acacgtcgct     60

<210> SEQ ID NO 46
<211> LENGTH: 20
<212> TYPE: PRT
<213> ORGANISM: Oryza sativa

<400> SEQUENCE: 46

Ser Asp Val Phe Ala Tyr Pro Gly Gly Val Ser Met Glu Ile His Gln
1               5                   10                  15

Ala Leu Thr Arg
            20

<210> SEQ ID NO 47
<211> LENGTH: 60
<212> TYPE: DNA
<213> ORGANISM: Oryza sativa

<400> SEQUENCE: 47
agcgacgtgt tcgcctaccc gggcggcgtg tccatggaga tccaccaggc gctgacgcgc     60

<210> SEQ ID NO 48
<211> LENGTH: 60
<212> TYPE: DNA
<213> ORGANISM: Oryza sativa

<400> SEQUENCE: 48
gcgcgtcagc gcctggtgga tctccatgga cacgccgccc gggtaggcga acacgtcgct     60

<210> SEQ ID NO 49
<211> LENGTH: 60
<212> TYPE: DNA
<213> ORGANISM: Oryza sativa

<400> SEQUENCE: 49
agcgacgtgt tcgcctaccc gggcggtgtg tccatggaga tccaccaggc gctgacgcgc     60

<210> SEQ ID NO 50
```

```
<211> LENGTH: 77
<212> TYPE: DNA
<213> ORGANISM: Artificial Sequence
<220> FEATURE:
<223> OTHER INFORMATION: Synthetic pRIT3-EGFP vector

<400> SEQUENCE: 50
agtcgactct agaggatccg gcccagttgg aatgtaggtg gtgagcaagg gcgaggagct      60
gttcaccggg gtggtgc                                                    77

<210> SEQ ID NO 51
<211> LENGTH: 77
<212> TYPE: DNA
<213> ORGANISM: Artificial Sequence
<220> FEATURE:
<223> OTHER INFORMATION: Synthetic pRIT3-EGFP vector

<400> SEQUENCE: 51
agtcgactct agaggatccg gcccagttgg aatgtatatg gtgagcaagg gcgaggagct      60
gttcaccggg gtggtgc                                                    77

<210> SEQ ID NO 52
<211> LENGTH: 28
<212> TYPE: PRT
<213> ORGANISM: Oryza sativa

<400> SEQUENCE: 52

Arg Cys Gly Val Ser Asp Val Phe Ala Tyr Pro Gly Gly Ala Ser Met
1               5                   10                  15

Glu Ile His Gln Ala Leu Thr Arg Ser Pro Val Ile
            20                  25

<210> SEQ ID NO 53
<211> LENGTH: 83
<212> TYPE: DNA
<213> ORGANISM: Oryza sativa

<400> SEQUENCE: 53
ggtgcggcgt cagcgacgtg ttcgcctacc cgggcggcgc gtccatggag atccaccagg      60
cgctgacgcg ctccccggtc atc                                             83
```

METHOD FOR CONVERTING MONOCOT PLANT GENOME SEQUENCE IN WHICH NUCLEIC ACID BASE IN TARGETED DNA SEQUENCE IS SPECIFICALLY CONVERTED, AND MOLECULAR COMPLEX USED THEREIN

CROSS-REFERENCE TO RELATED APPLICATIONS

This patent application is the U.S. national phase of International Patent Application No. PCT/JP2016/085075, filed Nov. 25, 2016, which claims the benefit of Japanese Patent Application No. 2015-232379, filed on Nov. 27, 2015, and Japanese Patent Application No. 2016-134613, filed on Jul. 6, 2016, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 136,025 bytes ASCII (Text) file named "739396ReplacementSequenceListing.txt," created Dec. 3, 2018.

TECHNICAL FIELD

The present invention relates to a modification method of a genome sequence, which enables modification of a nucleic acid base in a particular region of a monocot genome, without cleaving double-stranded DNA, i.e., with no cleavage or single strand cleavage, and a complex of a nucleic acid sequence-recognizing module and a nucleic acid base converting enzyme to be used therefor.

BACKGROUND ART

Monocots are a group of plants characterized by having one cotyledon among angiosperms, and the three major grains of rice, wheat and corn are classified in this. Therefore, molecular breeding of monocots has been studied extensively. However, since monocots are not hosts of *Agrobacterium*, *Agrobacterium* method, which is the most general plant transformation method, could not be utilized for a long time, and a direct introduction method has been used. In the mid 1990's, it was reported that rice can be transformed efficiently by infecting cells active in cell division with *Agrobacterium*. Since then, molecular breeding of monocots by transgene has greatly advanced.

In recent years, genome editing is attracting attention as a technique for modifying the object gene and genome region in various species. Conventionally, as a method of genome editing, a method utilizing an artificial nuclease comprising a molecule having a sequence-independent DNA cleavage ability and a molecule having a sequence recognition ability in combination has been proposed (non-patent document 1).

For example, a method of performing recombination at a target gene locus in DNA in a plant cell or insect cell as a host, by using a zinc finger nuclease (ZFN) wherein a zinc finger DNA binding domain and a non-specific DNA cleavage domain are linked (patent document 1), a method of cleaving or modifying a target gene in a particular nucleotide sequence or a site adjacent thereto by using TALEN wherein a transcription activator-like (TAL) effector which is a DNA binding module that the plant pathogenic bacteria *Xanthomonas* has, and a DNA endonuclease are linked (patent document 2), a method utilizing CRISPR-Cas9 system wherein DNA sequence CRISPR (Clustered Regularly interspaced short palindromic repeats) that functions in an acquired immune system possessed by eubacterium and archaebacterium, and nuclease Cas (CRISPR-associated) protein family having an important function along with CRISPR are combined (patent document 3) and the like have been reported. Recently, moreover, Cpf1 has been reported as a new endonuclease of the CRISPR-Cas system (non-patent document 2). Furthermore, a method of cleaving a target gene in the vicinity of a particular sequence, by using artificial nuclease wherein a PPR protein constituted to recognize a particular nucleotide sequence by a continuation of PPR motifs each consisting of 35 amino acids and recognizing one nucleic acid base, and nuclease are linked (patent document 4) has also been reported.

These genome editing techniques basically assume DNA double-stranded breaks (DSB) by nuclease. However, since DSB involves an unexpected genome modification, side effects such as strong cytotoxicity and chromosomal translocation and the like occur. In addition, there are problems that the number of viable cells is extremely small and genetic modification itself is difficult depending on the cell type.

In response to the above-mentioned problems, the present inventors have reported that genome sequence was successfully modified without involving DSB in various organisms including yeast and *Escherichia coli* by nucleobase conversion in a region containing a specific DNA sequence, by introducing, into a host cell, a complex in which a deaminase catalyzing a deamination reaction is linked to a molecule having a DNA sequence recognizing ability (patent document 5).

When this method is applied to higher plants such as monocots, to further improve mutation introduction efficiency, it is desirable to further optimize the constitution of the molecular complex to be introduced and the culture conditions and the like of the plant cells after introduction. In yeast and prokaryotes, the mutation mode is mainly base substitution, as expected from the use of deaminase, and the frequency of insertion/deletion mutation is low. Therefore, the development of a technique by which different types of mutations are efficiently introduced is also desired.

DOCUMENT LIST

Patent Documents patent document 1: JP-B-4968498
patent document 2: National Publication of International Patent Application No. 2013-513389
patent document 3: National. Publication of International Patent Application No. 2010-519929
patent document 4: JP-A-2013-128413
patent document 5: WO 2015/133554

Non-Patent Documents non-patent document 1: Kelvin M Esvelt, Harris H Wang (2013) Genome-scale engineering for systems and synthetic biology, Molecular Systems Biology 9: 641
non-patent document 2: Bernd Zetsche et al. (2015) Cpf1 Is a Single RNA-Guided Endonuclease of a Class 2 CRISPR-Cas System, Cell 163: 759-771

SUMMARY OF THE INVENTION

Problems to be Solved by the Invention

Therefore, a first object of the present invention is to provide a novel method of genome editing for efficiently modifying a nucleic acid base of a particular sequence of a monocot genome gene without DSB, i.e., by non-cleavage of a double stranded DNA or single strand cleavage, and a more preferable complex of a nucleic acid sequence-recognizing module and a nucleic acid base converting enzyme used therefor. In addition, a second object of the present invention is to provide a means capable of efficiently introducing mutations into a host cell in a manner different from base substitution in genome editing unaccompanied by DSB using deaminase.

Means of Solving the Problems

To achieve the above-mentioned first object, the present inventors first combined targeting vector pZH_OsU6 gRNA_MMCas9 (Plant Mol Biol (2015) 88:561-572) optimized for rice in CRISPR/Cas9 system as artificial nuclease, and deaminase (see FIG. 1B). That is, a mutation that inactivates cleavage ability of both or one of the strands of the target DNA is introduced into the Cas9 coding sequence (OsCas9) optimized for the use of codon of rice in the above-mentioned targeting vector, and the coding sequence was fused with a cytidine deaminase coding sequence (AtPmCDA) optimized for the use of plant codon. Given a hypothesis that the transfer efficiency of Cas9/deaminase fusion protein synthesized in the cytoplasm so into the nucleus may decrease because plant cells have a larger cell size than yeast and the like, a nuclear localization signal (NLS) was added not only to the upstream of Cas9 but also to both terminals of deaminase. As a result of introduction of the improved vector into rice callus, the object base in the target nucleotide sequence could be successfully substituted by other base. More surprisingly, it was clarified that, when Cas9 (D10A) in which the cleavage ability of one strand of the target DNA is inactivated (having nickase activity) was used, deletion mutation mainly occurs in the region centered on the base deaminated by deaminase.

In addition, the present inventors have succeeded in further improving the efficiency of mutation introduction by culturing gene-introduced rice callus at a temperature lower than the culture temperature normally used in the selection step of the mutation-introduced strain.

The present inventor have conducted further studies based on these findings and completed the present invention.

Therefore, the present invention provides the following.
[1] A method of modifying a targeted site of a double stranded DNA of a monocot cell, comprising a step of contacting a complex wherein a nucleic acid sequence-recognizing module that specifically binds to a target nucleotide sequence in the given double stranded DNA and a nucleic acid base converting enzyme are bonded, with said double stranded DNA, to convert one or more nucleotides in the targeted site to other one or more nucleotides or delete one or more nucleotides, or insert one or more nucleotides into said targeted site, without cleaving at least one strand of said double stranded DNA in the targeted site, wherein the double stranded DNA is contacted with the complex by introducing a nucleic acid encoding the complex into the monocot cell and culturing the monocot cell to intracellularly express the complex.
[2] The method of the above-mentioned [1], wherein the aforementioned culture step is at least partly performed at a temperature lower than the optimal culture temperature of the monocot cell.
[3] The method of the above-mentioned [1] or [2], wherein the aforementioned nucleic acid sequence-recognizing module is selected from the group consisting of a CRISPR-Cas system wherein at least one DNA cleavage ability of Cas is inactivated, a zinc finger motif, a TAL effector and a PPR motif.
[4] The method of the above-mentioned [1] or [2], wherein the aforementioned nucleic acid sequence-recognizing module is a CRISPR-Cas system wherein at least one DNA cleavage ability of Cas is inactivated.
[5] The method of the above-mentioned [4], wherein the aforementioned nucleic acid sequence-recognizing module is a CRISPR-Cas system in which a cleavage ability of an opposite strand of the strand forming a complementary strand with a guide RNA is inactivated.
[6] The method of the above-mentioned [5], wherein one or more nucleotides of the targeted site are deleted.
[7] The method of any of the above-mentioned [1] to [6], wherein the aforementioned nucleic acid base converting enzyme is deaminase.
[8] The method of the above-mentioned [7], wherein the aforementioned deaminase is cytidine deaminase.
[9] The method of the above-mentioned [8], wherein the aforementioned cytidine deaminase is PmCDA1 derived from *Petromyzon marinus*.
[10] The method of any of the above-mentioned [1] to [9], wherein the nucleic acid sequence encoding the nucleic acid sequence-recognizing module and the nucleic acid base converting enzyme is optimized for use of a codon of angiosperm or monocot.
[11] The method of any of the above-mentioned [1] to [10], wherein the nuclear localization signal is added to the both terminals of the nucleic acid sequence-recognizing module and nucleic acid base converting enzyme.
[12] The method of any of the above-mentioned [1] to [11], wherein the monocot is rice, wheat or corn.
[13] The method of the above-mentioned [12], wherein the monocot is rice.
[14] A nucleic acid-modifying enzyme complex wherein a nucleic acid sequence-recognizing module that specifically binds to a target nucleotide sequence in a double stranded DNA of a monocot cell and a nucleic acid base converting enzyme are bonded, which functions in the monocot cell and converts one or more nucleotides in the targeted site to other one or more nucleotides or deletes one or more nucleotides, or inserts one or more nucleotides into said targeted site, without cleaving at least one strand of said double stranded DNA in the targeted site.
[15] The nucleic acid modification enzyme complex of the above-mentioned [14], wherein the nucleic acid sequence-recognizing module is a CRISPR-Cas system in which at least one DNA cleavage ability of Cas is inactivated and the nucleic acid base converting enzyme is cytidine deaminase.
[16] The nucleic acid modification enzyme complex of the above-mentioned [14] or [15], wherein a nuclear localization signal is added to the both terminals of the nucleic acid sequence-recognizing module and nucleic acid base converting enzyme.
[17] A nucleic acid encoding the nucleic acid modification enzyme complex of any of the above-mentioned [14] to [16].
[18] The nucleic acid of the above-mentioned [17], wherein the nucleic acid sequence encoding the nucleic acid sequence-recognizing module and the nucleic acid base converting enzyme is optimized for use of a codon of angiosperm or monocot.

Effect of the Invention

According to the genome editing technique of the present invention, since it does not accompany cleavage of a DNA double strand, the technique is superior in safety, and genetic modification of monocot with a high mutation introduction efficiency becomes possible.

BRIEF DESCRIPTION OF THE DRAWINGS

FIG. 4 shows EGFP expression of a double transformant clone No. 6 obtained by introducing pRIT3-mEGFP and 2409.

FIG. 5 shows EGFP expression of a double transformant clone No. 3 obtained by introducing pRIT3-mEGFP and 2409.

Figure 6:
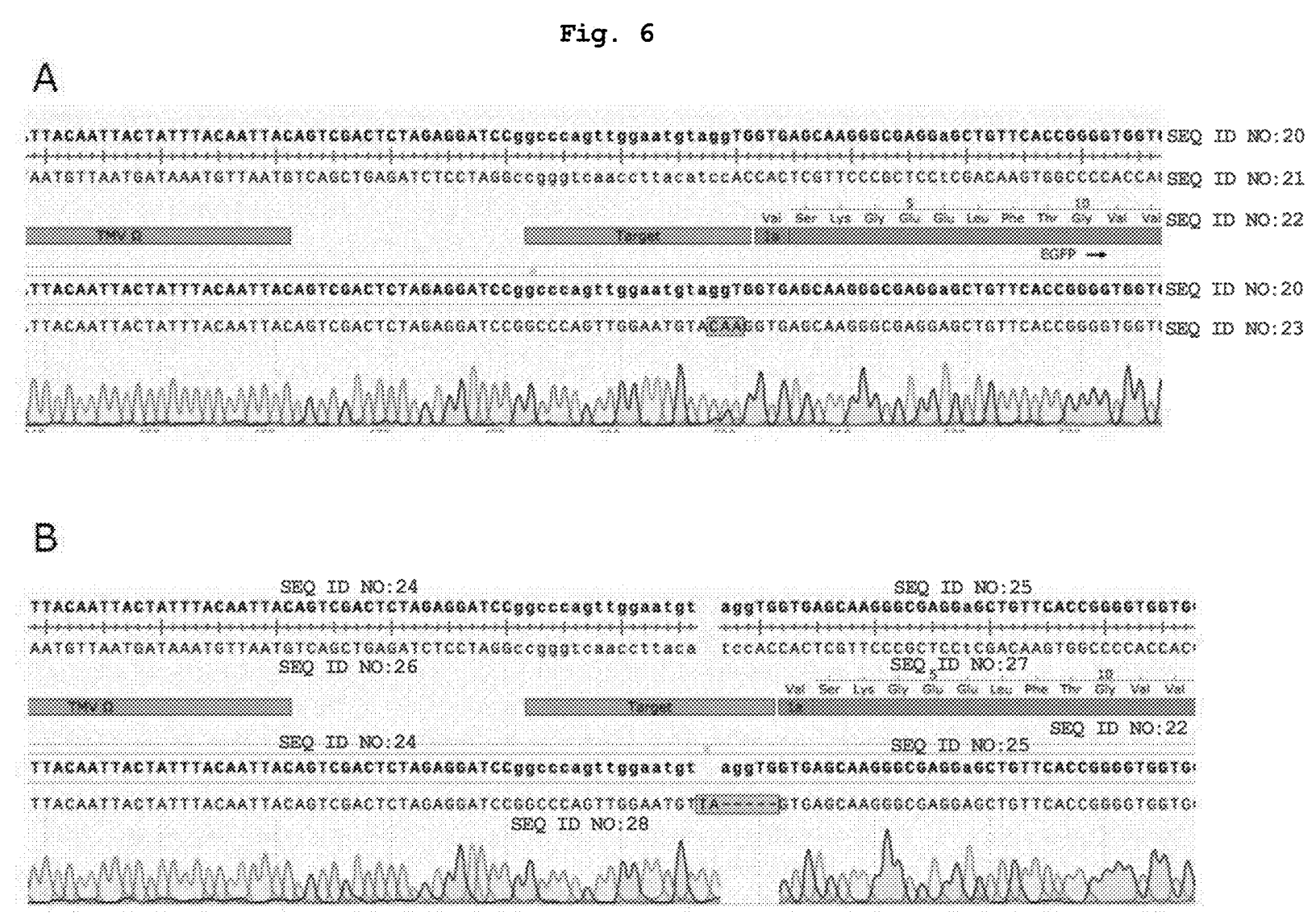

FIG. 6 shows the analysis results of the sequence in the vicinity of the target nucleotide sequence in two kinds of double transformant clones (A and B) obtained by introducing pRIT3-mEGFP and 2409.

Figure 7:
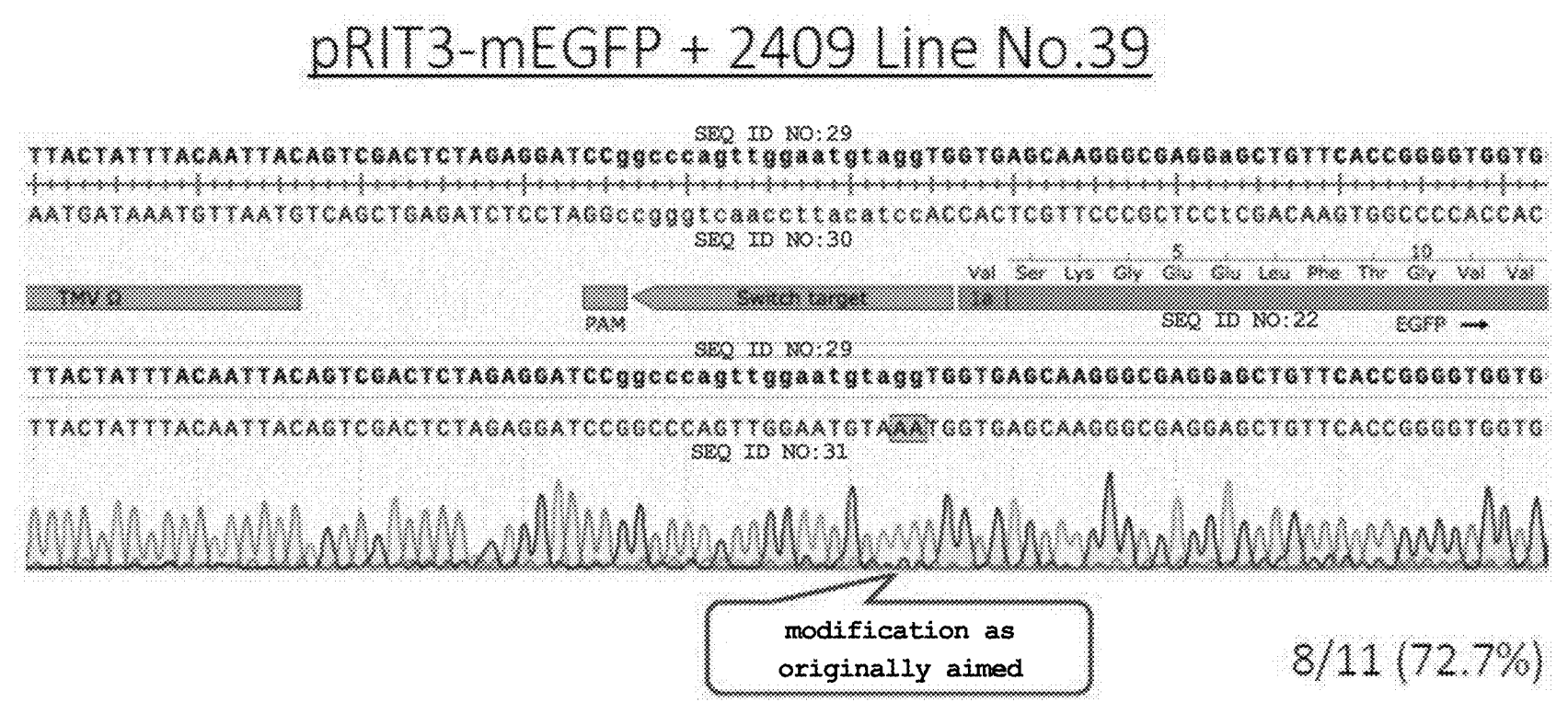

FIG. 7 shows the analysis results of the sequence in the vicinity of the target nucleotide sequence in a double transformant clone No. 39 obtained by introducing pRIT3-mEGFP and 2409.

FIG. 8 shows the analysis results of the sequence in the vicinity of the target nucleotide sequence in a double transformant clone No. 1 obtained by introducing pRIT3-mEGFP and 2408.

FIG. 9 shows the analysis results of the sequence in the vicinity of the target nucleotide sequence in a double transformant clone No. 2 obtained by introducing pRIT3-mEGFP and 2408.

FIG. 10 shows the analysis results of the sequence in the vicinity of the target nucleotide sequence in a double transformant clone No. 4 obtained by introducing pRIT3-mEGFP and 2408.

FIG. 11 shows the analysis results of the sequence in the vicinity of the target nucleotide sequence in subclone No. 1D (GFP signal negative) of a double transformant clone No. 1 obtained by introducing pRIT3-mEGFP and 2408.

FIG. 12 shows the evaluation results of effective concentration of Imazamox relative to rice callus. The upper panel is a photograph on the day of inoculation of rice callus to an Imazamox-added medium and the lower panel is a photograph after 28 days of culture.

FIG. 13 shows schematic drawings of the expression vectors of wild-type ALS and mutation-type ALS A96V used for an Imazamox resistance imparting test.

FIG. 17 shows that the T0 plant body redifferentiated from rice ALS A96V modification callus by Target-AID retains the same ALS genetic modification as the original callus.

DESCRIPTION OF EMBODIMENTS

Figure 1:
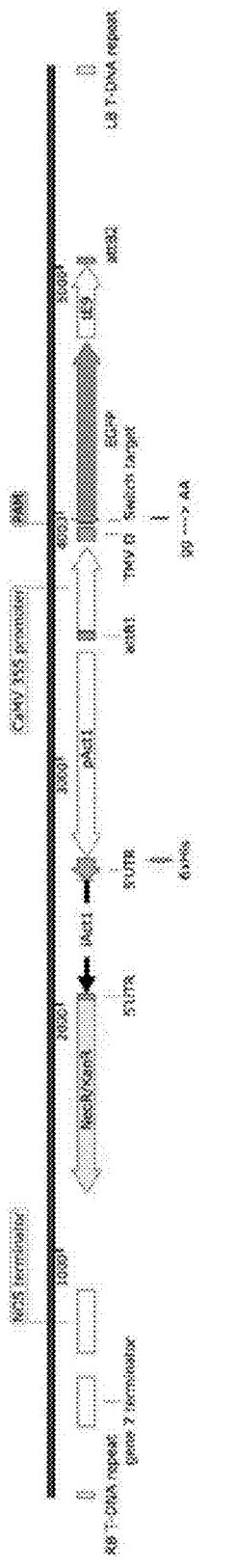
FIG. 1 schematically shows the structure of the vector plasmid used in the Examples. A: vector for Target-AID evaluation. B: Target-AID vector.

The present invention provides a method of modifying a targeted site of a double stranded DNA by converting the target nucleotide sequence and nucleotides in the vicinity thereof in the double stranded DNA to other nucleotides, without cleaving the double stranded DNA to be modified in a monocot cell (hereinafter to be also referred to as "the method of the present invention"). The method characteristically contains a step of contacting a complex wherein a nucleic acid sequence-recognizing module that specifically binds to the target nucleotide sequence in the double stranded DNA and a nucleic acid base converting enzyme are contacted with the double stranded DNA in the host monocot cell to convert etc. the targeted site, i.e., the target nucleotide sequence and nucleotides in the vicinity thereof, to other nucleotides.

While the monocot usable for the method of the present invention is not particularly limited, it is, for example, grain such as rice, wheat, corn, barley, rye and the like or a garden plant such as lily or the like, more preferably rice, wheat or corn, particularly preferably rice.

In the present invention, the "modification" of a double stranded DNA means that a nucleotide (e.g., dC) on a DNA strand is converted to other nucleotide (e.g., dT, dA or dG), or deleted, or a nucleotide or a nucleotide sequence is inserted between certain nucleotides on a DNA strand. While the double stranded DNA to be modified is not particularly limited as long as it is a double stranded DNA present in the host cell, it is preferably a genomic DNA, particularly nuclear genomic DNA. The "targeted site" of a double stranded DNA means the whole or partial "target nucleotide sequence", which a nucleic acid sequence-recognizing module specifically recognizes and binds to, or the vicinity of the target nucleotide sequence (one or both of 5' upstream and 3' downstream). In addition, the "target nucleotide sequence" means a sequence to which a nucleic acid sequence-recognizing module in a double stranded DNA binds.

In the present invention, the "nucleic acid sequence-recognizing module" meats a molecule or molecule complex having an ability to specifically recognize and bind to a particular nucleotide sequence (i.e., target nucleotide sequence) on a DNA strand. Binding of the nucleic acid sequence-recognizing module to a target nucleotide sequence enables a nucleic acid base converting enzyme linked to the module to specifically act on a targeted site of a double stranded DNA.

In the present invention, the "nucleic acid base converting enzyme" means an enzyme capable of converting a target nucleotide to other nucleotide by catalyzing a reaction for converting a substituent on a purine or pyrimidine ring on a DNA base to other group or atom, without cleaving the DNA strand.

In the present invention, the "nucleic acid-modifying enzyme complex" means a molecular complex comprising a complex comprising the above-mentioned nucleic acid sequence-recognizing module and nucleic acid base converting enzyme are connected, and having nucleic acid base converting enzyme activity and imparted with a particular nucleotide sequence recognition ability. The "complex" here encompasses not only one constituted of multiple molecules, but also one having a nucleic acid sequence-recognizing module and a nucleic acid base converting enzyme in a single molecule, like a fusion protein.

The nucleic acid base converting enzyme to be used for the method of the present invention is not particularly limited as long as it can catalyze the above-mentioned reaction, and examples thereof include deaminase belonging to the nucleic acid/nucleotide deaminase superfamily, which catalyzes a deamination reaction that converts an amino group to a carbonyl group. Preferable examples thereof include cytidine deaminase capable of converting cytosine or 5-methylcytosine to uracil or thymine, respectively, adenosine deaminase capable of converting adenine to hypoxanthine, guanosine deaminase capable of converting guanine to xanthine and the like. As cytidine deaminase, more preferred is activation-induced cytidine deaminase (hereinafter to be also referred tows AID) which is an enzyme that introduces a mutation into an immunoglobulin gene in the acquired immunity of vertebrata or the like.

While the derivation of nucleic acid base converting enzyme is not particularly limited, for example, when it is cytidine deaminase, PmCDA1 (*Petromyzon marinus* cytosine deaminase 1) derived from *Petromyzon marinus*, or AID (Activation-induced cytidine deaminase; AICDA) derived from vertebrate (e.g., mammal such as human, swine, bovine, dog, chimpanzee and the like, birds such as chicken and the like, amphibian such as xenopus and the like, fish such as zebrafish, sweetfish, channel catfish and the like) can be used.

A target nucleotide sequence in a double stranded DNA to be recognized by the nucleic acid sequence-recognizing module in the nucleic acid-modifying enzyme complex of the present invention is not particularly limited as long as the module specifically binds to, and may be any sequence in the double stranded DNA. The length of the target nucleotide sequence only needs to be sufficient for specific binding of the nucleic acid sequence-recognizing module. For example, it is not less than 12 nucleotides, preferably not less than 15 nucleotides, more preferably not less than 18 nucleotides, according to the genome size of monocot. While the upper limit of the length is not particularly limited, it is preferably not more than 25 nucleotides, more preferably not more than 22 nucleotides.

As the nucleic acid sequence-recognizing module in the nucleic acid-modifying enzyme complex of the present invention, CRISPR-Cas system wherein at least one DNA cleavage ability of Cas is inactivated (CRISPR-mutant Cas), zinc finger motif, TAL effector and PPR motif and the like, as well as a fragment containing a DNA binding domain of a protein that specifically binds to DNA, such as restriction enzyme, transcription factor, RNA polymerase and the like, and free of a DNA double strand cleavage ability and the like can be used, but the module is not limited thereto. Preferably, CRISPR-mutant Cas, zinc finger motif, TAL effector, PPR motif and the like can be mentioned.

A zinc finger motif is constituted by linkage of 3-6 different Cys2His2 type zinc finger units (1 finger recognizes about 3 bases), and can recognize a target nucleotide sequence of 9-18 bases. A zinc finger motif can be produced by a known method such as Modular assembly method (Nat Biotechnol (2002) 20: 135-141), OPEN method (Mol Cell (2008) 31: 294-301), CoDA method (Nat Methods (2011) 8: 67-69), *Escherichia coli* one-hybrid method (Nat Biotechnol (2008) 26:695-701) and the like. The above-mentioned patent document 1 can be referred to as for the detail of the zinc finger motif production.

A TAL effector has a module repeat structure with about 34 amino acids as a unit, and the 12th and 13th amino acid residues (called RVD) of one module determine the binding stability and base specificity. Since each module is highly independent, TAL effector specific to a target nucleotide sequence can be produced by simply connecting the module. For TAL effector, a production method utilizing an open resource (REAL method (Curr Protoc Mol Biol (2012) Chapter 12: Unit 12.15), FLASH method (Nat Biotechnol (2012) 30: 460-465), and Golden Gate method (Nucleic Acids Res (2011) 39: e82) etc.) have been established, and a TAL effector for a target nucleotide sequence can be designed comparatively conveniently. The above-mentioned patent document 2 can be referred to as for the detail of the production of TAL effector.

PPR motif is constituted such that a particular nucleotide sequence is recognized by a continuation of PPR motifs each consisting of 35 amino acids and recognizing one nucleic acid base, and recognizes a target base only by 1, 4 and ii(-2) amino acids of each motif. Motif constitution has no dependency, and is free of interference of motifs on both sides. Therefore, like TAL effector, a PPR protein specific to the target nucleotide sequence can be produced by simply connecting PPR motifs. The above-mentioned patent document 4 can be referred to as for the detail of the production of PPR motif.

When a fragment of restriction enzyme, transcription factor, RNA polymerase and the like is used, since the DNA binding domains of these proteins are well known, a fragment containing the domain and free of a DNA double strand cleavage ability can be easily designed and constructed.

Any of the above-mentioned nucleic acid sequence-recognizing module can be provided as a fusion protein with the above-mentioned nucleic acid base converting enzyme, or a protein binding domain such as SH3 domain, PDZ domain, GK domain, GB domain and the like and a binding partner thereof may be fused with a nucleic acid sequence-recognizing module and a nucleic acid base converting enzyme, respectively, and provided as a protein complex via an interaction of the domain and a binding partner thereof. Alternatively, a nucleic acid sequence-recognizing module and a nucleic acid base converting enzyme may be each fused with intein, and they can be linked by ligation after protein synthesis.

The nucleic acid-modifying enzyme complex of the present invention containing a complex (including fusion protein) wherein a nucleic acid sequence-recognizing module and a nucleic acid base converting enzyme are bonded may be contacted with a double stranded DNA. A nucleic acid encoding the complex is introduced into a monocot cell having the object double stranded DNA (e.g., nuclear genomic DNA).

Therefore, the nucleic acid sequence-recognizing module and the nucleic acid base converting enzyme are prepared as a nucleic acid encoding a fusion protein thereof, or in a form capable of forming a complex in a host cell after translation into a protein by utilizing a binding domain, intein and the like, or as a nucleic acid encoding each of them. The nucleic acid here may be a DNA or an RNA, preferably DNA. When it is a DNA, it is preferably a double stranded DNA, and provided in the form of an expression vector disposed under regulation of a functional promoter in a host cell.

Since the complex of the present invention wherein a nucleic acid sequence-recognizing module and a nucleic acid base converting enzyme are bonded does not accompany double-stranded DNA breaks (DSB), genome editing with low toxicity is possible, and the genetic modification method of the present invention can be applied to a wide range of monocots in general.

A DNA encoding a nucleic acid sequence-recognizing module such as zinc finger motif, TAL effector, PPR motif and the like can be obtained by any method mentioned above for each module. A DNA encoding a sequence-recognizing module of restriction enzyme, transcription factor, RNA polymerase and the like can be cloned by, for example, synthesizing an oligoDNA primer covering a region encoding a desired part of the protein (part containing DNA binding domain) based on the cDNA sequence information thereof, and amplifying by the RT-PCR method using, as a template, the total RNA or mRNA fraction prepared from the protein-producing cells.

A DNA encoding a nucleic acid base converting enzyme can also be cloned similarly by synthesizing an oligoDNA primer based on the cDNA sequence information thereof, and amplifying by the RT-PCR method using, as a template, the total RNA or mRNA fraction prepared from the enzyme-producing cells. For example, a DNA encoding PmCDA1 of Petromyzon marinus can be cloned by designing suitable primers for the upstream and downstream of CDS based on the cDNA sequence (accession No. EF094822) registered in the NCBI database, and cloning from Petromyzon marinus-derived mRNA by the RT-PCR method. A DNA encoding human AID can be cloned by designing suitable primers for the upstream and downstream of CDS based on the cDNA sequence (accession No. AB040431) registered in the NCBI database, and cloning from, for example, human lymph node-derived mRNA by the RT-PCR method. An AID homologue derived from other vertebrata can also be cloned in the same manner as above based on known cDNA sequence information (e.g., swine (accession No. CU582981), bovine (accession No. NM_110138682), dog (accession No. NM_001003380), chimpanzee (accession No. NM_001071809), chicken (accession No. NM_001243222), xenopus (accession No. NM_001095712), zebrafish (accession No. AAI62573), sweetfish (accession No. AB619797), channel catfish (accession No. NM_001200185) etc.).

The cloned DNA may be directly, or after digestion with a restriction enzyme when desired, or after addition of a suitable linker and/or a nuclear localization signal (each oraganelle transfer signal when the object double stranded DNA is mitochondria or chloroplast DNA), ligated with a DNA encoding a nucleic acid sequence-recognizing module to prepare a DNA encoding a fusion protein. In a preferable embodiment, DNA sequence encoding an oraganelle transfer signal such as nuclear localization signal and the like is desirably added to the both terminals of a DNA encoding a nucleic acid sequence-recognizing module and a DNA encoding a nucleic acid base converting enzyme. Since monocot cells are larger in size as compared to yeast cells, the distance between the cytoplasm where the protein is synthesized and the nucleus increases. Therefore, to efficiently transport a protein molecule with a large molecular weight such as a complex of a nucleic acid sequence-recognizing module and a nucleic acid base converting enzyme to the nucleus, a nuclear localization signal is preferably added to both the nucleic acid sequence-recognizing module and the nucleic acid base converting enzyme. When the nucleic acid sequence-recognizing module and the nucleic acid base converting enzyme are expressed as a fusion protein, a nuclear localization signal can be added to the both terminals of the fusion protein, and between the nucleic acid sequence-recognizing module and the nucleic acid base converting enzyme. The nuclear localization signal is not particularly limited as long as it functions in monocot. For example, SV40-derived nuclear localization signal (PKKKRKV; SEQ ID NO: 6) can be mentioned.

Alternatively, a DNA encoding a nucleic acid sequence-recognizing module, and a DNA encoding a nucleic acid base converting enzyme may be each fused with a DNA encoding a binding domain or a binding partner thereof, or both DNAs may be fused with a DNA encoding a separation intein, whereby the nucleic acid sequence-recognizing conversion module and the nucleic acid base converting enzyme are translated in a host cell to form a complex. In these cases, a linker and/or a nuclear localization signal can be linked to a suitable position of one of or both DNAs when desired.

A DNA encoding a nucleic acid sequence-recognizing module and a DNA encoding a nucleic acid base converting enzyme can be obtained by chemically synthesizing the DNA strand, or by connecting synthesized partly overlapping oligoDNA short strands by utilizing the PCR method and the Gibson Assembly method to construct a DNA encoding the full length thereof. The advantage of constructing a full-length DNA by chemical synthesis or a combination of PCR method or Gibson Assembly method is that the codon to be used can be designed in CDS full-length according to the host into which the DNA is introduced. In the expression of a heterologous DNA, the protein expression level is expected to increase by converting the DNA sequence thereof to a codon highly frequently used in the host organism. As the data of codon use frequency in host to be used, for example, the genetic code use frequency database (http://www.kazusa.or.jp/codon/index.html) disclosed in the home page of Kazusa DNA Research Institute can be used, or documents showing the codon use frequency in each host may be referred to. By reference to the obtained data and the DNA sequence to be introduced, codons showing low use frequency in the host from among those used for the DNA sequence may be converted to a codon coding the same amino acid and showing high use frequency. For example, when the host cell is a rice cell, nucleic acid sequence-recognizing module and/or nucleic acid base converting enzyme coding sequence optimized for codon usage in monocot such as rice and the like, or angiosperm plants in general such as Arabidopsis thaliana and the like can be used. For example, as a PmCDA1 DNA using codon suitable for expression in angiosperm, a DNA having a nucleotide sequence shown by SEQ ID NO: 1 can be mentioned.

An expression vector containing a DNA encoding a nucleic acid sequence-recognizing module and/or a nucleic acid base converting enzyme can be produced, for example, by linking the DNA to the downstream of a promoter functionable in monocot cell in an expression vector containing the promoter.

A vector replicatable in a monocot cell is not particularly limited as long as it has a replication origin (e.g., ori of Ti plasmid, Ri plasmid etc.) that functions in a monocot cell. It preferably also contains a replication origin of Escherichia coli (e.g., ColE1 ori etc.). When an Agrobacterium method is used as a gene transfer method, it is necessary to further contain a T-DNA fragment (including boundary sequences RB and LB) from which a pathogenic gene of Ti plasmid, Ri plasmid has been removed. Examples thereof include, but are not limited to, pBIN193-derived pBI101, pBI121 (Clontech) and improved vector using same as a backbone (e.g., pRI909, pRI910, pRI101, pRI201 (Takara Bio Inc.) etc.).

As the promoter, any promoter capable of functioning in a monocot cell can be used. In a conventional method using DSB, since the survival rate of the host cell sometimes decreases markedly due to the toxicity, it is desirable to increase the number of cells by the start of the induction by using an inductive promoter (e.g., PR1α gene promoter induced by injury, salicylic acid treatment, rd29A gene promoter induced by drying, low temperature, abscisic acid treatment, GST-27 gene promoter induced by dichlormid treatment etc.). However, since sufficient cell proliferation can also be afforded by expressing the nucleic acid-modifying enzyme complex of the present invention, a constitution promoter can also be used without limitation. As the constituent promoter, cauliflower mosaic virus (CaMV) 35S promoter, CaMV19S promoter, nopaline synthetase (NOS) promoter, parsley-derived ubiquitin promoter (Pcubi4-2) and the like can be mentioned. These promoters or fragments thereof linked in tandem (e.g., 2×35S) can also be used.

The expression vector can contain, when desired, a terminator (e.g., NOS terminator, *Pisum sativum* rbcS3A terminator, heat shock protein (HSP) 17.3 terminator etc.), a translation enhancer (e.g., rice-derived alcoholdehydrogenase 5' untranslated region (Os ADH-5'UTR), CaMV or tobacco mosaic virus (TMV)-derived Ω sequence etc.), 3' regulatory region (e.g., rice-derived actin gene (Act1) 3'UTR etc.), polyA-added signal, selection marker of drug resistance gene (e.g., G418 resistance gene (nPtII), hygromycin resistance gene (hpt) etc.) and the like.

An RNA encoding a nucleic acid sequence-recognizing module and/or a nucleic acid base converting enzyme can be prepared by, for example, transcription to mRNA in a vitro transcription system known per se by using a vector encoding DNA encoding the above-mentioned nucleic acid sequence-recognizing module and/or a nucleic acid base converting enzyme as a template.

A complex of a nucleic acid sequence-recognizing module and a nucleic acid base converting enzyme can be intracellularly expressed by introducing an expression vector containing a DNA encoding a nucleic acid sequence-recognizing module and/or a nucleic acid base converting enzyme into a host monocot cell, and culturing the host cell.

As the monocot cell to be a host, suspend cultured cells, callus, protoplast, leaf segment, root segment, seed (immature embryo etc.) and the like prepared from grain such as rice, wheat, corn, barley, rye and the like, flowering garden plants such as lily and the like, and the like are used.

The monocot cell may be haploid (monoploid), or polyploid (e.g., diploid, triploid, tetraploid and the like). In the conventional mutation introduction methods, mutation is, in principle, introduced into only one homologous chromosome to produce a hetero gene type. Therefore, desired phenotype is not expressed unless dominant mutation occurs, and homozygousness inconveniently requires labor and time. In contrast, according to the present invention, since mutation may be introduced into any allele on the homologous chromosome in the genome, desired phenotype can be expressed in a single generation even in the case of recessive mutation, and the problem of the conventional method can be solved.

An expression vector can be introduced into a suitable tissue (e.g., callus, root, leaf, seed, vegetative point etc.) by a known method (e.g., *Agrobacterium* method, PEG method, electroporation method, the particle gun method etc.) according to the kind of the monocot. For example, in the case of rice, *Agrobacterium* method, whisker direct introduction method and the like are generally used, but the method is not limited thereto. For example, in the case of the *Agrobacterium* method, callus is induced from a rice seed according to a conventional method, an expression cassette of a DNA encoding a nucleic acid sequence-recognizing module and/or a nucleic acid base converting enzyme is incorporated in a T-DNA fragment of an *Agrobacterium* expression vector, the expression vector is introduced into *Agrobacterium*, the *Agrobacterium* is infected with the callus, and the bacteria is eliminated 3 days later. On the other hand, in the case of the whisker direct introduction method, an expression vector is mixed with polyornithine to give a complex, the complex is added together with whisker made of potassium titanate to rice callus, mixed and sonicated.

In the case of wheat and corn, for example, an expression vector can be introduced using immature embryo collected from an immature seed as a plant material and similarly using an *Agrobacterium* method.

When the PEG method or electroporation method is used, protoplast is prepared from an appropriate cell or tissue according to a conventional method, and an expression vector is introduced thereinto. In the case of a particle gun method, an expression vector adsorbed on gold microparticles can be introduced into callus, immature embryo, growth point and the like existing in shoot apex or axillary bud by using a particle gun.

In the particle gun method and *Agrobacterium* method, transgene is often chimeric. Therefore, a sample cell in which the above-mentioned nucleic acid is introduced into the cells of the germ line at a high frequency needs to be used for transformation. For example, embryo, hypocotyl section, embryogenic callus, isolated vegetative point and the like can be mentioned.

A monocot cell introduced with a vector can be cultured according to a known method according to the kind thereof. As a medium to be used for culturing, a solid medium (e.g., agar medium, agarose medium, gellan gum medium etc.) is preferable. The medium preferably contains a carbon source, nitrogen source, inorganic substance and the like necessary for the growth of the transformant. For example, N6 medium, MS medium, LS medium, B5 medium and the like are used as the basal medium. The medium may contain plant growth substances (e.g., auxins, cytokinins etc.) and the like as appropriate. The pH of the medium is preferably about 5-about 8. The culture temperature can be appropriately selected from generally about 20° C.-about 35° C. according to the kind of the monocot cell. For example, rice callus can be cultured at generally 28-33° C., preferably 30-33° C.

As mentioned above, a complex of a nucleic acid sequence-recognizing module and a nucleic acid base converting enzyme, i.e., nucleic acid-modifying enzyme complex, can be expressed intracellularly.

A transformant that stably expresses the introduced nucleic acid sequence-recognizing module and nucleic acid base converting enzyme can be selected by culturing monocot cells on a medium supplemented with a drug corresponding to the selection marker gene (e.g., drug resistance gene such as nptII, hpt and the like) contained in the introduced expression vector and selecting a drug resistance colony. While the period of selective culture is not particularly limited, a drug-resistant colony generally appears in about 3-6 weeks.

When the object mutation introduction can be visualized, for example, when the mutation introduces drug resistance to the monocot cell or changes pigment production ability, it is also possible to directly select a strain introduced with the mutation by using the change in the trait due to the object mutation introduction as an index, without performing the primary screening using the selection marker.

The transformant can be subcultured by a method known per se which is suitable for the culturing. For example, the same method as used for the selective culture of the above-mentioned transformant can be used. By culturing the transformant at a temperature lower than the general temperature (e.g., 20-26° C., preferably about 25° C., for rice callus), mutation introduction efficiency can be increased. While not wishing to be bound by any theory, as one interpretation, since PmCDA1, which is one of the preferable nucleic acid base converting enzymes of the present invention, is derived from *Petromyzon marinus*, which is a poikilotherm, the optimum temperature of activity of PmCDA1 may be lower than about 37° C., the optimum temperature of general enzymes, and therefore, the enzyme activity is considered to increase by low temperature culturing. In one preferable embodiment of the present invention, therefore, PmCDA1 is used as a nucleic acid base converting enzyme and monocot cell introduced with a nucleic acid encoding sequence recognizing module/PmCDA1 complex is cultured at a low temperature.

The mutation introduction efficiency can also be increased by culturing the transformant under higher density conditions than normal (e.g., in the case of rice callus, conditions under which the cells are stressed by a density causing the calluses to come into contact with each other to limit contact with the medium).

Whether mutation has been successfully introduced into the target double-stranded DNA of the transformant can be confirmed by examining phenotype when change of phenotype can be visualized by introducing mutation. However, final confirmation is preferably performed by amplifying a target DNA region containing the target nucleotide sequence by genome PCR and determining the base sequence of the amplified fragment. Even a single transformant clone may have a different mutation introduction manner depending on the cell. For example, when callus is used as a plant material, for example, an operation of suspending the transformed callus in a liquid medium, reseeding same on a solid medium, and confirming the mutation introduction manner of the formed subclone is repeated, whereby a clone having a uniform mutation introduction manner can be obtained.

Transformant clones in which mutation introduction was confirmed can be redifferentiated into plants by a redifferentiation method known per se. when a mutation is introduced into. heterozygosity, an R1 plant obtained by self-pollination of the obtained plant body is further self-pollinated to give an R2 plant, whereby a plant body in which a mutation is homozygously introduced can be obtained.

When a complex of a nucleic acid sequence-recognizing module and a nucleic acid base converting enzyme is expressed by an expression vector introduced into the cell, the nucleic acid sequence-recognizing module specifically recognizes and binds to a target nucleotide sequence in the double stranded DNA (e.g., genomic DNA) of interest and, due to the action of the nucleic acid base converting enzyme linked to the nucleic acid sequence-recognizing module, base conversion occurs in the sense strand or antisense strand of the targeted site or vicinity thereof and a mismatch occurs in the double stranded DNA (e.g., when cytidine deaminase such as PmCDA1, AID and the like is used as a nucleic acid base converting enzyme, cytosine on the sense strand or antisense strand at the targeted site is converted to uracil to cause U:G or G:U mismatch). When the mismatch is not correctly repaired, and when repaired such that a base of the opposite strand forms a pair with a base of the converted strand (T-A or A-T in the above-mentioned example), or when other nucleotide is further substituted (e.g., U→A, G) or when one to several dozen bases are deleted or inserted during repair, various mutations are introduced.

As for zinc finger motif, production of many actually functionable zinc finger motifs is not easy, since production efficiency of a zinc finger that specifically binds to a target nucleotide sequence is not high and selection of a zinc finger having high binding specificity is complicated. While TAL effector and PPR motif have a high degree of freedom of target nucleic acid sequence recognition as compared to zinc finger motif, a problem remains in the efficiency since a large protein needs to be designed and constructed every time according to the target nucleotide sequence.

In contrast, since the CRISPR-Cas system recognizes the object double stranded DNA sequence by a guide RNA complementary to the target nucleotide sequence, any sequence can be targeted by simply synthesizing an oligoDNA capable of specifically forming a hybrid with the target nucleotide sequence.

Therefore, in a more preferable embodiment of the present invention, a CRISPR-Cas system wherein at least one DNA cleavage ability of Cas effector protein is inactivated (CRISPR-mutant Cas) is used as a nucleic acid sequence-recognizing module.

The nucleic acid sequence-recognizing module of the present invention using CRISPR-mutant Cas is provided as a complex of a CRISPR-RNA (crRNA) containing a sequence complementary to a target nucleotide sequence and, if necessary, a trans-activating RNA (tracrRNA) necessary for recruiting a mutant Cas effector protein (optionally provided as a chimera RNA with crRNA when tracrRNA is necessary), and a mutant Cas effector protein. An RNA molecule consisting of crRNA alone or chimeric RNA of crRNA and tracrRNA, which constitutes a nucleic acid sequence-recognizing module in combination with a mutant Cas effector protein, is generically referred to as "guide RNA".

The Cas effector protein to be used in the present invention is not particularly limited as long as it forms a complex with guide RNA, and recognize and bind to the target nucleotide sequence in the object gene and a protospacer adjacent motif (PAM) adjacent thereto. Preferred is Cas9 or Cpf1. Examples of the Cas9 include, but are not limited to, *Streptococcus pyogenes*-derived Cas9 (SpCas9; PAM sequence NGG (N is A, G, T or C, hereinafter the same), *Streptococcus thermophiles*-derived Cas9 (StCas9; PAM sequence NNAGAAW), *Neisseria meningitides*-derived Cas9 (MmCas9; PAM sequence NNNNGATT) and the like. Preferred is SpCas9 with less restriction by PAM (substantially 2 bases, can be targeted almost anywhere on the genome in theory). Examples of the Cpf1 include, but are not limited to, *Francisella novicida*-derived Cpf1 (FnCpf1; PAM sequence NTT), *Acidaminococcus* sp.-derived Cpf1 (AsCpf1; PAM sequence NTTT), Lachnospiraceae bacterium-derived Cpf1 (LbCpf1; PAM sequence NTTT) and the like. As a mutant Cas effector protein (sometimes abbreviated as mutant Cas) to be used in the present invention, any of Cas effector protein wherein the cleavage ability of the both strands of the double stranded DNA is inactivated, or one having nickase activity wherein only one cleavage ability of one strand is inactivated can be used. For example, in the case of SpCas9, a D10A mutant wherein the 10th Asp residue is converted to an Ala residue and lacking cleavage ability of a strand opposite to the strand forming a complementary strand with a guide RNA (therefore, having nickase activity with a strand forming a strand complementary to guide RNA), or H840A mutant wherein the 840th His residue is converted to an Ala residue and lacking cleavage ability of strand forming a strand complementary to guide RNA (therefore, having nickase activity with a strand opposite to a strand forming a strand complementary to guide RNA), or a double mutant thereof (dCas9) can be used, and other mutant Cas can be used similarly. In the case of FnCpf1, a variant lacking cleavage ability of both strands, in which the 917th Asp residue is converted to the Ala residue (D917A) or the 1006th Glu residue is converted to the Ala residue (E1006A), can be used. Other mutant Cas can be similarly used as long as it lacks the cleavage ability of at least one strand of a double-stranded DNA.

A nucleic acid base converting enzyme is provided as a complex with mutant Cas by a method similar to the coupling scheme with the above-mentioned zinc finger and the like. Alternatively, a nucleic acid base converting enzyme and mutant Cas can also be bound by utilizing RNA aptamers MS2F6, PP7 and the like and RNA scaffold by binding proteins thereto. The targeting sequence in the guide RNA forms a complementary strand with the target nucleotide sequence, and mutant Cas is recruited by other region in the guide RNA (that is, sequence other than targeting sequence in crRNA or tracrRNA subsequent to crRNA) and recognizes PAM. One or both DNAs cannot be cleaved, and, due to the action of the nucleic acid base converting enzyme linked to the mutant Cas, base conversion occurs in the targeted site (appropriately adjusted within several hundred bases including whole or partial target nucleotide sequence) and a mismatch occurs in the double stranded DNA. When the mismatch is not correctly repaired, and when repaired such that a base of the opposite strand forms a pair with a base of the converted strand, or when other nucleotide is further converted or when one to several dozen bases are deleted or inserted during repair, various mutations are introduced.

Even when CRISPR-mutant Cas is used as a nucleic acid sequence-recognizing module, a nucleic acid sequence-recognizing module and a nucleic acid base converting enzyme are introduced, in the form of a nucleic acid (preferably DNA) encoding same, into a monocot cell having a double stranded DNA of interest, similar to when zinc finger and the like are used as a nucleic acid sequence-recognizing module.

A DNA encoding Cas effector protein (e.g., Cas9, Cpf1) can be cloned by a method similar to the above-mentioned method for a DNA encoding a nucleic acid base converting enzyme, from a cell producing the enzyme. A mutant Cas can be obtained by introducing a mutation to convert an amino acid residue of the part important for the DNA cleavage activity (e.g., 10th Asp residue and 840th His residue for SpCas9, 917th Asp residue, 1006th Glu residue and the like for FnCpf1, though not limited thereto) to other amino acid, into a DNA encoding cloned Cas, by a site specific mutation induction method known per se.

Alternatively, a DNA encoding mutant Cas can also be constructed as a DNA showing codon usage suitable for expression in a host monocot cell to be used, by a method similar to those mentioned above for a DNA encoding a nucleic acid sequence-recognizing module and a DNA encoding a nucleic acid base converting enzyme, and by a combination of chemical synthesis or PCR method or Gibson Assembly method. For example, as a SpCas9 DNA using a codon suitable for the expression in rice, a DNA having a nucleotide sequence shown in SEQ ID NO: 3 can be mentioned.

A DNA encoding a mutant Cas and a DNA encoding a nucleic acid base converting enzyme may be linked to allow for expression as a fusion protein, or designed to be separately expressed using a binding domain, intein and the like, and form a complex in a host cell via protein-protein interaction and protein ligation. In any case, a DNA encoding mutant Cas and a DNA encoding a nucleic acid base converting enzyme are desirably added, to the both terminals thereof, with a sequence (e.g., SV40-derived NLS coding sequence; SEQ ID NO: 5) encoding a nuclear localization signal (NLS) capable of functioning in a monocot cell. When mutant Cas and a nucleic acid base converting enzyme are expressed as fusion proteins, they can commonly have one NLS sequence as NLS to be added to the C-terminal of one of the proteins and the N-terminal of the other protein. When the CRISPR-Cas technique is applied to an eukaryotic cell, addition of NLS is a conventional means to improve efficiency of nuclear translocation of Cas effector protein. According to the present invention, to express mutant Cas as a complex with a nucleic acid base converting enzyme, the molecular weight becomes large. When a monocot cell having a large size as compared to the yeast cell reported earlier by the present inventor is used as a host, the efficiency of nuclear translocation of the complex may decrease. To improve nuclear translocation efficiency of the complex, the present inventors conceived addition of NLS to the both terminals of the mutant Cas effector protein and the nucleic acid base converting enzyme, whereby high mutation introduction efficiency was successfully obtained even in a monocot cell by using the genome editing technique of the present invention.

The obtained DNA encoding a mutant Cas and/or a nucleic acid base converting enzyme can be inserted into the downstream of a promoter of an expression vector similar to the one mentioned above, for example, CaMV35S promoter, CaMV19S promoter, NOS promoter, Pcubi4-2 promoter, 2×35S promoter and the like. As mentioned above, the expression vector can contain, when desired, a selection marker of a terminator (e.g., NOS terminator, Pisum sativum rbcS3A terminator, heat shock protein (HSP) 17.3 terminator etc.), a translation enhancer (e.g., rice derived from alcoholdehydrogenase 5' untranslated region (Os ADH-5'UTR), Ω sequences derived from CaMV and tobacco mosaic virus (TMV) etc.), 3' regulatory region (e.g., rice derived from actin gene (Act1) 3'UTR etc.), polyA addition signal, drug resistance gene (e.g., G418 resistance gene (nPtII), hygromycin resistance gene (hpt) etc.) and the like. In a preferable embodiment, to enhance translation efficiency in a monocot cell, Os ADH-5'UTR can be inserted in between a promoter and a DNA encoding a mutant Cas and/or nucleic acid base converting enzyme.

On the other hand, a DNA encoding guide RNA can be obtained by designing a coding sequence of a crRNA sequence (e.g., when FnCpf1 is recruited as Cas effector protein, crRNA containing AAUUUCUACUGUU GUAGAU (SEQ ID NO: 7; underlined sequences form base pairs to take a stem-loop structure) at 5'-side of the targeting sequence can be used) comprising a nucleotide sequence (also called "targeting sequence") complementary to the "targeted strand" of the target nucleotide sequence, or an oligo DNA sequence in which a crRNA coding sequence and, if necessary, a known tracrRNA coding sequence (e.g., as tracrRNA coding sequence when Cas9 is recruited as Cas effector protein, gttttagagctagaaatagcaagttaaaataaggct- agtccgttatcaacttgaaaaagtggc accgagtcggtggtgctttt; SEQ ID NO: 8) are linked, and chemically synthesizing by a DNA/RNA synthesizer.

As used herein, the "target strand" means a strand that hybridizes with the crRNA of the target nucleotide sequence, and an opposite strand that becomes single-stranded by hybridization between the target strand and crRNA is to be called a "non-targeted strand". Nucleic acid base conversion reaction is generally assumed to often occur on non-targeted strands that have become single-stranded. Therefore, when the target nucleotide sequence is represented by one strand (e.g., when PAM sequence is indicated, when positional relationship between target nucleotide sequence and PAM is shown etc.), it is represented by the sequence of the non-targeted strand.

While the length of the targeting sequence is not particularly limited as long as it can specifically bind to a target nucleotide sequence, it is, for example, 15-30 nucleotides, preferably 18-25 nucleotides. Selection of the target nucleotide sequence is limited by the presence of adjacent PAM on the 3'-side (in the case of Cas9) or 5'-side (in the case of Cpf1) of the sequence. According to the finding of yeast and the like, in the system of the present invention in which CRISPR-mutant Cas9 and cytidine deaminase are combined, there is regularity that C located within 7 nucleotides in the 3' direction from the 5'-end thereof is easily substituted, regardless of the length of the target nucleotide sequence. Therefore, it is possible to shift the site of the base, into which the mutation can be introduced, by appropriately selecting the length of the target nucleotide sequence (targeting sequence as a complementary strand thereof). As a result, it is possible to at least partially cancel the restriction by PAM (NGG in SpCas9), which further increases the degree of freedom of mutation introduction.

When Cas9 is used as a Cas effector protein, a targeting sequence can be designed by, for example, listing up 20 mer sequences adjacent to PAM (e.g., NGG in the case of SpCas9) on the 3'-side from the CDS sequences of the object gene by using a published guide RNA design website (CRISPR Design Tool, CRISPRdirect etc.), and selecting a sequence that causes amino acid change in the protein encoded by the object gene when C in 7 nucleotides in the 3' direction from the 5'-end thereof is converted to T. Furthermore, when the length of the targeting sequence is changed within the range of, for example, 18-25 nucleotides, a sequence containing C that causes amino acid change by the base conversion within 7 nucleotides in the 3' direction from the 5'-end thereof is similarly selected. From these candidates, a candidate sequence with a small number of off-target sites in the object monocot genome can be used as the targeting sequence. When the guide RNA design software to be used does not have the function to search the off-target site of the monocot genome, the off-target site can be searched for by, for example, applying a Blast search to the monocot genome to be the host for 8 to 12 nucleotides (seed sequence with high discrimination ability of target nucleotide sequence) on the 3'-side of the candidate sequence.

While a DNA encoding guide RNA can also be inserted into an expression vector similar to the one mentioned above, according to the host. As the promoter, pol III system promoter (e.g., SNR6, SNR52, SCR1, RPR1, U3, U6, H1 promoter etc.) and terminator (e.g., poly T sequence ($T_6$ sequence etc.)) are preferably used. For example, when the host cell is a rice cell, rice-derived U6 or U3 promoter, more preferably U6 promoter, can be used. When pol III system promoter is used, a nucleotide sequence with 4 or more consecutive Ts should not be selected as the targeting sequence.

DNA encoding guide RNA (crRNA or crRNA-tracrRNA chimera) can be obtained by designing an oligoDNA sequence linking a sequence complementary to the target strand of the target nucleotide sequence and a known tracrRNA sequence (when Cas9 is recruited) or a direct repeat sequence of crRNA (when Cpf1 is recruited) and chemically synthesizing using a DNA/RNA synthesizer.

A DNA encoding mutant Cas and/or a nucleic acid base converting enzyme and a DNA encoding guide RNA (crRNA or crRNA-tracrRNA chimera) can be introduced into a cell by a method similar to the above, according to the host monocot cell. Selection of transformants stably expressing mutant Cas and nucleic acid base converting enzyme, and maintenance culture of the selected transformants can also be performed in the same manner as described above.

Since conventional artificial nuclease accompanies Double-stranded DNA breaks (DSB), inhibition of growth and cell death assumedly caused by disordered cleavage of chromosome (off-target cleavage) occur by targeting a sequence in the genome. In the present invention, mutation is introduced not by DNA cleavage but by a conversion reaction of the substituent on the DNA base (particularly deamination reaction), and therefore, drastic reduction of toxicity can be realized.

The modification of the double stranded DNA in the present invention does not prevent occurrence of cleavage of the double stranded DNA in a site other than the targeted site (appropriately adjusted within several hundred bases including whole or partial target nucleotide sequence). However, one of the greatest advantages of the present invention is avoidance of toxicity by off-target cleavage. In preferable one embodiment, therefore, the modification of the double stranded DNA in the present invention does not accompany cleavage of DNA strand not only in a targeted site of a given double stranded DNA but in a site other than same.

As shown in the below-mentioned Examples, the tendency of mutation introduction manner differs remarkably between when Cas9 having a nickase activity capable of cleaving only one of the strands of the double stranded DNA is used as a mutant Cas, and when mutant Cas9 incapable of cleaving both strands is used as a mutant Cas. When a D10A mutant that lacks the cleavage ability of the opposite strand (non-targeted strand) of the strand forming a complementary strand with the guide RNA (thus having nickase activity against the target strand) is used as mutant Cas, a deletion mutation of about 1 to 20 nucleotides is more likely to be introduced than base substitution. Deletion often occurs in the region centered on the base substitution site (within 7 nucleotides in the 3' direction from the 5' end of the target nucleotide sequence) than the cleavage site by Cas (2-3 nucleotides upstream of PAM). At the same time as the deletion, insertion of one to several nucleotides may occur. While not wishing to be bound by any theory, in excision repairing nucleotide that has undergone base substitution on a non-targeted strand, elongation reaction is considered to be performed with the opposite strand (target strand) as a template while removing the surrounding bases in monocot. At that time, when the target strand contains nick, it is assumed that the excision repair mechanism works also on the target strand, resulting in a state in which nucleotide falls off in both strands, and forcible ligation occurs without performing normal elongation reaction, as a result of which, deletion mutation is likely to occur.

On the other hand, when mutant Cas9 with uncleavable both strands was used, mutation introduction manner was mainly base substitution as in the case of budding yeast, Escherichia coli and the like. However, the range of the mutation introduction site is somewhat wider than in the case of budding yeast and reaches the upstream of the 5'-terminal of the target nucleotide sequence (e.g., 21 nucleotides upstream of PAM sequence). While not wishing to be bound by any theory, based on the above-mentioned hypothesis, it is assumed that, due to the absence of nick in the target strand, an elongation reaction using the target strand as a template proceeds normally, and the base substitution becomes the main mutation. Similarly, it is assumed that even when H840A mutant lacking cleavage ability of the target strand (thus having nickase activity against non-targeted strand) is used, since an elongation reaction using the opposite target strand as a template proceeds normally, the mutation introduction manner is mainly the base substitution.

Therefore, by appropriately selecting the DNA strand cleavage ability of mutant Cas, base substitution can be introduced into a particular nucleotide or nucleotide region at a pinpoint, or deletion mutation of within about 20 nucleotides centering the base substitution site can be introduced, which can be property adopted according to the object.

The present inventors also confirmed using budding yeast that when sequence-recognizing modules for the adjacent multiple target nucleotide sequences are produced, and simultaneously used, the mutation introduction efficiency drastically increases than using a single nucleotide sequence as a target, and similar effect can also be expected in monocot cells. As the effect thereof, similarly mutation induction is realized even when both target nucleotide sequences partly overlap or when the both are apart by about 600 bp. It can occur both when the target nucleotide sequences are in the same direction (target strand is the same strand), and when they are opposed (target strands are both strands of double stranded DNA).

In addition, modification of multiple DNA regions at completely different positions as targets can be performed. Therefore, in one preferable embodiment of the present invention, two or more kinds of nucleic acid sequence-recognizing modules that specifically bind to different target nucleotide sequences (which may be present in one object gene, or two or more different object genes) can be used. In this case, each one of these nucleic acid sequence-recognizing modules and nucleic acid base converting enzyme form a nucleic acid-modifying enzyme complex. Here, a common nucleic acid base converting enzyme can be used. For example, when CRISPR-Cas system is used as a nucleic acid sequence-recognizing module, a common complex of a Cas effector protein and a nucleic acid base converting enzyme (including fusion protein) is used, and two or more crRNA, or two or more kinds of chimera RNA of each of two or more crRNA and tracrRNA that respectively form a complementary strand with a different target nucleotide sequence are produced and used as guide RNA (crRNA or crRNA-tracrRNA chimera). On the other hand, when zinc finger motif, TAL effector and the like are used as nucleic acid sequence-recognizing modules, for example, a nucleic acid base converting enzyme can be fused with a nucleic acid sequence-recognizing module that specifically binds to a different target nucleotide.

To express the nucleic acid-modifying enzyme complex of the present invention in a monocot cell, as mentioned above, an expression vector containing a DNA encoding the nucleic acid-modifying enzyme complex is introduced into a host cell. For efficient introduction of mutation, it is desirable to maintain an expression of nucleic acid-modifying enzyme complex of a given level or above for not less than a given period. From such aspect, while the expression vector is certainly incorporated into the host genome, since sustained expression of the nucleic acid modification enzyme complex increases the risk of off-target cleavage, it is preferably removed rapidly after successful introduction of mutation. As a means for removing DNA incorporated into the host genome, a method using a Cre-loxP system, a method using a transposon, and the like can be mentioned.

Alternatively, editing of host genome can be efficiently realized while avoiding the risk of off-target cleavage by causing a nucleic acid base conversion reaction in a desired stage, and transiently expressing the nucleic acid-modifying enzyme complex of the present invention in a host cell for a period necessary for fixing the modification of the targeted site. While a period necessary for a nucleic acid base conversion reaction and fixing the modification of the targeted site varies depending on the kind of the host cell, culture conditions and the like, about 2-3 days are considered to be necessary since at least several generations of cell division need to be performed. Those of ordinary skill in the art can appropriately determine a preferable expression induction period based on the culture conditions to be used and the like. The expression induction period of the nucleic acid encoding the nucleic acid-modifying enzyme complex of the present invention may be extended beyond the above-mentioned "period necessary for fixing the modification of the targeted site" as long as the host cell is free of side effects and redifferentiation potency of the host cell can be maintained.

As a means for transiently expressing the nucleic acid-modifying enzyme complex of the present invention at a desired stage for a desired period, a method including producing a construct (expression vector) containing a nucleic acid (a DNA encoding a guide RNA and a DNA encoding a mutant Cas and nucleic acid base substitution enzyme in the CRISPR-Cas system) encoding the nucleic acid-modifying enzyme complex, in a form capable of controlling the expression period, introducing the construct into a monocot cell can be mentioned. The "form capable of controlling the expression period" is specifically, for example, a DNA encoding the nucleic acid-modifying enzyme complex of the present invention placed under regulation of an inducible regulatory region. While the "inducible regulatory region" is not particularly limited, it is, for example, the aforementioned induction promoter (e.g., PR1a gene promoter, rd29A gene promoter, GST-27 gene promoter etc.).

The present invention is explained in the following by referring to Examples, which are not to be construed as limitative.

EXAMPLES

1. Vector Construction (1) Construction of Vector for Target-AID Evaluation pRIT3-EGFP (having EGFP ORF; SEQ ID NO: 9) and pRIT3-mEGFP (having termination codon immediately after EGFP initiation codon; SEQ ID NO: 10) having the structures shown in FIG. 1A were produced by a conventional method.

(2) Construction of Target-AID Vector

Target-AID vector 2408 (encoding dCas9; SEQ ID NO: 11) and 2409 (encoding D10A mutant; SEQ ID NO: 12) having the structures shown in FIG. 1B were produced by substituting OS Opt. Cas9 of pZH_OsU6_gRNA_MMCas9 (Plant Mol Biol (2015) 88:561-572) with DNA encoding mutant Cas9 having H840A and D10A double mutation or D10A mutation alone, and fusing the downstream thereof with DNA encoding PmCDA1 optimized for codon use of *Arabidopsis thaliana* and having a sequence encoding SV40-derived nuclear localization signal (NLS) added to the both terminals.

2. Introduction of Target-AID and Evaluation Vector into *Agrobacterium*

Target-AID vectors 2408 and 2409 (FIG. 1B) and evaluation vectors pRIT3-EGFP and pRIT3-mEGFP (FIG. 1A) were introduced into *Agrobacterium* (*Agrobacterium tumefaciens* EHA101 strain) by electroporation (MicroPulser electroporation system, Bio Rad).

First, a competent cell of *Agrobacterium* was produced by the following procedures.

*Agrobacterium* strain was spread on YEB agar medium (Beef Extract 5 g/L, Yeast Extract 1 g/L, Bacto Pepton 1 g/L, Sucrose 5 g/L, $MgSO_4$ 2 mM, Bacto Agar 12 g (1.2%)), and cultured in a dark place at 28° C. for 2 days. The obtained single colony was inoculated to YEB liquid medium (5 mL) and cultured with shaking in a dark place at 28° C. for 12 hr. The suspension (200 μL) was added to 200 mL of YEB liquid medium and cultured with shaking in a dark place at 28° C. and proliferated to OD600=0.2-0.4. Then, the fungus was centrifuged (3000 rpm, 4° C., 10 min) and harvested, suspended in 20 mL of 10 mM HEPES (pH 8.0), and centrifugation was repeated 2-3 times. The fungus recovered by centrifugation was suspended in a sterile 10% aqueous glycerol solution (2 mL) to give a competent cell. Then, by the procedures shown below, each vector was introduced into *Agrobacterium*. Each vector was dissolved in sterile water at 1 μg/μL concentration, mixed with the above-mentioned *Agrobacterium* suspension (50 μL), transferred to micropulser cuvette (0.1 cm gap, BioRad) and electroporation (2.2 kV, 5.8 ms) was performed. Then, to this liquid was added 800 μL YEB liquid medium and the mixture was cultured in a dark place at 28° C. for 2 hr, spread on YEB agar medium containing 100 mg/L spectinomycin and cultured in a dark place at 28° C. for 36-48 hr. The obtained bacterial colony was proliferated in YEB liquid medium (5 mL) containing 100 mg/L spectinomycin, dispensed to a microtubule as a glycerol (final concentration 35%) stock and preserved at −80° C.

3. Introduction of Target-AID Evaluation Vector into Rice Cultured Cells

Rice was transformed basically according to the method of Terada et al. (Terada, R., Urawa, H., Inagaki, Y., Tsugane, K., and Iida, S. (2002) Efficient gene targeting by homologous recombination in rice. Nat. Biotechnol. 20, 1030-1034).

3-1. Preparation of Rice Callus for Transformation

About 100 seeds of rice (*Oryza sativa*. L Japonica brand; Nipponbare) after chaff removal were shaken in 70% ethanol for 1 min, and sterilized by immersing in 2.5% sodium hypochlorite for 20-30 min. Thereafter, they were rinsed with sterile water inoculated on 2N6 medium (mixed salt for N6 medium (Sigma-Aldrich Co. LLC.) 4.0 g/L, Casamino acid 300 mg/L, Myo-inocitol 100 mg/L, Nicotinic acid 0.5 mg/L, Pyridoxine HCl 0.5 mg/L, Thiamine HCl 0.5 mg/L, L-Proline 2878 mg/L, Sucrose 30.0 g/L, 2,4-D (2,4-dichlorophenoxyacetic acid) 2 mg/L, Gelrite 4.0 g/L, pH 5.8), cultured in a dark place at 31.5° C. for 3 weeks, whereby scutellum cell-derived dedifferentiation cell aggregate (callus) was induced. Thereafter, callus having high cell division activity was selected every month, passage cultured, and callus after 4 months from the start of the culture was used for transformation.

3-2. Preparation of *Agrobacterium* for Transformation

Each *Agrobacterium* bacterial culture into which a vector for Target-AID evaluation was introduced was dissolved on ice, 300 μL thereof was spread on AB medium ($NH_4Cl$ 1 g/L, $MgSO_4.7H_2O$ 3 g/L, KCl 0.15 g/L, $CaCl_2.2H_2O$ 0.012 g/L, $FeSO_4.7H_2O$ 0.0025 g/L, $K_2HPO_4$ 3 g/L, $NaH_2PO_4.H_2O$ 1.15 g/L, Sucrose 5.5 g/L, Agarose 6.0 g/L, pH 7.2) added with 100 mg/L spectinomycin, and cultured in a dark place at 28° C. for 3 days. Thereafter, the proliferated *Agrobacterium* was suspended in AAI liquid medium ($MgSO_4.7H_2O$ 5 g/L, $CaCl_2.2H_2O$ 1.5 g/L, $NaH_2PO_4.H_2O$ 1.5 g/L, KCl 29.5 g/L, $MnSO_4.4H_2O$ 10 g/L, $ZnSO_4.7H_2O$ 2 g/L, $H_3BO_3$ 3 g/L, KI 0.75 g/L, $Na_2MoO_4.2H_2O$ 0.25 g/L, $CoCl_2.6H_2O$ 25 mg/L, $CuSO_4.5H_2O$ 25 mg/L, $FeSO_4.7H_2O$ 13.9 g/L, $Na_2$ EDTA 18.7 g/L, Myo-inocitol 100 mg/L, Thiamine HCl 0.01 g/L, Nicotinic acid 1 mg/L, Pyridoxine HCl 1 mg/L) added with 40 mg/L Acetosyringone (3',5'-Dimethoxy-4'-hydroxy-acetophenone) and cultured with shaking at 25° C. for 2 hr. The suspension was diluted with AAI liquid medium containing 40 mg/ml Acetosyringone to prepare a suspension (120 ml) (OD600=0.008).

3-3. Introduction of pRIT3-EGFP, pRIT3-mEGFP into Rice Callus (*Agrobacterium* Inoculation, Cocultivation, Bacterial Elimination, Rice Recombinant Callus Selection)

Rice callus (about 5 g) was collected in a sterilized glass beaker, *Agrobacterium* suspension (mentioned earlier) introduced with each vector was added, and inoculated for 3-5 min with shaking. The suspension was filtered through a stainless mesh (joint opening 1.5 mm) and redundant *Agrobacterium* was removed. Then, sterilization filter paper was placed on 2N6 coculture medium (mixed salt for N6 medium (manufactured by Sigma) 4.0 g/L, Casamino acid 300 mg/L, Myo-inocitol 100 mg/L, Nicotinic acid 0.5 mg/L, Pyridoxine HCl 0.5 mg/L, Thiamine HCl 0.5 mg/L, Sucrose 30.0 g/L, Glucose 10 g/L, 2,4-D 2 mg/L, Gelrite 4.0 g/L, Acetosyringone 40 mg/L, pH 5.2), on which callus was arranged at equal distance with tweezers, and cocultured in a dark place at 25° C. for 3 days. Thereafter, for bacterial elimination of *Agrobacterium* from callus after cocultivation, callus was collected in a 500 ml beaker, and washed with bacterial elimination liquid 1 (sterile water containing Vancomycin 200 mg/L, Tween20 20 μl/L) (300 ml) with stirring for 30 min. Thereafter, callus was collected on a stainless mesh, water around callus was removed with paper towel, and bacterial elimination operation was repeated 4 times using bacteria elimination liquid 2 (sterile water containing Vancomycin 200 mg/L, Tween20 20 μl/L) (300 ml). Then, callus after bacteria elimination was cultured for 5 days in 2N6NU medium (mixed salt for N6 medium [manufactured by Sigma] 4.0 g/L, Casamino acid 300 mg/L, Myo-inocitol 100 mg/L, Nicotinic acid 0.5 mg/L, Pyridoxine HCl 0.5 mg/L, Thiamine HCl 0.5 mg/L, L-Proline 2878 mg/L, Sucrose 30.0 g/L, 2,4-D 2 mg/L, Gelrite 4.0 g/L, Vancomycin 100 mg/L, Meropenem 25 mg/L, pH 5.8). Thereafter, callus was arranged at equal distance on selection medium 2N6SEPa50 (mixed salt for N6 medium [manufactured by Sigma] 4.0 g/L, Casamino acid 300 mg/L, Myo-inocitol 100 mg/L, Nicotinic acid 0.5 mg/L, Pyridoxine HCl 0.5 mg/L, Thiamine HCl 0.5 mg/L, L-Proline 2878 mg/L, Sucrose 30.0 g/L, 2,4-D 2 mg/L, Agarose 8.0 g/L, Vancomycin 100 mg/L, Meropenem 25 mg/L, pH 5.8) containing Paromomycin (50 mg/L), and cultured in a dark place at 31.5° C. for about 6 weeks. As a result, multiple lineages of paromomycin resistance callus could be selected.

Figure 2:
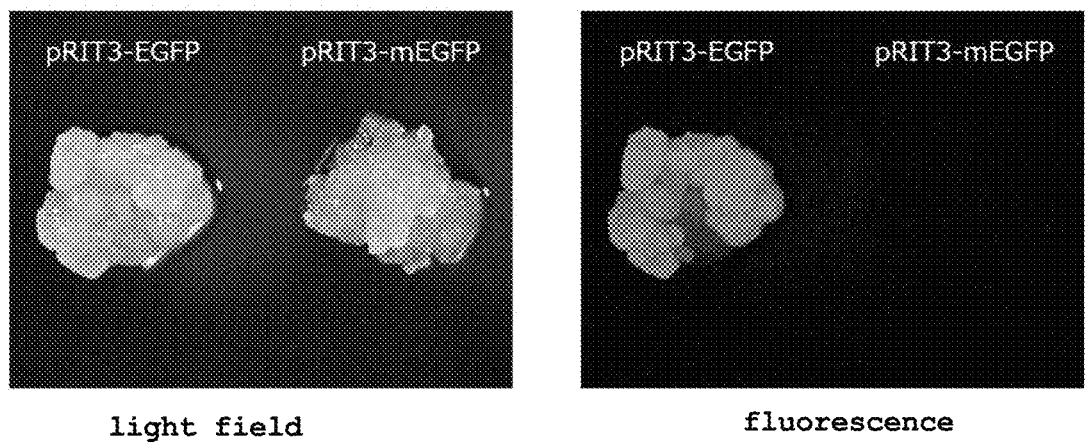
FIG. 2 shows expression of EGFP in rice callus into which two kinds of vectors for Target-AID evaluation are introduced.

3-4. Analysis of Rice Callus in which pRIT3-EGFP, pRIT3-mEGFP were Introduced 96 lineages were randomly selected from calluses that showed paromomycin resistance after introduction of pRIT3-EGFP and used for the analysis thereafter. Genome DNA was extracted from a part of the callus of each lineage by an automatic nucleic acid extraction apparatus (Kurabo Industries PX-80). As a result of PCR analysis using primer sets "SbfI-p35S-F" (SEQ ID NO: 13) and "EGFP-NotI-R" (SEQ ID NO: 14) (Table 1), 1238 bp DNA fragment derived from pRIT3-EGFP was detected and gene recombinants could be confirmed. As a result of observation thereof using a stereoscopic fluorescence microscope, EGFP signal was detected in all of them (FIG. 2). A similar analysis was performed for callus with introduction of pRIT3-mEGFP, and a gene recombinant was confirmed by PCR analysis. As a result of observation of these using a stereoscopic fluorescence microscope, an EGFP signal was not detected at all (FIG. 2).

TABLE 2

| vector 1 | vector 2 | double transformant selection lineage | GFP signal detection | frequency (%) |
|---|---|---|---|---|
| pRIT3-mEGFP (nptII) | 2408 (hpt) | 269 | 10 | 3.7 |
| pRIT3-mEGFP (nptII) | 2409 (hpt) | 264 | 41 | 15.5 |

Then, all double transformant calluses were observed using a stereoscopic fluorescence microscope. As a result, EGFP expression was confirmed in two lineages (No. 6, 3) incorporating pRIT3-mEGFP and 2409 (FIGS. 4, 5). To confirm genome sequence modification by Target-AID in these calluses, genome DNA was extracted from callus

TABLE 1

| | Vector | Forward Primers | Sequence (5' → 3') | Reverse Primers | Sequence (5' → 3') | Amplified fragment size |
|---|---|---|---|---|---|---|
| hpt region | 2408, 2409 | Hmr-F | ATGAAAAAGCCTGAACTCACCGCGACGTCT | hMR 2408 R-1 | CCTCGCTCCAGTCAATGACCGCTGTTATGC | 658 bp |
| Target region (EGFP) | pRIT3-EGFP pRIT3-mEGFP | SbfI-p35S-F | ATGCATCCTGCAGGCTCTAGAGGATCCCCCCTCAG | EGFP-NotI-R | AGCCGGGCGGCCGCTTTACTTGTACAGCTCGTCCA | 1227 bp 1244 bp |
| Target region (ALS) | 1476, 1477 | ALS cloning-F | AGTCCCTGCAGGTTAATTAACTTGCGCTGCGTTTGTGCGGGTGCG | ALS cloning-R | TGACGGTACCACTAGTTAGTAGTACCCAATAAGATCGACCGAAGAGA | 2819 bp |
| | | ALS F-1 | CCGTAAGAACCACCAGCGACACCACGTCCT | | | |

3-5. Simultaneous Introduction pRIT3-mEGFP and 2408, or pRIT3-mEGFP and 2409 into Rice Callus (*Agrobacterium* Inoculation, Cocultivation, Bacteria Elimination, Rice Recombinant Callus Selection)

The basic operation followed 3-3. Equal amounts of bacterial culture of *Agrobacterium* having pRIT3-mEGFP and bacterial culture of *Agrobacterium* having 2408 or 2409 were mixed and inoculated to rice callus (about 30 g). The operation thereafter to curing culture follows that mentioned above. For selection culture, 2N6SEH40Pa50 medium containing hygromycin 40 mg/L, Paromomycin 50 mg/L was used. After about 6 weeks of selection culture, callus showing resistance to hygromycin and paromomycin could be confirmed in multiple lineages. When pRIT3-mEGFP and 2408 were introduced, 14 lineages were obtained and when pRIT3-mEGFP and 2409 were introduced, 56 lineages were obtained.

3-6. Analysis of Rice Callus with Introduction of pRIT3-mEGFP and 2408, or pRIT3-mEGFP and 2409

Figure 3:
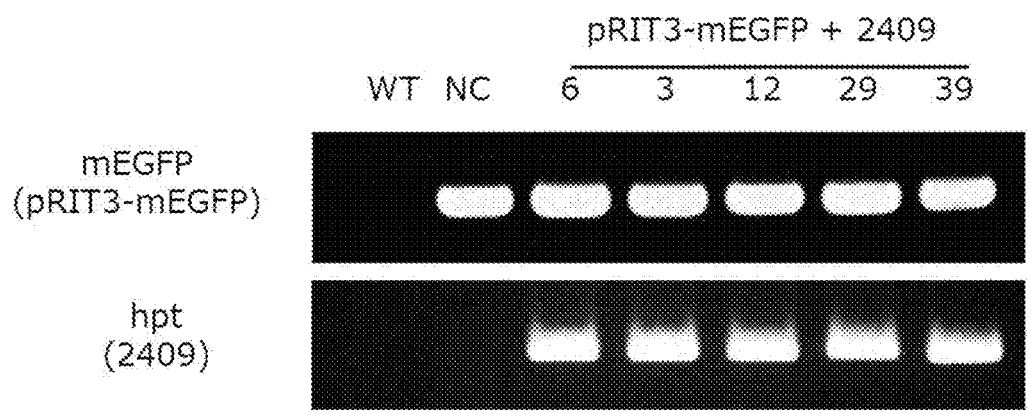
FIG. 3 shows the confirmation results of incorporation of mEGFP and hpt gene by PCR analysis of a double transformant obtained by introducing pRIT3-mEGFP and 2409.

Genome DNA was extracted from the callus of each selected lineage, and PCR analysis using primer sets "SbfI-p35S-F" and "EGFP-NotI-R", and "Hmr-F" (SEQ ID NO: 15) and "Hmr 2408 R-1" (SEQ ID NO: 16) (Table 1) was performed. As a result, 269 lineages contained double transformants incorporating pRIT3-mEGFP and 2408, and 264 lineages contained those incorporating pRIT3-mEGFP and 2409 (Table 2, FIG. 3).

expressing EGFP in each lineage, PCR product using primer sets "SbfI-p35S-F" and "EGFP-NotI-R" (Table 1) was purified by MonoFas DNA purification kit I (GL Sciences Inc.) and cloned between SbfI and NotI sites of pCR4 Blunt TOPO vector (ThermoFisher Inc.). The base sequence of 111 clones in total was decoded by a DNA sequencer. As a result, base sequence modification by Target-AID was confirmed in a part thereof (Table 3, FIG. 6A, B). In nickase type 2409, the frequency of short deletion mutation (1-20 nucleotides) was high, but base substitution alone could also occur (FIG. 7).

TABLE 3

| number of analyzed clones | base substitution | Deletion | no mutation |
|---|---|---|---|
| 111 | 3 (2.7%) | 7 (6.3%) | 101 (91.0%) |

Figure 8:
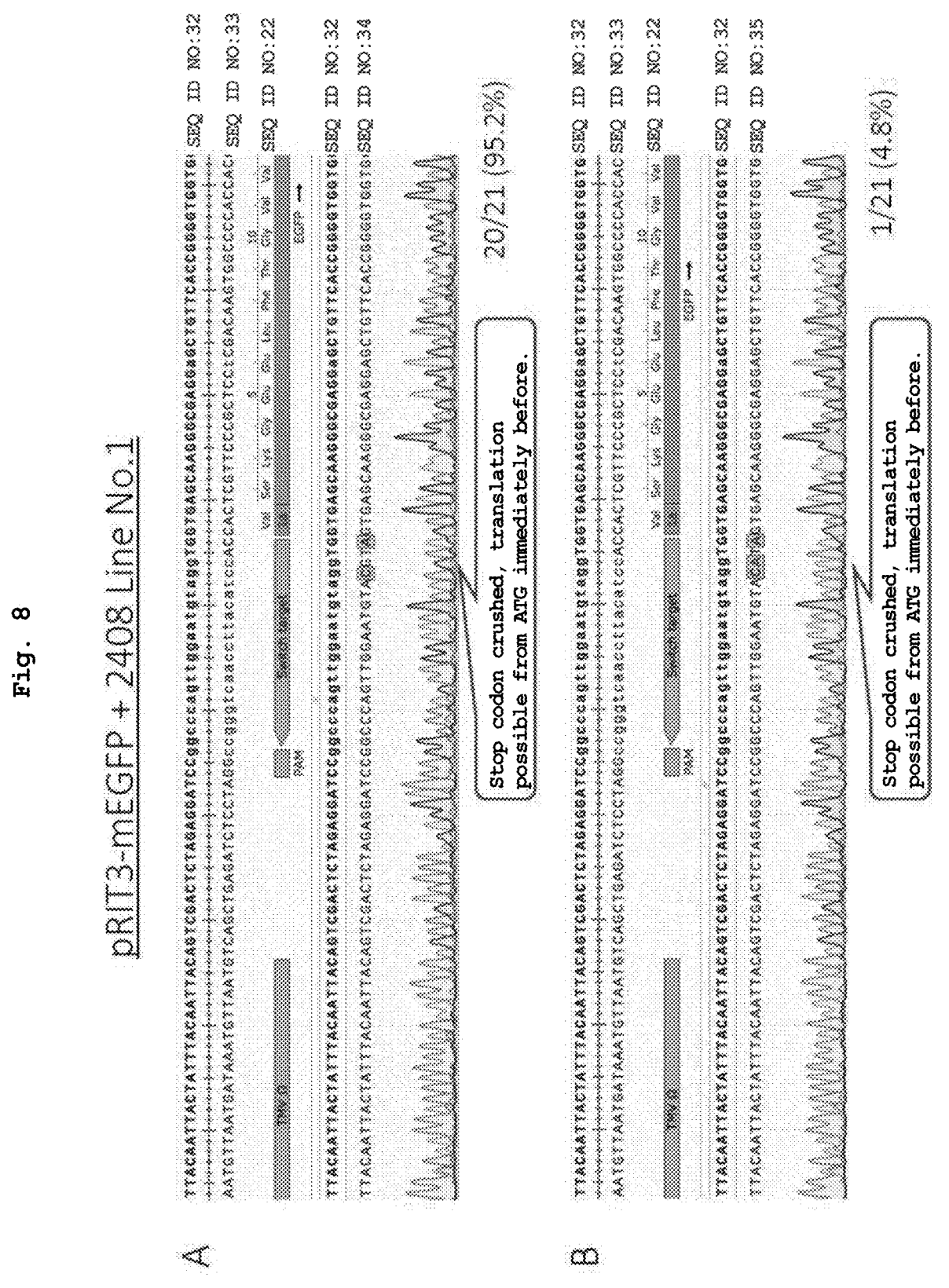
Figure 9:
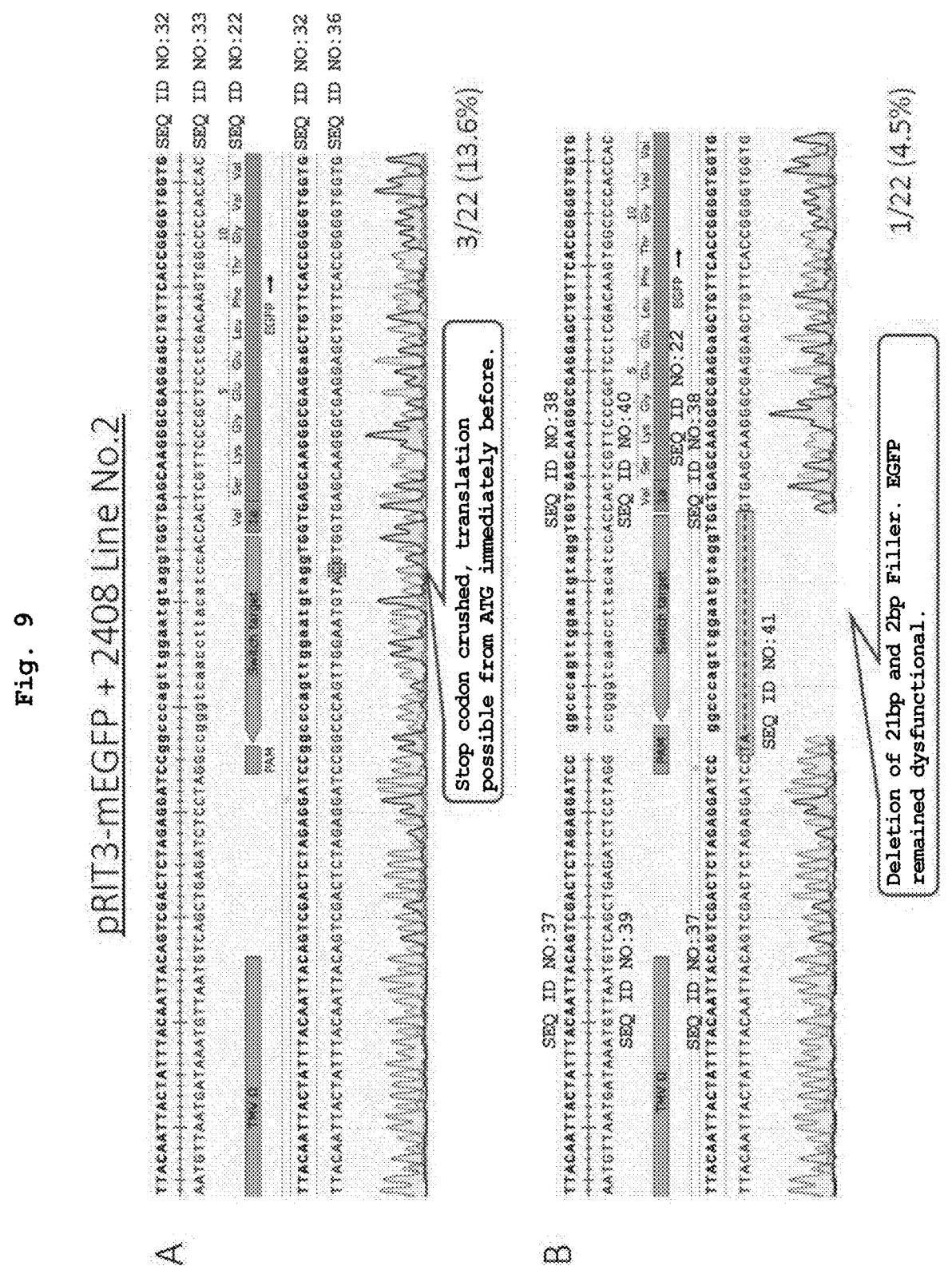
Figure 10:
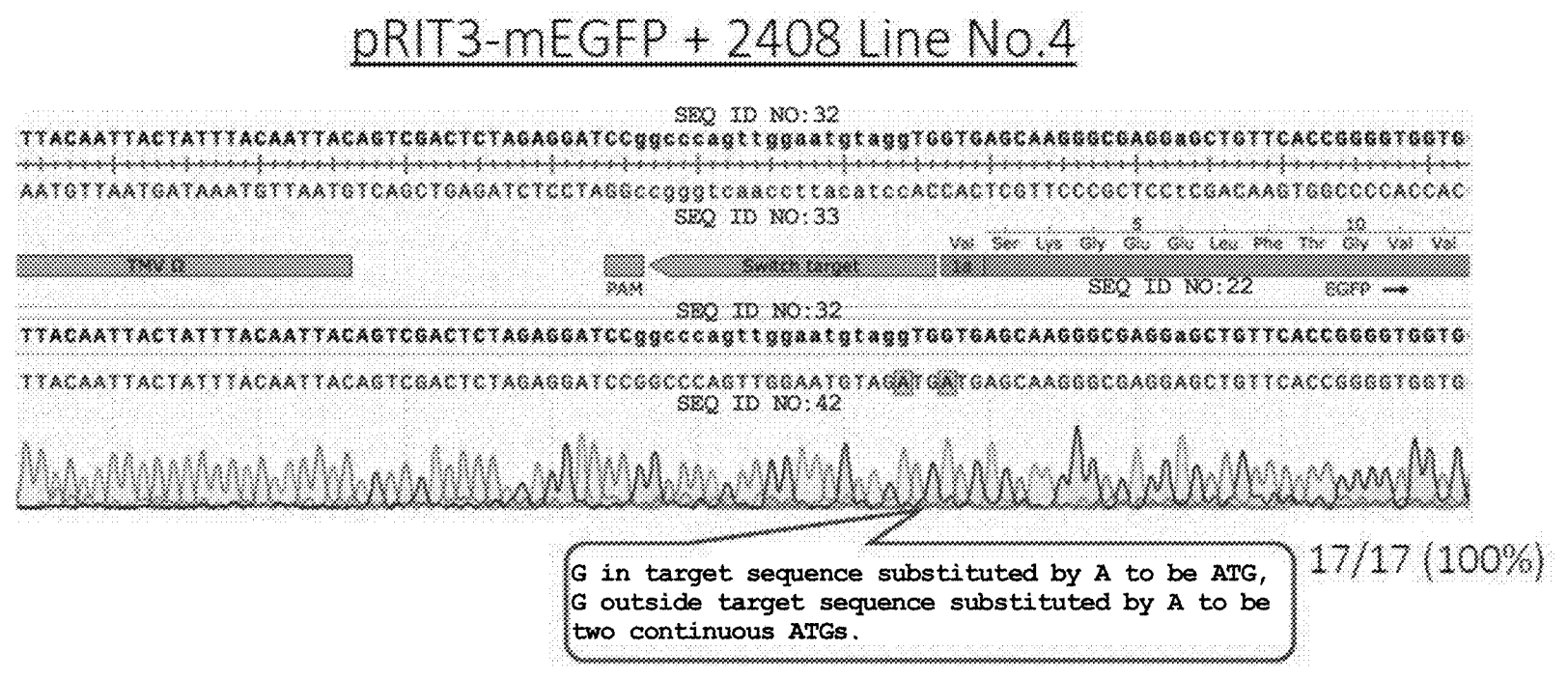

On the other hand, when Cas9 (2408) lacking cleavage ability of both strands was used, the mutation introduction manner was mainly base substitution (FIGS. 8, 9, 10), the region where base substitution occurred was wider than by the budding yeast, and it was confirmed outside the target nucleotide sequence (21 nucleotides upstream of PAM sequence) (FIG. 10). In GFP signal negative cells, mutation was not introduced in the target nucleotide sequence and the vicinity thereof (FIG. 11).

4. Modification of Endogenous Gene ALS (Acetolactate Synthase) of Rice

In the above, modification of exogenous reporter gene by Target-AID was successful. Then, modification of rice endogenous gene was performed. As the target, ALS (Acetolactate synthase) gene was selected, and creation of a mutation-type ALS gene (ALS A96V) in which 96th amino acid is changed from alanine (A) to valine (V) via target base substitution in the gene sequence was tried. From previous reports on other plants, the plant body and callus of rice expressing ALS A96V are predicted to acquire resistance to herbicide (Imazamox) from previous reports in other plants, but there is no preceding example. There is no case testing the effect of Imazamox on rice plant body and callus under aseptic culture conditions. Therefore, in this example, as a preliminary study, Imazamox's effective concentration test for rice seed and callus under aseptic culture conditions (the following 4-1, 4-2) and acquisition of resistance to Imazamox by ALS A96V were first confirmed (the following 4-3), and ALS A96V modification by Target-AID was performed (the following 4-4).

4-1. Verification of Effective Concentration of Imazamox on Rice Plant Body Under Aseptic Culture Conditions Based on 1/2 MS solid medium (MS mix (Sigma), sucrose 15.0 g/L, Gelrite (Wako Pure Chemical Industries, Ltd.) 4.0 g/L, pH 5.8), media in 9 stages (0 mg/L, 0.5 mg/L, 1 mg/L, 2 mg/L, 4 mg/L, 5 mg/L, 10 mg/L, 20 mg/L, 30 mg/L) with different Imazamox concentrations were produced. Successively, chaff of rice (*Oryza sativa*. L Japonica brand; Nipponbare) seeds was removed, the seeds were shaken in 70% ethanol for 1 min, and sterilized by immersing in 2.5% sodium hypochlorite for 20-30 min while allowing for penetration. The sterilized seeds were inoculated by 24 seeds per treatment area, cultured at 25° C. for 11 hr light (8000 lux)/for 13 hr dark for 7 days, and germination circumstances were observed. As a result, 23 seeds out of 24 germinated in 1/2 MS medium free of Imazamox and showed steady growth. In the medium added with Imazamox at a concentration of 0.5 mg/L or more, browning of embryo stem and whitening of coleoptile was confirmed in all seeds, and they stretched to about 5 mm (Table 4).

From the above, it was determined that the effective concentration of Imazamox under the aseptic culture conditions for rice plant body was 0.5 mg/L.

From the above, it was determined that the effective concentration of Imazamox for rice callus was 70 mg/L.

4-3. Imazamox Resistance Imparted to Rice Callus by Mutation-Type ALS Gene (ALS A96V)

To evaluate Imazamox resistance to rice callus by mutation-type ALS A96V, pRIT4-ALS WT and pRIT4-ALS A96V were constructed (FIG. 13). pRIT4 is a binary vector for rice transformation, and has Hygromycin phosphotransferase (hpt) as a positive marker gene for plants. pRIT4-ALS WT is based on the genome DNA extracted from wild-type rice (*Oryza sativa*. L Japonica brand; Nipponbare) and obtained by isolating ALS gene, promoter and transcription termination region thereof by PCR cloning and incorporating them into pRIT4. pRIT4-ALS A96V is obtained by producing ALS gene into which A96V mutation is artificially introduced by site specific mutation introduction method via PCR and incorporating same into pRIT4. These two kinds of vectors were introduced (mentioned earlier) into *Agrobacterium* EHA101 lineage to transform (mentioned earlier) callus derived from rice seed scutellum. Thereafter, callus was arranged at equal distance on selection medium (2N6SEH50; mixed salt for N6 medium [manufactured by Sigma] 4.0 g/L, Casamino acid 1000 mg/L, Myo-inocitol 100 mg/L, Nicotinic acid 0.5 mg/L, Pyridoxine HCl 0.5 mg/L, Thiamine HCl 0.5 mg/L, L-Proline 2878 mg/L, Sucrose 30.0 g/L, 2,4-D 2 mg/L, Gelrite 4.0 g/L, Vancomycin 100 mg/L, Meropenem 25 mg/L, pH 5.8) added with hygromycin 40 mg/L, and cultured at 31.5° C. in a dark place for about 4 weeks. As a result, 169 lineages of callus into which pRIT4-ALS WT was introduced, and 263 lineages of callus into which pRIT4-ALS A96V was introduced were obtained (Table 5). In the subsequent steps, these calluses were individually cultured for each lineage. Each callus lineage proliferated on 2N6SEH50 medium was passaged in a selection medium (2N6SEH40IMZ70) which is 2N6SEH40 added with Imazamox 70 mg/L and cultured at 31.5° C. in a dark place for about 6 weeks. As a result, of the calluses with pRIT4-ALS WT introduction, 6 lineages of callus (3.6%) showed resistance to Imazamox 70 mg/L. When pRIT4-ALS A96V was introduced, 261 lineages (99.2%) showed resistance (Table 5).

TABLE 4

Evaluation of effective concentration of Imazamox on rice plant body

| | concentration of Imazamox added to ½ MS medium | | | | | | | | |
|---|---|---|---|---|---|---|---|---|---|
| number of seeds | 0 mg/L | 0.5 mg/L | 1 mg/L | 2 mg/L | 4 mg/L | 5 mg/L | 10 mg/L | 20 mg/L | 30 mg/L |
| aseptic seeding germination | 24 | 24 | 23 | 24 | 24 | 24 | 24 | 24 | 24 |
| (7 days later) | 23 | 0 | 0 | 0 | 0 | 0 | 0 | 0 | 0 |
| survival rate (%) | 95.8 | 0 | 0 | 0 | 0 | 0 | 0 | 0 | 0 |

4-2. Verification of Effective Concentration of Imazamox on Rice Callus Under Aseptic Culture Conditions Based on 2N6 solid medium (mentioned earlier), media in 4 stages (0 mg/L, 30 mg/L, 50 mg/L, 70 mg/L) with different Imazamox concentrations were produced. Callus was induced from the scutellum part of rice seed (mentioned earlier), inoculated to 2N6 solid medium added with Imazamox, cultured at 31.5° C. for 28 days in the dark all day, and the proliferation state of the callus was confirmed. As a result, callus bloated to a certain extent in a medium added with Imazamox 70 mg/L but mitotic proliferation was inhibited. In contrast, mitotic proliferation of callus was observed at a concentration of 50 mg/L or below (FIG. 12).

From the above, Imazamox resistance imparted to rice callus by mutation-type ALS A96V could be confirmed.

TABLE 5

Imazamox resistance imparted to rice callus by mutation-type ALS A96V

| | vector | Hm resistance | IMZ resistance | (%) |
|---|---|---|---|---|
| ALS (WT) | pRIT4-ALS WT | 169 | 6 | 3.6 |
| ALS (A96V) | pRIT4-ALS A96V | 263 | 261 | 99.2 |

4-4. ALS A96V Modification by Target-AID

Figure 14:
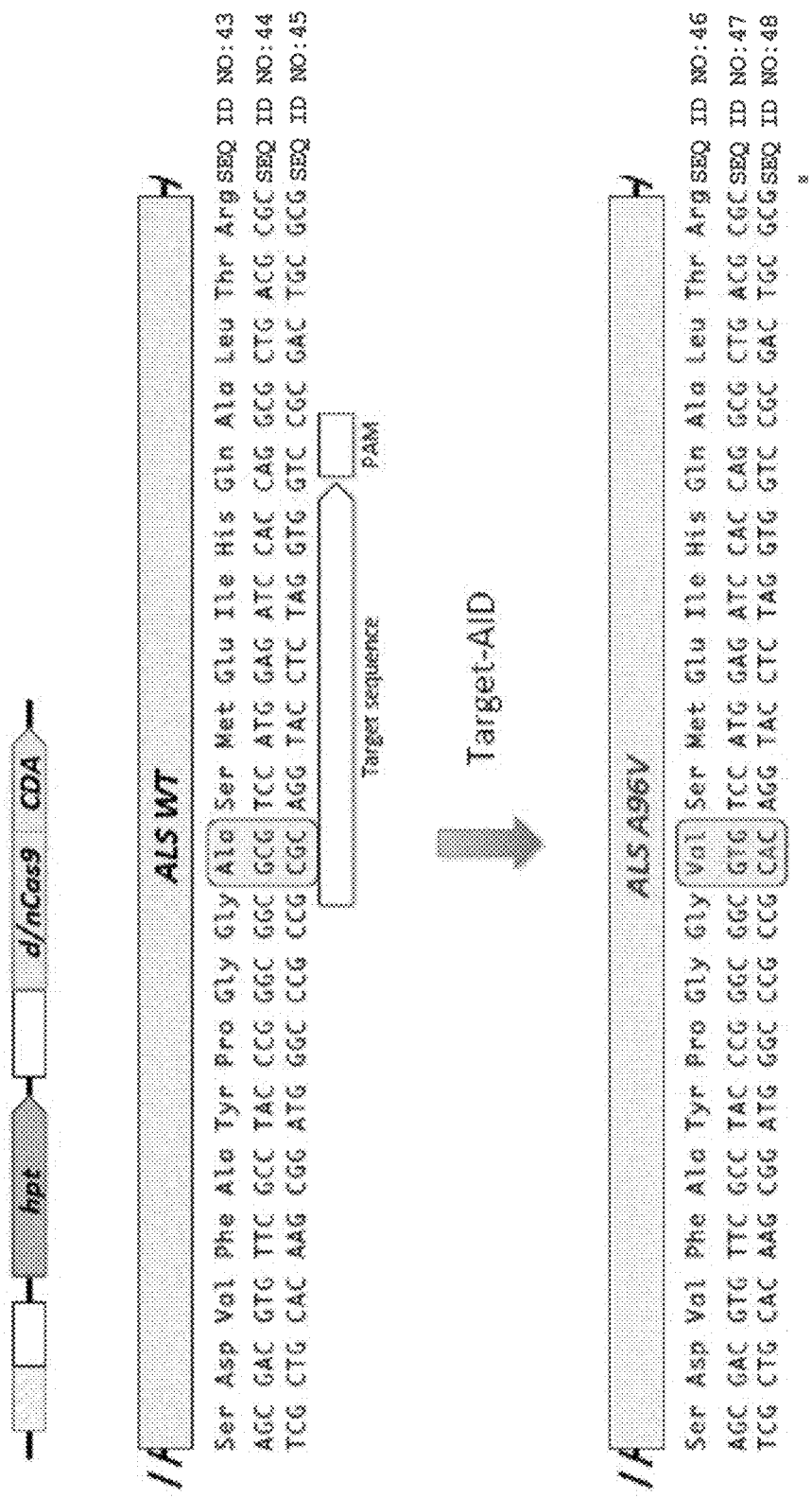
FIG. 14 shows the target sequence of rice ALS A96V modification by Target-AID.

Target-AID vectors 1476 (dCas-AID) and 1477 (nCas-AID) were designed to be modified to ALS A96V via target base substitution (C287T) to ALS gene in rice genome (FIG. 14). 1476, 1477 were introduced (mentioned earlier) into *Agrobacterium* EHA101 lineage, and used for transformation (mentioned earlier) to callus (about 8 g) derived from rice seed embryo. The callus that underwent *Agrobacterium* inoculation and bacterial elimination was curing cultured in 2N6NU medium for 14 days, and arranged at equal distance on selection medium (2N6SEH40) added with hygromycin 40 mg/L, and cultured at 31.5° C. in a dark place for about 3 weeks. Then it was passaged in the same medium and cultured at 25° C. in a dark place for about 10 weeks to give 155 lineages of callus with 1476 introduction and 203 lineages of callus with 1477 introduction. In the subsequent steps, lineages were individually cultured. The calluses of each lineage were divided into two, passaged in a medium added with hygromycin (50 mg/L) (2N6SEH50) and a medium added with Imazamox 70 mg/L (2N6SEH50IMZ70), and selection cultured at 31.5° C. in a dark place for about 6 weeks. As a result of culturing on 2N6SEH50, calluses of all lineages proliferated. When cultured on 2N6SEH50IMZ70, proliferation was found in 3 lineages of callus with 1476 introduction and 6 lineages of callus with 1477 introduction. To confirm ALS gene sequence in these 9 lineages of callus, genome DNA was extracted, and SbfI and NotI recognition sites were added while amplifying DNA fragments by PCR using primer sets "ALS cloning-F" (SEQ ID NO: 17) and "ALS cloning-R" (SEQ ID NO: 18). The obtained PCR products were purified by MonoFas DNA purification kit I (GL Sciences Inc.) and cloned between SbfI-NotI site of cloning vector obtained by modifying pDONRZeo (Thermo Fisher Scientific Inc.). The base sequence of the obtained plasmid clone was analyzed by a DNA sequencer (ABI, 3130XL) using primer "ALS F-1" (SEQ ID NO: 19). The primer sequence used is shown in Table 1.

Figure 15:
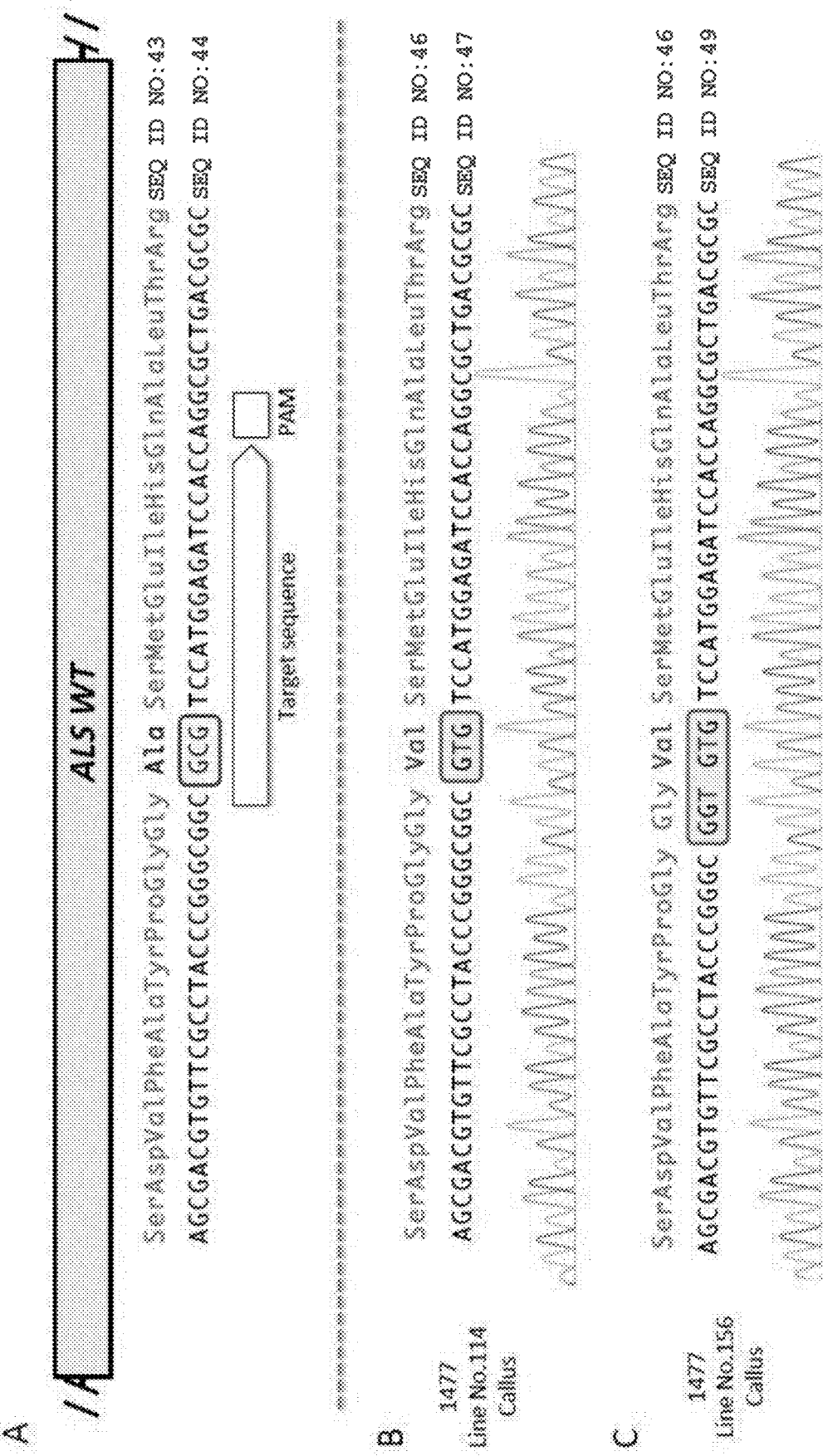
FIG. 15 shows modification of rice ALS gene by Target-AID.
Figure 16:
FIG. 16 is a photograph of T0 plant body redifferentiated from rice ALS A96V modification callus by Target-AID.

As a result, of 6 lineages with introduction of 1477 and showing Imazamox resistance, A96V mutation was introduced in ALS gene of 4 lineages. In 3 lineages, substitution (C287T) of target base causing A96V mutation was confirmed (FIG. 15B). In the remaining one lineage, C285T with no change of amino acid sequence was also confirmed in addition to C287T (FIG. 15C). These are all base substitution of C in the target sequence of vector 1477 to T. Regarding these lineages, ALS gene, promoter thereof and the genomic sequence of the transcription termination region were confirmed, but mutation other than C285T and C287T were not confirmed. Therefore, modification of rice endogenous ALS gene by Target-AID and herbicide resistance imparted thereby were judged to be successful. In 3 lineages out of 4 lineage successful in introduction of A96V mutation into ALS gene, TO plant body was successfully redifferentiated (FIG. 16). The DNA fragment of the obtained TO plant body, which was amplified by PCR using "ALS cloning-F" and "ALS cloning-R", was directly sequenced using "ALS F-1". As a result, the same mutation (C287T or C285T/C287T) as in the callus from which all TO plant bodies were derived was confirmed (FIG. 17).

5. Simultaneous Modification of Multiple Genes by Target-AID

Figure 18:
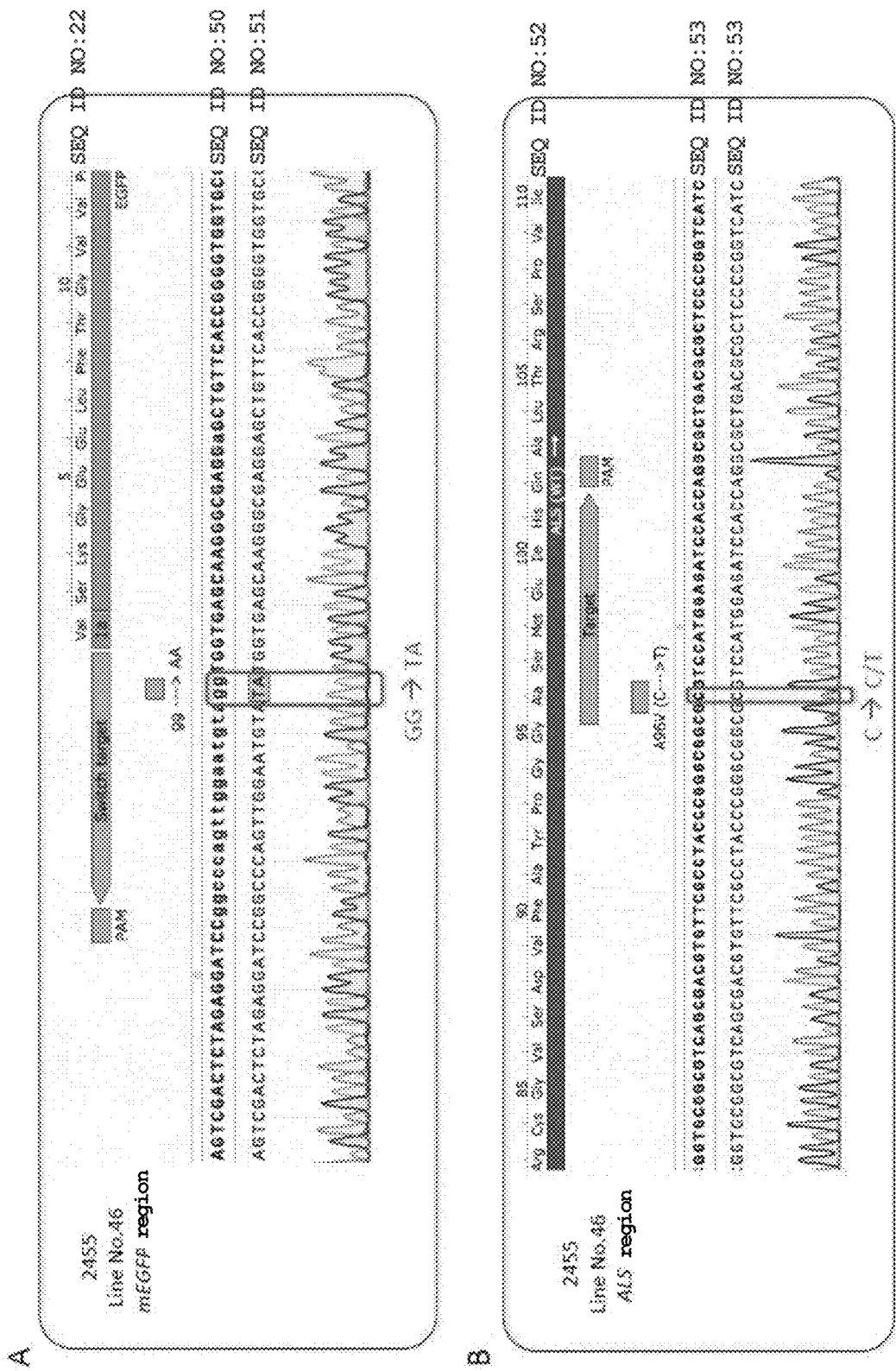
FIG. 18 shows simultaneous modification of multiple genes by Target-AID.

Target-AID vector 2455 (dCas-AID) was produced for simultaneous modification of mEGFP gene on pRIT3-mEGFP and rice endogenous ALS gene, and respectively expresses the same gRNA as 2408/2409 and 1476/1477. 2455 was introduced by the aforementioned method into callus (about 17 g) into which pRIT3-mEGFP was introduced to give 124 lineages of double transformant lineage. These were observed under a stereoscopic fluorescence microscope and expression of EGFP was confirmed in 3 lineages. Furthermore, these 3 lineages of callus were passaged in 2N6SEH40IMZ70 medium, and cultured at 31.5° C. in a dark place for about 6 weeks. As a result, all showed Imazamox resistance and actively proliferated. Genome DNA was extracted from 3 lineages of callus, and mEGFP gene region and ALS gene region were amplified by PCR using primer sets "SbfI-p35S-F" and "EGFP-NotI-R", or "ALS Cloning-F" and "ALS Cloning-R". The obtained PCR products were purified by MonoFas DNA purification kit I (GL Sciences Inc.) and subjected to direct sequencing. As a result, target base substitution by Target-AID was confirmed in both mEGFP gene and ALS gene in one lineage (FIG. 18). The stop codon (TAG) set immediately after the initiation codon of the mEGFP gene was modified to TAT corresponding to tyrosine, and the immediately subsequent GTG was modified to ATG corresponding to methionine (FIG. 18A). C287T was confirmed in ALS gene (FIG. 18B).

From the above, it was demonstrated that multiple target sequences in rice genome can be simultaneously modified by Target-AID.

INDUSTRIAL APPLICABILITY

According to the present invention, a site specific mutation can be safely introduced into any monocot without accompanying DNA double strand cleavage. The thus-obtained genetically modified monocot is extremely useful for molecular breeding of monocot including major grains such as rice and the like.

This application is based on patent application No. 2015-232379 filed in Japan (filing date: Nov. 27, 2015) and patent application No. 2016-134613 filed in Japan (filing date: Jul. 6, 2016), the contents of which are incorporated in full herein.

The invention claimed is:

1. A method of modifying a targeted site of a double stranded DNA of a monocot cell, comprising a step of contacting a complex wherein a nucleic acid sequence-recognizing module that specifically binds to a target nucleotide sequence in the double stranded DNA and a nucleic acid base converting enzyme are bonded, with the double stranded DNA, to convert one or more nucleotides in the targeted site to one or more different nucleotides or delete one or more nucleotides, or insert one or more nucleotides into the targeted site, without cleaving at least one strand of the double stranded DNA in the targeted site, wherein the double stranded DNA is contacted with the complex by introducing a nucleic acid encoding the complex into the monocot cell and culturing the monocot cell to intracellularly express the complex, and wherein a nuclear localization signal is added to both terminals of the nucleic acid sequence-recognizing module and the nucleic acid base converting enzyme, wherein the monocot is rice.

2. The method according to claim 1, wherein the culture step is at least partly performed at a temperature lower than the optimal culture temperature of the monocot cell.

3. The method according to claim 1, wherein the nucleic acid sequence-recognizing module is selected from the group consisting of a CRISPR-Cas system wherein at least one DNA cleavage ability of Cas is inactivated, a zinc finger motif, a TAL effector and a PPR motif.

4. The method according to claim 1, wherein the nucleic acid sequence-recognizing module is a CRISPR-Cas system wherein at least one DNA cleavage ability of Cas is inactivated.

5. The method according to claim 4, wherein the nucleic acid sequence-recognizing module is a CRISPR-Cas system in which a cleavage ability of an opposite strand of the strand forming a complementary strand with a guide RNA is inactivated.

6. The method according to claim 5, wherein one or more nucleotides of the targeted site are deleted.

7. The method according to claim 1, wherein the nucleic acid base converting enzyme is deaminase.

8. The method according to claim 7, wherein the deaminase is cytidine deaminase.

9. The method according to claim 8, wherein the cytidine deaminase is PmCDA1 derived from *Petromyzon marinus*.

10. The method according to claim 1, wherein the nucleic acid sequence encoding the nucleic acid sequence-recognizing module and the nucleic acid base converting enzyme is optimized for use of a codon of angiosperm or monocot.

11. The method according to claim 1, wherein the targeted site is monomeric enhanced green fluorescent protein (mEGFP) gene, rice acetolactate synthase (ALS) gene, or both mEGFP gene and rice ALS gene.

12. The method according to claim 11, wherein the targeted site is the mEGFP gene.

13. The method according to claim 11, wherein the targeted site is the rice ALS gene.

14. The method according to claim 11, wherein the targeted site is both the mEGFP gene and the rice ALS gene.

* * * * *